US012673918B2

(12) United States Patent
Roden et al.

(10) Patent No.: US 12,673,918 B2
(45) Date of Patent: Jul. 7, 2026

(54) SMALL MOLECULE RPN13 INHIBITORS WITH ANTITUMOR PROPERTIES

(71) Applicant: The Johns Hopkins University, Baltimore, MD (US)

(72) Inventors: Richard B.S. Roden, Baltimore, MD (US); Ravi K. Anchoori, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1058 days.

(21) Appl. No.: 17/781,507

(22) PCT Filed: Dec. 4, 2020

(86) PCT No.: PCT/US2020/063456
§ 371 (c)(1),
(2) Date: Jun. 1, 2022

(87) PCT Pub. No.: WO2021/113743
PCT Pub. Date: Jun. 10, 2021

(65) Prior Publication Data
US 2023/0045142 A1 Feb. 9, 2023

Related U.S. Application Data

(60) Provisional application No. 63/057,778, filed on Jul. 28, 2020, provisional application No. 62/944,957, filed on Dec. 6, 2019.

(51) Int. Cl.
*C07D 211/86* (2006.01)
*A61P 35/00* (2006.01)
*C07D 471/08* (2006.01)

(52) U.S. Cl.
CPC ............ *C07D 211/86* (2013.01); *A61P 35/00* (2018.01); *C07D 471/08* (2013.01)

(58) Field of Classification Search
CPC .................................................... C07D 211/86
See application file for complete search history.

(56) References Cited

U.S. PATENT DOCUMENTS

| | | | | |
|---|---|---|---|---|
| 9,913,834 | B2 * | 3/2018 | Roden | A61K 31/45 |
| 10,500,198 | B2 * | 12/2019 | Roden | A61K 31/439 |
| 2007/0270464 | A1 | 11/2007 | Liotta et al. | |
| 2016/0106725 | A1 | 4/2016 | Roden et al. | |

FOREIGN PATENT DOCUMENTS

WO 2019/152536 A1 8/2019

OTHER PUBLICATIONS

Cresta et al., "Phase I study of bortezomib with weekly paclitaxel in patients with advanced solid tumours", Eur J Cancer, (2008), vol. 44, pp. 1829-1834.
Aghajanian et al., "A phase II evaluation of bortezomib in the treatment of recurrent platinum-sensitive ovarian or primary peritoneal cancer: a Gynecologic Oncology Group study", Gynecol Oncol., (2009), vol. 115, pp. 215-220.
Parma et al., "An open-label phase 2 study of twice-weekly bortezomib and intermittent pegylated liposomal doxorubicin in patients with ovarian cancer failing platinum-containing regimens", Int J Gynecol Cancer, (2012), vol. 22, No. 5, pp. 792-800.
Kobrinsky et al., "A phase I and pharmacokinetic study of oxaliplatin and bortezomib: activity, but dose-limiting neurotoxicity", Cancer Chemother Pharmacol., (2013), vol. 72, pp. 1073-1078.
Jandial et al., "A phase I pharmacokinetic study of intraperitoneal bortezomib and carboplatin in patients with persistent or recurrent ovarian cancer: An NRG Oncology/Gynecologic Oncology Group study", Gynecol Oncol., (2017), vol. 145, No. 2, pp. 236-242.
Grice et al., "The recognition of ubiquitinated proteins by the proteasome", Cell Mol Life Sci., (2016), vol. 73, pp. 3497-3506.
Hamazaki et al., "Redundant Roles of Rpn10 and Rpn13 in Recognition of Ubiquitinated Proteins and Cellular Homeostasis", PLoS Genet., (2015), vol. 11, No. 7, e1005401, (20 pages).
Berko et al., "Inherent asymmetry in the 26S proteasome is defined by the ubiquitin receptor RPN13", J Biol Chem., (2014), vol. 289, No. 9, pp. 5609-5618.
Hemmis et al., "Phosphorylation of Tyr-950 in the proteasome scaffolding protein RPN2 modulates its interaction with the ubiquitin receptor RPN13", J Biol Chem., (2019), vol. 294, No. 25, pp. 9659-9665.
Aguileta et al., "The E3 ubiquitin ligase parkin is recruited to the 26 S proteasome via the proteasomal ubiquitin receptor Rpn13", J Biol Chem, (2015), vol. 290, No. 12, pp. 7492-7505.
Al-Shami et al., "Regulators of the proteasome pathway, Uch37 and Rpn13, play distinct roles in mouse development", PLoS One, (2010), vol. 5, Issue 10, e13654, (11 pages).
Jandial et al., "Enhanced delivery of cisplatin to intraperitoneal ovarian carcinomas mediated by the effects of bortezomib on the human copper transporter 1", Clin Cancer Res., (2009), vol. 15, No. 2, pp. 553-560.
Jannuzzi et al., "Higher proteotoxic stress rather than mitochondrial damage is involved in higher neurotoxicity of bortezomib compared to carfilzomib", Redox Biol., (2020), vol. 32, 101502, (12 pages).
Ling et al., "Reactive oxygen species generation and mitochondrial dysfunction in the apoptotic response to Bortezomib, a novel proteasome inhibitor, in human H460 non-small cell lung cancer cells", J Biol Chem., (2003), vol. 278, No. 36, pp. 33714-33723.
Ludman et al., "Bortezomib-induced aerobic glycolysis contributes to chemotherapy-induced painful peripheral neuropathy", Mol Pain, (2019), vol. 15, pp. 1-17.
Mofers et al., "Analysis of determinants for in vitro resistance to the small molecule deubiquitinase inhibitor b-AP15", PLoS One, (2019), vol. 14, No. 10, e0223807, (17 pages).
Perez-Galan et al., "The proteasome inhibitor bortezomib induces apoptosis in mantle-cell lymphoma through generation of ROS and Noxa activation independent of p53 status", Blood, (2006), vol. 107, No. 1, pp. 257-264.

(Continued)

*Primary Examiner* — John S Kenyon
*Assistant Examiner* — Rehana Ismail
(74) *Attorney, Agent, or Firm* — Venable LLP; Keith G. Haddaway

(57) ABSTRACT

Compounds of formula (I), (II), and (III) having the structure shown below are presented: wherein R-$R_6$ are defined herein. These molecules work as proteasome inhibitors and bind to the RPN13 subunit of the 19S regulatory particle, and can be used in methods of treating a condition or a disease, such as cancer, in a mammal.

18 Claims, 21 Drawing Sheets

(56) References Cited

OTHER PUBLICATIONS

Roby et al., "Development of a syngeneic mouse model for events related to ovarian cancer", Carcinogenesis, (2000), vol. 21, No. 4, pp. 585-591.
Rowinsky et al., "Phase 1 study of the protein deubiquitinase inhibitor VLX1570 in patients with relapsed and/or refractory multiple myeloma", Invest New Drugs, (2020), vol. 38, pp. 1448-1453.
Schwertman et al., "Regulation of DNA double-strand break repair by ubiquitin and ubiquitin-like modifiers", Nat Rev Mol Cell Biol., (2016), vol. 17, pp. 379-394.
Wang et al., "Synthesis and evaluation of derivatives of the proteasome deubiquitinase inhibitor b-AP15", Chem Biol Drug Des., (2015), vol. 86, pp. 1036-1048.
Wilson et al., "Synaptic defects in ataxia mice result from a mutation in Usp14, encoding a ubiquitin-specific protease", Nat Genet., (2002), vol. 32, pp. 420-425.
Xing et al., "A mouse model for the molecular characterization of brca1-associated ovarian carcinoma.", Cancer Res., (2006), vol. 66, No. 18, pp. 8949-8953.
Zheng et al., "Mitotoxicity and bortezomib-induced chronic painful peripheral neuropathy", Exp Neurol., (2012), vol. 238, pp. 225-234.
Conejo-Garcia et al., "Tumor-infiltrating dendritic cell precursors recruited by a beta-defensin contribute to vasculogenesis under the influence of Vegf-A", Nat Med., (2004), vol. 10, No. 9, pp. 950-958.
Hochstrasser, "Ubiquitin and intracellular protein degradation", Curr Opin Cell Biol., (1992), vol. 4, No. 6, pp. 1024-1031.
Dou et al., "Overview of proteasome inhibitor-based anti-cancer therapies: perspective on bortezomib and second-generation proteasome inhibitors versus future generation inhibitors of ubiquitin proteasome system", Curr Cancer Drug Targets., (2014), vol. 16, No. 6, pp. 517-536.
Broyl et al., "Mechanisms of peripheral neuropathy associated with bortezomib and vincristine in patients with newly diagnosed multiple myeloma: a prospective analysis of data from the HOVON-65/GMMG-HD4 trial", Lancet Oncol., (2010), vol. 11, No. 11, pp. 1057-1065.
Vanderlinden et al., "Structure and energetics of pairwise interactions between proteasome subunits RPN2, RPN13, and ubiquitin clarify a substrate recruitment mechanism", J Biol Chem., (2017), vol. 292, No. 23, pp. 9493-9504.
Liu et al., "Structural basis for the recognition of K48-linked Ub chain by proteasomal receptor Rpn13", Cell Discov., (2019), 5:19 (15 pages).
Lu et al., "Structure of the Rpn13-Rpn2 complex provides insights for Rpn13 and Uch37 as anticancer targets", Nat Commun., (2017); 8:15540, (13 pages).
Lu et al., "A High Affinity hRpn2-Derived Peptide That Displaces Human Rpn13 from Proteasome in 293T Cells", PLoS One, (2015); 10(10):e0140518 (13 pages).
Chen et al., "Structural plasticity allows UCH37 to be primed by RPN13 or locked down by INO80G", Mol Cell., (2015), vol. 57, pp. 767-768.
Jiao et al., "Mechanism of the Rpn13-induced activation of Uch37", Protein Cell, (2014); vol. 5, No. 8, pp. 616-630.
Anchoori et al., "A bis-benzylidine piperidone targeting proteasome ubiquitin receptor RPN13/ADRM1 as a therapy for cancer", Cancer Cell, (2013), vol. 24, No. 6, pp. 791-805.
Song et al., "Development and preclinical validation of a novel covalent ubiquitin receptor Rpn13 degrader in multiple myeloma", Leukemia, (2019), vol. 33, pp. 2685-2694.
Song et al., "Targeting proteasome ubiquitin receptor Rpn13 in multiple myeloma", Leukemia, (2016), vol. 30, pp. 1877-1886.
Anchoori et al., "Covalent Rpn13-Binding Inhibitors for the Treatment of Ovarian Cancer", ACS Omega, (2018), vol. 3, No. 9, pp. 11917-11929.
Kisselev "A novel bullet hits the proteasome", Cancer Cell., (2013), vol. 24, pp. 691-693.
Randles et al., "The Proteasome Ubiquitin Receptor hRpn13 and Its Interacting Deubiquitinating Enzyme Uch37 Are Required for Proper Cell Cycle Progression", J Biol Chem., (2016), vol. 291, No. 16, pp. 8773-8783.
Soong et al., "RPN13/ADRM1 inhibitor reverses immunosuppression by myeloid-derived suppressor cells", Oncotarget, (2016); vol. 7, No. 42, pp. 68489-68502.
Jiang et al., "Early and consistent overexpression of ADRM1 in ovarian high-grade serous carcinoma", J Ovarian Res., (2017), vol. 10:53, (12 pages).
Yu et al., "RA190, a Proteasome Subunit ADRM1 Inhibitor, Suppresses Intrahepatic Cholangiocarcinoma by Inducing NF-KB-Mediated Cell Apoptosis", Cell Physiol Biochem., (2018), vol. 47, pp. 1152-1166.
Rao et al., "Ubiquitin Receptor RPN13 Mediates the Inhibitory Interaction of Diphenyldihaloketones CLEFMA and EF24 With the 26S Proteasome", Front. Chem., (2018), vol. 6, Article 392, (13 pages).
Fejzo et al., "Comprehensive analysis of 20q13 genes in ovarian cancer identifies ADRM1 as amplification target", Genes Chromosomes Cancer, (2008), vol. 47, pp. 873-883.
Fejzo et al., "Amplification Target ADRM1: Role as an Oncogene and Therapeutic Target for Ovarian Cancer", Int J Mol Sci., (2013), vol. 14, pp. 3094-3109.
Lee et al., "Proteasome Inhibitors disrupt the unfolded protein response in myeloma cells", Proc Natl Acad Sci USA, (2003), vol. 100, No. 17, pp. 9946-9951.
Smith et al., "Road to ruin: targeting proteins for degradation in the endoplasmic reticulum", Science, (2011), vol. 334, pp. 1086-1090.
Nawrocki et al., "Bortezomib sensitizes pancreatic cancer cells to endoplasmic reticulum stress-mediated apoptosis", Cancer Res., (2005), vol. 65, No. 24, pp. 11658-11666.
Walter et al., "The unfolded protein response: from stress pathway to homeostatic regulation", Science, (2011), vol. 334, 1081-1086.
Maharjan et al., "Mitochondrial impairment triggers cytosolic oxidative stress and cell death following proteasome inhibition", Sci Rep., (2014), 4:5896, (11 pages).
Starheim et al., "Intracellular glutathione determines bortezomib cytotoxicity in multiple myeloma cells", Blood Cancer J., (2016), vol. 6:e446, (8 pages).
Tsuboi et al., "Potent and selective inhibitors of glutathione S-transferase omega 1 that impair cancer drug resistance", J Am Chem Soc., (2011), vol. 133, pp. 16605-16616.
Ramkumar et al., "Mechanistic evaluation and transcriptional signature of a glutathione S-transferase omega 1 inhibitor", Nat Commun., (2016); 7:13084, (13 pages).
Ianevski et al., "SynergyFinder: a web application for analyzing drug combination dose-response matrix data", Bioinformatics, (2017), vol. 33, No. 15, pp. 2413-2415.
D'Arcy et al., "Inhibition of proteasome deubiquitinating activity as a new cancer therapy", Nat Med., (2011), vol. 17, No. 12, pp. 1636-1640.
Wang et al., "The proteasome deubiquitinase inhibitor VLX1570 shows selectivity for ubiquitin-specific protease-14 and induces apoptosis of multiple myeloma cells", Sci Rep., (2016), 6:26979, (15 pages).
Ri et al., "Bortezomib-resistant myeloma cell lines: a role for mutated PSMB5 in preventing the accumulation of unfolded proteins and fatal ER stress", Leukemia, (2010), vol. 24, pp. 1506-1512.
Robak et al., "Drug resistance in multiple myeloma", Cancer Treat Rev., (2018), vol. 70, pp. 199-208.
Walerych et al., "Proteasome machinery is instrumental in a common gain-of-function program of the p53 missense mutants in cancer", Nat Cell Biol., (2016), vol. 18, No. 8, pp. 897-909.
Ogiwara et al., "Targeting the Vulnerability of Glutathione Metabolism in ARID1A-Deficient Cancers", Cancer Cell., (2019), vol. 35, pp. 177-190.
Anglesio et al., "Type-specific cell line models for type-specific ovarian cancer research", PLoS One, (2013), vol. 8, Issue 9, e72162, (13 pages).

(56) References Cited

OTHER PUBLICATIONS

Strauss et al., "The proteasome inhibitor bortezomib acts independently of p53 and induces cell death via apoptosis and mitotic catastrophe in B-cell lymphoma cell lines", Cancer Res., (2007), vol. 67, No. 6, pp. 2783-2790.

Qin et al., "Proteasome inhibitors trigger NOXA-mediated apoptosis in melanoma and myeloma cells", Cancer Res., (2005), vol. 65, No. 14, pp. 6282-6293.

Liu et al., "Proteostasis regulation at the endoplasmic reticulum: a new perturbation site for targeted cancer therapy", Cell Res., (2011), vol. 21, pp. 867-883.

Luker et al., "Imaging 26S proteasome activity and inhibition in living mice", Nat Med., (2003), vol. 9, No. 7, pp. 969-973.

Lau et al., "Multifactorial mechanisms associated with broad cross-resistance of ovarian carcinoma cells selected by cyanomorpholino doxorubicin", Cancer Res., (1991), vol. 51, pp. 5181-5187.

Bazzaro et al., "alpha,beta-unsaturated carbonyl system of chalcone-based derivatives is responsible for broad inhibition of proteasomal activity and preferential killing of human papilloma virus (HPV) positive cervical cancer cells", J Med Chem., (2011), vol. 54, pp. 449-456.

Anchoori et al., "Stressing the ubiquitin-proteasome system without 20S proteolytic inhibition selectively kills cervical cancer cells", PLoS One, (2011), vol. 6, Issue 8, e23888, (10 pages).

Coughlin et al., "Small-molecule RA-9 inhibits proteasome-associated DUBs and ovarian cancer in vitro and in vivo via exacerbating unfolded protein responses", Clin Cancer Res., (2014), vol. 20, No. 12, pp. 3174-3186.

DeBerardinis et al., "Fundamentals of cancer metabolism", Sci Adv., (2016), vol. 2, :e1600200, (18 pages).

Chen et al., "Enhanced Degradation of Misfolded Proteins Promotes Tumorigenesis", Cell Rep., (2017), vol. 18, pp. 3143-3154.

Bazzaro et al., "Ubiquitin-proteasome system stress sensitizes ovarian cancer to proteasome inhibitor-induced apoptosis", Cancer Res., (2006), vol. 66, No. 7, pp. 3754-3763.

Aghajanian et al., "Phase I trial of bortezomib and carboplatin in recurrent ovarian or primary peritoneal cancer", J Clin Oncol., (2005), vol. 23, No. 25, pp. 5943-5949.

Ramirez et al., "Phase I trial of the proteasome inhibitor bortezomib in combination with carboplatin in patients with platinum- and taxane-resistant ovarian cancer", Gynecol Oncol., (2008), vol. 108, pp. 68-71.

International Search Report and Writen Opinion issued in corresponding International Application No. PCT/US2020/063456 on Mar. 31, 2021.

* cited by examiner

RA190

RA183

RA181C

RA142C

RA338

RA190H

Bortezomib

RA190B

B

C

A

RA190

RA190A

RA371

RA183

RA375

RA304

B

A

RA190 RA371 RA375

B

RA190 RA371 RA375 p = 0.0397

RA413

RA419

RA462

RA467

RA413S

RA413R

RA414

F

G

SMALL MOLECULE RPN13 INHIBITORS WITH ANTITUMOR PROPERTIES

RELATED APPLICATIONS

This application is a U.S. National Stage of PCT/US2020/063456, filed Dec. 4, 2020, which claims priority to U.S. Provisional Patent Application No. 62/944,957, filed Dec. 6, 2019, and U.S. Provisional Patent Application No. 63/057,778, filed Jul. 28, 2020. The entire contents of each is incorporated by reference herein.

GOVERNMENT LICENSE RIGHTS

This invention was made with government support under grant numbers P30 CA006973, P50 CA098252, and P50 CA228991 awarded by the National Institutes of Health. The government has certain rights in the invention.

FIELD OF THE INVENTION

The present invention relates to molecules with Michael acceptors based on a bis-benzylidine piperidone backbone. The molecules can be used as therapeutic agents against various types of cancers. Specifically, these molecules work as proteasome inhibitors and bind to the RPN13 subunit of the 19S regulatory particle (RP), and can optionally possess a methylated piperidone core to impart asymmetry to the molecule.

BACKGROUND

The eukaryotic 26S proteasome is a 2.5 MDa complex of 47 proteins arranged in a symmetrical barrel of two central 20S catalytic subunits (CS) capped at either end by 19S regulatory particles (RP) that act together to mediate targeted degradation of proteins via a coordinated multi-step process. Proteins are targeted for proteasomal degradation by coupling of ubiquitin in extended K48-linked chains via a ubiquitin ligase. Proteins displaying K48-linked ubiquitin chains are first recognized by 19S RP, unfolded and deubiquitinated therein, and subsequently passed on to the catalytic 20S core particle for degradation into small peptides by its three distinct proteolytic active sites (1). Although the proteasome performs key homeostatic cellular functions, targeted inhibition of the 20S proteasome chymotryptic catalytic subunit PSMB5 is used for the treatment of multiple myeloma (MM) and mantle cell lymphoma (MCL), and three such inhibitors have been licensed (bortezomib, ixazomib and carfilzomib).

The efficacy of these three 20S catalytic particle (20S CP)-targeted inhibitors (bortezomib, carfilzomib and ixazomib) against multiple myeloma and mantle cell lymphoma validate the proteasome as a cancer drug target. However, to date, they have failed to demonstrate efficacy against solid tumors, possibly reflecting limited drug assess, and MM and MCL patients frequently develop resistant disease and treatment-related peripheral neuropathy (2, 3). This implies that drug access may be the limiting factor, possibly due to their peptide backbones. Furthermore, known protease inhibitors are associated with dose limiting side effects including peripheral neuropathy, thrombocytopenia, and neutropenia, as well as the eventual emergence of resistance. These limitations have driven drug discovery efforts to target different components of the proteasome with non-peptide inhibitors for the treatment of solid tumors.

Thus, there is considerable interest in addressing the limitations associated with 20S proteasome inhibitors by targeting upstream proteasome activities in the 19S RP including substrate recognition, deubiquitination enzymes (DUBS) and/or ATP-dependent unfolding (4).

SUMMARY OF THE INVENTION

The present invention relates to new ubiquitin-proteasome system inhibitors active against solid cancers by targeting ubiquitin receptor RPN13 within the proteasome's 19S regulatory particle.

Embodiments of the invention include compounds of formula (I):

(I)

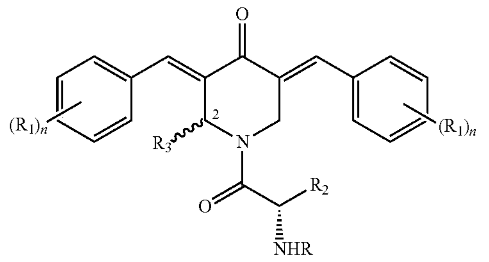

wherein

R is H, $C(O)CH_2Cl$, $C(O)CH_3$, $C(O)CH{=}CH_2$, or $C(O)N(H)CH_3$;

$R_1$ at each occurrence is independently selected from $NO_2$, halogen, and

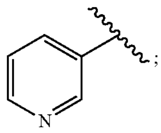 [SMILES: *c1cccnc1]

;

$R_2$ is a side group from an alpha amino acid;

$R_3$ is H, $C_1$-$C_6$ alkyl, or phenyl and n at each occurrence is independently an integer from 0-5, inclusive;

or a pharmaceutically acceptable salt, hydrate, or solvate thereof;

wherein when $R_2$ is the benzyl side group from phenylalanine and $R_3$ is hydrogen, R is $C(O)CH_2Cl$.

A $C_1$-$C_6$ alkyl group represents as a saturated, linear or branched carbon chain having up to 6 carbons. Linear examples include, but are not limited to, methyl, ethyl, and n-propyl. Branched examples include, but are not limited to, isopropyl and t-butyl. In exemplary embodiments $R_3$ is H or methyl (i.e. a $C_1$ alkyl group).

In certain embodiments of the invention, the compound of formula (I) is not

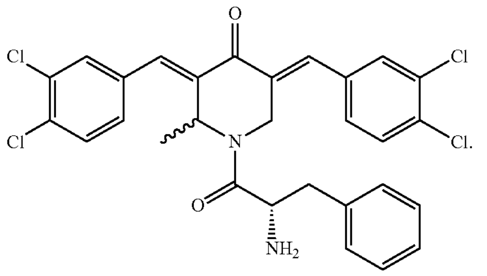 [SMILES: CC1/C(=C\c2ccc(Cl)c(Cl)c2)C(=O)/C(=C/c2ccc(Cl)c(Cl)c2)CN1C(=O)[C@@H](N)Cc1ccccc1]

In certain embodiments $R_2$ is the $(CH_2)_4NH_2$ side group from lysine or the benzyl side group from phenylalanine. In a preferred embodiment $R_2$ is the benzyl side group from phenylalanine. In another preferred embodiment R is C(O) $CH_2Cl$. In certain embodiments, $(R_1)_n$ is preferably 3,4-dichloro, 4-nitro, 2-fluoro or 4-fluoro.

In a preferred embodiment the compound of formula (I) is selected from the group consisting of

RA375

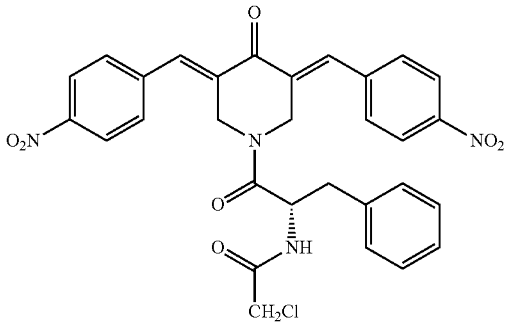

and

RA375

RA371

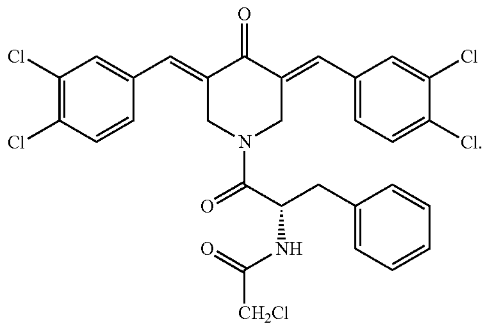

RA317

In certain embodiments $R_3$ is methyl. In a preferred embodiment, R is H or $C(O)CH_2Cl$; $R_1$ is nitro or fluorine; and $R_3$ is methyl. In a preferred embodiment the compound of formula (I) is selected from the group consisting of:

RA413

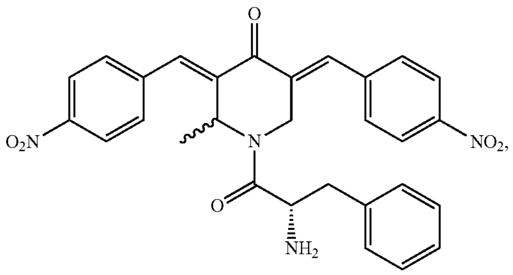

RA414

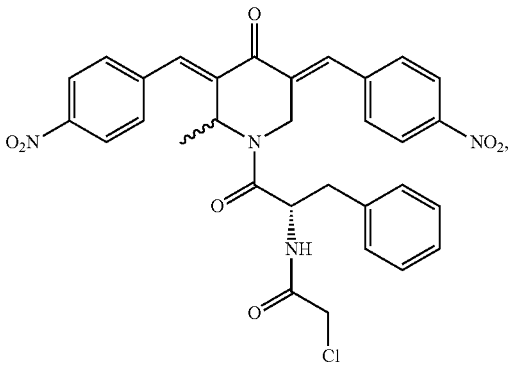

RA462

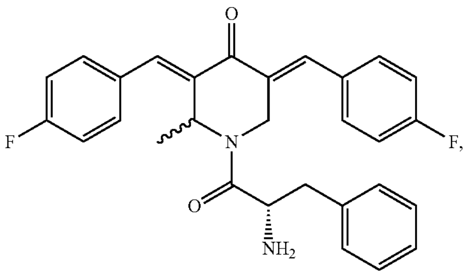

RA467

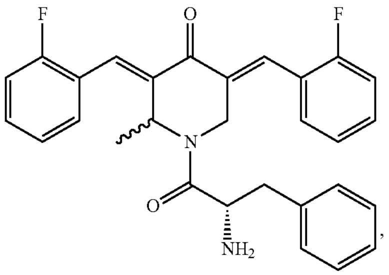

RA413S

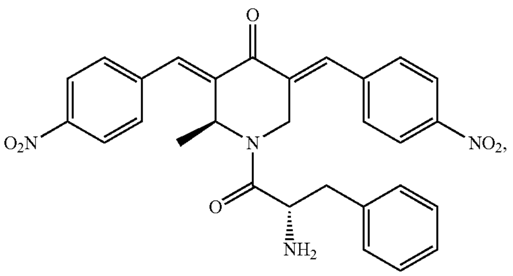

and

-continued

RA413R

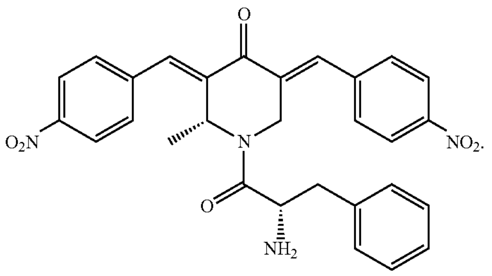

In a preferred embodiment, when $R_3$ is methyl, the configuration at Carbon 2 of formula (I) is the R configuration, S configuration, or a substantially equimolar mixture of R and S. Preferably the configuration at Carbon 2 is the S configuration.

Another embodiment of the invention includes compounds of formula (II):

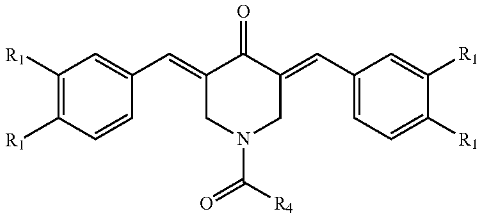

wherein $R_1$ at each occurrence is independently selected from H, $NO_2$, halogen, and

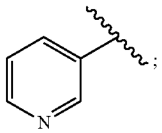 [SMILES: *c1cccnc1]

R4 is

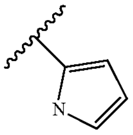

or

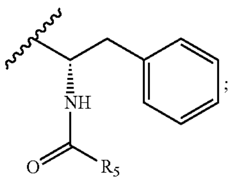

wherein $R_5$ is $CH_2Cl$, $CF_3$

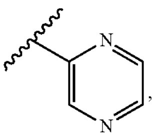

-continued

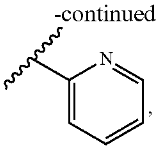

or

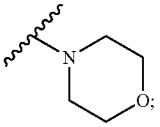

or a pharmaceutically acceptable salt, solvate, or hydrate thereof.

In certain embodiments of formula (II), when $R_1$ at each occurrence is chlorine, then $R_5$ is not $CF_3$ or

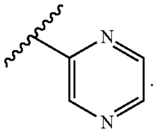 [SMILES: *c1cnccn1]

Another embodiment of the invention includes compounds of formula (III)

(III)

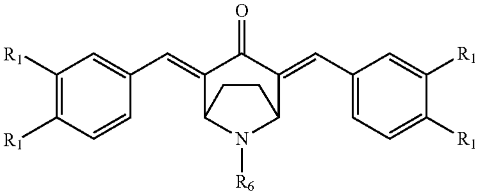

wherein $R_1$ at each occurrence is independently selected from H, $NO_2$, halogen, and

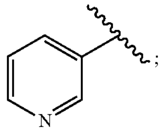 [SMILES: *c1cccnc1]

and $R_6$ is H, $C(O)CH_3$, $C(O)CH{=}CH_2$,

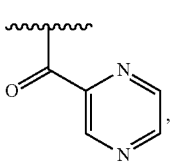

or

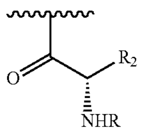

wherein R is H, $C(O)CH_2Cl$, $C(O)CH_3$, $C(O)CH{=}CH_2$, or $C(O)N(H)CH_3$, and $R_2$ is a side group from an alpha amino acid, or a pharmaceutically acceptable salt, solvate, or hydrate thereof.

In certain embodiments of formula (II), when $R_1$ at each occurrence is chlorine, then R is not H.

Any compound of Formula (I), (II), or (III) may be in the form of a hydrate, salt or solvate. The salts may be, for example, hydrogen chloride salts or sulfate salts.

Embodiments of the invention also include a method of inhibiting proteasomes in a mammal by administering an effective amount of any compound of Formula (I), (II), or (III) to the mammal. Embodiments of the invention also include a method of treating a condition or a disease in a mammal by administering to the mammal a therapeutically effective dose of any compound of Formula (I), (II), or (III) to the mammal. In embodiments, the mammal is a human. In some embodiments, the condition or disease is a type of cancer. The type of cancer may be, for example, cervical cancer, ovarian cancer, multiple myeloma, breast cancer, or pancreatic cancer. In some embodiments, the type of cancer is associated with Human Papilloma virus (HPV). In a preferred embodiment, the cancer is ovarian cancer. Methods of the invention can also include administering any compound of Formula (I), (II), or (III) in combination with at least one other therapeutic agent. In embodiments, the at least one other therapeutic agent is a proteasome inhibitor. In some embodiments, the at least one other therapeutic agent is bortezomib. In embodiments, at the least one other therapeutic agent is a DNA damaging agent. In some embodiments, the at least one other therapeutic agent is cisplatin. In some embodiments, the at least one other therapeutic agent is cisplatin. In a preferred embodiment, the compound is RA414 or RA413 S, and the DNA damaging agent is cisplatin.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

FIG. 1A illustrates chemical structures of candidate inhibitors RA190, RA181, RA181C, RA142C, RA338, RA190H, and RA190B.

FIG. 1B illustrates precleared ES2 cell lysate incubated with compounds (20 μM) or vehicle (DMSO, 1:100) for 45 min and then with RA190B (5 μM) for 45 min at 4° C. by Western blot analysis. Samples were subjected to SDS-PAGE, transfer to PVDF membrane, and after probing with HRP-streptavidin, binding was detected using chemiluminescence.

FIG. 1C illustrates ES2 cells treated with compounds (1 μM, 4 hr), lysed and the samples probed with ubiquitin or actin-specific antibody by Western blot analysis.

FIG. 2A illustrates the Pharmacophore denoted. R, R1, and R2 are modification sites to potentially alter the molecule's physical and chemical properties while retaining the mechanism of action. Modifications at the grey dots may allow the molecule to orient in one of four possible confirmations of cyclohexanone.

FIG. 2B illustrates precleared OV2008 cell lysate incubated with compounds (20 μM) or vehicle (DMSO, 1:100) for 45 min and then with RA190B (10 μM) for 45 min at 4° C. by Western blot analysis. Samples were subjected to SDS-PAGE, transfer to PVDF membrane, and binding of HRP-streptavidin, detected using chemiluminescence.

FIG. 3A illustrates the alkyne moiety of KT59 reacted with fluorescent azide reporter via click chemistry to reveal inhibitor-labeled proteins. SKOV3 cell lysate was treated with 10 μM of KT59 for 30 min at 25° C. For competition with RA190 and RA375, lysate was first treated with RA190 or RA375 at indicated concentrations for 45 min at 4° C. by Western blot analysis prior to addition of KT59 (10 μm, 30 min). Cell lysate was boiled in Laemmli buffer and separated by SDS-PAGE, and transferred to PVDF membrane. Next the membrane was treated with Alexa Fluor 488 azide (5 μL, Cat. No. A10266, Life Technologies) for 45 min at room temperature in the presence of CuSO4 (10 μL of 10 mM stock) and sodium ascorbate (20 μL of 20 mM stock) in PBST (10 mL). The membrane was washed with PBST (3 times for 20 min) and blocked with 1% BSA for 1 hr and then probed with antibody for Alexa488 (Rabbit polyclonal, Life Technologies, Cat No. A-11094) in 1% BSA in PBST for 1 hr. The membrane was washed with PBST for 3 times and incubated with secondary antibody in PBST for 1 hr and washed with PBST (3× for 20 min) and developed using chemiluminescence reagent by Biorad Imager.

FIG. 3B illustrates multiple myeloma cell line RPMI8226 and its bortezomib resistant version (RPMI-8226-V10R) treated with either DMSO or RA375 for 48 hr and the cell viability was compared using MTT.

FIG. 3C illustrates multiple myeloma cell line RPMI8226 and its bortezomib resistant version (RPMI-8226-V10R) treated with either DMSO or bortezomib (FIG. 3C) for 48 hr and the cell viability was compared using MTT.

FIG. 3D illustrates ovarian cancer cell line SKOV3 and its paclitaxel resistant version (SKOV3-TR) treated with either DMSO or RA375 for 48 hr and the cell viability was assayed using MTT.

FIG. 3E illustrates ovarian cancer cell line SKOV3 and its paclitaxel resistant version (SKOV3-TR) treated with either DMSO or paclitaxel for 48 hr and the cell viability was assayed using MTT.

FIG. 3F illustrates a panel of cell lines derived from HPV positive and negative cervical cancers as well as head and neck cancers that were treated with RA375 for 48 hr and the cell viability was compared using MTT.

FIG. 4A illustrates HS578T cells plated at 300/well in mL DMEM growth medium in a 6 well plate and incubated at 37° C. for a day.

FIG. 4B illustrates SKOV3 cells plated at 300/well in 2 mL DMEM growth medium in a 6 well plate and incubated at 37° C. for a day.

FIG. 4C illustrates SKOV3 cells grown in 10% FCS/DMEM medium lacking methionine and cysteine which were compared with cells grown in standard DMEM for 48 hr in the presence of RA190. Cell viability was measured using an MTT assay.

FIG. 4D illustrates SKOV3 cells grown in 10% FCS/DMEM medium lacking methionine and cysteine which were compared with cells grown in standard DMEM for 48 hr in the presence of RA371. Cell viability was measured using an MTT assay.

FIG. 4E illustrates SKOV3 cells grown in 10% FCS/DMEM medium lacking methionine and cysteine which were compared with cells grown in standard DMEM for 48 hr in the presence of RA375. Cell viability was measured using an MTT assay.

FIG. 6A illustrates SKOV3 cells (2500 cells/well) seeded in triplicate in a 96 well plate and treated one day later with RA375 or RA190 in the presence or absence of GSH (1 mM). Cell viability was measured after 24 hrs using an MTT assay. Significance versus DMSO control (ns=not significant, * <0.001, ** <0.0001).

FIG. 6B illustrates SKOV3 cells (250,000/well) treated in triplicate with DMSO vehicle alone or 0.5 μM of RA375, RA190, or bortezomib (Bz) for 12 hr and the total GSH was measured. Cell viability was measured after 24 hrs using an MTT assay. Significance versus DMSO control (ns=not significant, * <0.001, ** <0.0001).

FIG. 7A illustrates ES2 cells (250,000 cells/well) treated with compounds at 1 μM for 12 hr and mRNA was isolated. Samples were subjected to RT-qPCR to measure CHOP10 and mRNA levels normalized to GAPDH expression. Significance versus DMSO control (ns=not significant,  <0.01, * <0.001, **** <0.0001).

FIG. 7B illustrates ES2 cells (250,000 cells/well) treated with compounds at 1 μM for 12 hr and mRNA was isolated. Samples were subjected to RT-qPCR to measure XBP-1s and mRNA levels normalized to GAPDH expression. Significance versus DMSO control (ns=not significant,  <0.01, * <0.001, **** <0.0001).

FIG. 7C illustrates ES2 cells (250,000 cells/well) treated with compounds at 1 μM for 12 hr and incubated with $H_2$DCFDA (20 μM) for 30 min and analyzed by flow cytometry. $H_2O_2$ was used as a positive control.

FIG. 7D illustrates surface PS staining of $10^5$ ES2 cells treated with compounds for 12 hr and re-suspended in binding buffer and labeled with Annexin V-PE and 7-AAD at RT for 15 min and analyzed by flow cytometry (Becton Dickinson, Mountain View, CA).

FIG. 7E illustrates ES2 cells treated with either vehicle or compounds (1 μM, 18 hr) which were fixed and probed with anti-Caspase 3 antibody and analyzed by flow cytometry.

FIG. 8A illustrates SKOV3 cells treated for 12 hr with compounds (or as a positive control, $H_2O_2$) at the indicated doses and ROS levels were measured by adding Amplex Red and HRP.

FIG. 8B illustrates $10^5$ SKOV3 cells treated with compounds (1 μM, 12 hr), then re-suspended in 100 μL binding buffer with 5 μL of Annexin V-PE and 5 μL of 7-AAD to analyze apoptosis. After a 15 min incubation at RT, the cells were analyzed by flow cytometry using a FACSCalibur and CellQuest software (Becton Dickinson).

FIG. 9A illustrates 293T cells in 96 well plates transiently transected with the 4UbFL plasmid and 48 hr later treated with the indicated doses of each compound for 4 hr. Cells were lysed and luciferase activity assessed using a luminometer.

FIG. 9B illustrates BALB/c mice electroporated with 4UbFL plasmid (10 μg/mouse) in the leg muscle and the basal luminescence was recorded after 48 hr. Groups of mice (n=5) were treated with different compound (40 mg/Kg) or vehicle alone (25% (w/v) β-Hydroxypropylcyclodextrin in water). Mice were imaged for bioluminiscence activity using IVIS instrument at 4, 24, 48, 72 and 96 hr.

FIG. 9C illustrates nude mice (8 per group) inoculated with $10^6$ ES2-luc cells i.p. in 100 μL PBS. Three days later the mice were imaged for basal level (day 0) bioluminescence expression using an IVIS200.

FIG. 9D illustrates mice were randomized into two groups (n=8) and treated daily i.p. with RA375 (10 mg/Kg) or vehicle (25% (w/v) β-Hydroxypropylcyclodextrin) for a 5 days on, 2 days off cycle for two weeks and imaged again on day 7 and day 14 for tumor burden.

FIG. 13A illustrates SKOV3 cell lysate pretreated with RA413S at indicated concentrations and labelled with RA183B.

FIG. 13B illustrates ES2 cell lysate treated with biotinylated compound RA413SB and RA183B.

FIG. 13C illustrates SKOV3 cell lysate pretreated with RA414 at various concentrations and labelled with RA183B.

FIG. 13D illustrates a structural view of the RPN13 Pm Domain complex docked with RA413S, RA183 and RA414.

FIG. 13E illustrates a ligand interaction diagram for RA183.

FIG. 13F illustrates a ligand interaction diagram for RA413S.

FIG. 13G illustrates a ligand interaction diagram for RA414.

FIG. 14A illustrates SKOV3 cells treated with compounds for 4 h and analyzed by Western blot analysis with antibody to ubiquitin.

FIG. 14B illustrates fold increase in bioluminiscence of ES2 cells stably expressing 4UbFL at 4 hrs post-treatment of compounds, as measured by luminometer.

FIG. 14C. illustrates IVIS200 imaging showing the fold increase in bioluminescence of female CD1 mice leg muscle before (0 hr) and after treatment (4, 24, 48, and 72 hr). Leg muscle was electroporated with 4UbFL plasmid and increased bioluminescence was observed after treatment with RA413S; $1^{st}$ Dose (PEG formulation); $2^{nd}$ dose (b-HPCD formulation).

FIG. 14D. illustrates IVIS200 imaging showing the individual mice bioluminescence units of female CD1 mice leg muscle before (0 hr) and after treatment (4, 24, 48, and 72 hr). Leg muscle was electroporated with 4UbFL plasmid and increased bioluminescence was observed after treatment with RA414 or bortezomib.

FIG. 15A illustrates fluorescent microscopy images of HeLa cells treated with RA413S for 18 hrs at indicated concentrations.

FIG. 15B illustrates fluorescent microscopy images of BR5 cells treated with RA413S for 18 hrs at indicated concentrations.

FIG. 15C illustrates bioluminescence of ES2 cells expressing firefly luciferase.

FIG. 15D illustrates RA413S treatment for 12 hr significantly decreases overall oxygen consumption in the Seahorse mitochondrial stress test.

FIG. 15E illustrates RA413S treatment for 12 hr significantly decreases basal respiration rate in the Seahorse mitochondrial stress test.

FIG. 15F illustrates proton leak of ES2 cells treated with RA413S relative to vehicle or RA414-treated groups.

FIG. 15G illustrates maximal respiration was significantly reduced in ES2 cells treated with RA413S relative to the vehicle or RA414-treated groups.

FIG. 15H illustrates RA413S significantly reduces cellular energy reserves in ES2 cells.

FIG. 15I illustrates a 4-fold decrease in ATP production 12 hr after RA413S treatment.

FIG. 15J illustrates downregulation of intracellular pH change (ECAR) 24 h after RA413S treatment.

FIG. 16A illustrates ES2 cells treated with compounds (0.5 μM) for 12 hr and CHOP-10 mRNA levels, an ER stress marker, which was analyzed by qRT-PCR.

FIG. 16B illustrates ES2 cells treated with compounds for 12 hr and the total GSH level assayed.

FIG. 16C illustrates ES2 cells treated for 12 hr with compounds (or as a positive control, $H_2O_2$) at the indicated doses, and then reactive oxygen species (i.e. ROS) levels measured by adding Amplex Red and HRP.

FIG. 16D illustrates ES2 cells were treated with compounds at indicated doses for 12 hr then re-suspended in 100 μL binding buffer with 5 μL of Annexin V-PE and 5 μL of 7-AAD to examine early apoptosis. After a 15 min incubation at RT, the cells were analyzed by flow cytometry using a FACSCalibur and CellQuest software.

FIG. 17A illustrates C57BL/6 mice bearing ID8-VegfDefb2 tumor intraperitoneally imaged at indicated days either with vehicle or RA414 (10 mg/Kg/every 3 days/3 doses total) and RA414 (3 mg/Kg/every 3 days/total 9 doses) and imaged using IVIS200.

FIG. 17B illustrates two mice (from FIG. 17A) each from the vehicle and RA414 (3 mg/Kg) treated mice which were euthanized after collecting ascites at day 24. The ascites cells were lysed and the lysates subjected to Western blot analysis using antibody to ubiquitin or actin used as a loading control.

FIG. 18A illustrates C57BL/6 mice administered ID8-VegfDefb29 in a syngeneic mouse model of ovarian cancer expressing luciferase (62) intraperitoneally imaged before treatment (day 3 post tumor inoculation). Treatment was initiated on day 3 and the mice were imaged again after treatment with either vehicle or RA413S (15 mg/Kg/every 3 days/total 5 doses) on day 17.

FIG. 18B illustrates bioluminescence expressed by tumor cells quantified by IVIS200. A significant difference in bioluminescence was observed $p<0.0001$.

FIG. 19A illustrates female nude mice bearing ES2 tumor expressing firefly luciferase imaged before and after treatments either with vehicle (n=7) or RA413S (n=7, 10 mg/Kg/every 3 days/12 doses total) and imaged using IVIS200 for the bioluminescence expressed by the tumors. One mouse in the vehicle group died on day 12 and was not included for the day 12 and 21 time points.

FIG. 19B illustrates the Kaplan-Meier survival curve and logrank analysis demonstrating nude mice treated with RA413S have increased survival rate compared to the vehicle treated mice ($p<0.001$). RA413S was dissolved in 25% b-hydroxypropyl cyclodextrin in water.

FIG. 20A illustrates a model of the proposed mechanisms underlying synergistic cytotoxicity of RA414 and cisplatin treatment.

FIG. 20B illustrates OVCAR3 cells treated with RA414 and Cisplatin titrated in a checker-board assay and the synergy calculations were done using the Synergy Finder web application.

FIG. 21A illustrates HeLa cells treated with compounds (0.5 μM, 3 hr).

FIG. 21B illustrates HCT116 cells treated with compounds (0.5 μM, 3 hr).

FIG. 21C illustrates 293T cells stably expressing NF-κB dependent luciferase gene that show a dose dependent reduction in bioluminescence with drug treatment (7 hr) measured by luminometer.

DETAILED DESCRIPTION OF THE INVENTION

Figure 1:
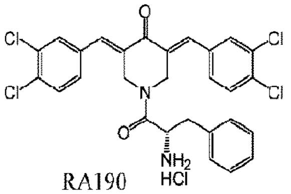
FIG. 1 illustrates experiments probing requirements to bind a 42 kDa cellular target and accumulate high molecular weight polyubiquitinated proteins.
Figure 1:
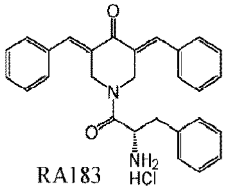
Figure 1:
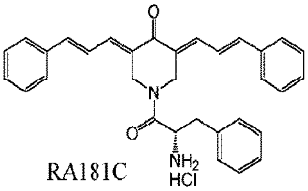
Figure 1:
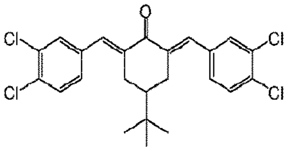
Figure 1:
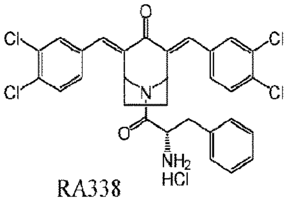
Figure 1:
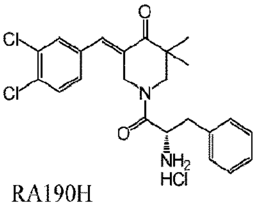
Figure 1:
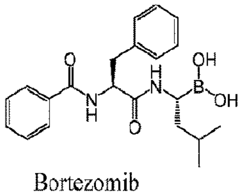
Figure 1:
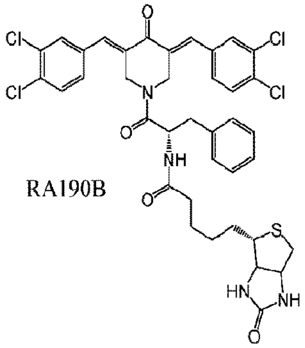
Figure 1:
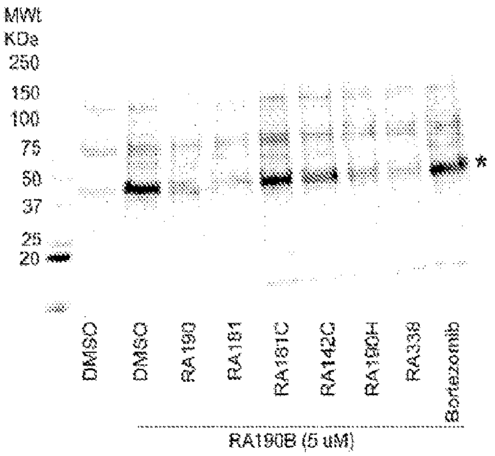
Figure 1:
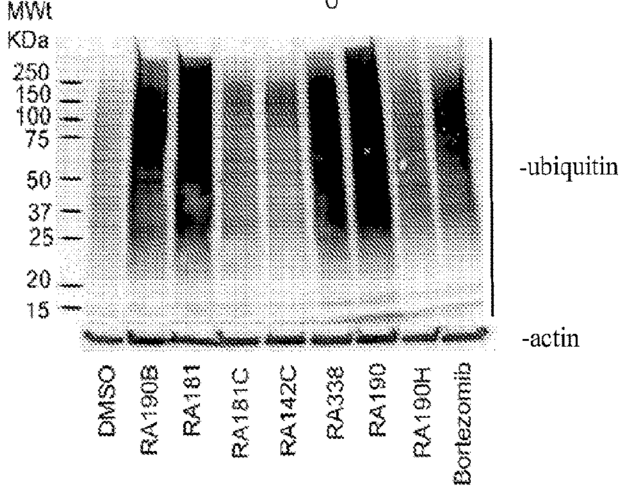

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustrative purposes only. A person skilled in the relevant art will recognize that other components and configurations can be used without parting from the spirit and scope of the invention. All references cited herein are incorporated by reference as if each had been individually incorporated.

Two ubiquitin receptors, RPN13 and RPN10, in the 19S RP act in concert to recognize protein substrates tagged with K48-linked chains of ≥4 ubiquitin subunits. In addition to its ubiquitin binding Pru N-terminal domain (5), RPN13 also binds the deubiquitinase (DUB) UCH37/UCHL5, and RPN2 recruiting it to the 19S RP (6, 7). RPN13 interaction also enhances the DUB activity of UCH37, likely by opening up its active site (8, 9). This DUB activity allows recycling of the ubiquitin subunits and, after ATP-dependent unfolding, progression of the substrate to the 20S catalytic subunit for degradation.

The 19S RP inhibitors b-AP15 (31) and the more potent analog VLX1570 (72) covalently bind to active site cysteine residues of two 19S RP proteins, ubiquitin-specific protease 14 (USP14) and ubiquitin C-terminal hydrolase 37 (UCH37), and possess significant antitumor properties in animal models of solid cancers. Mice lacking USP14 are viable but exhibit neuromuscular disease (73). However, UCH37 deficiency causes embryonic lethality (61) raising concerns for drug safety. Extended selection of cells in b-AP15 produced only very limited drug resistance (~2-fold). This was reversed by buthionine sulphoximine, implying altered glutathione (GSH) metabolism as a resistance mechanism, whereas drug uptake and overexpression of drug efflux transporters did not contribute to b-AP15 resistance (67). VLX1570 advanced into phase I in patients with relapsed and/or refractory multiple myeloma (70). While anti-myeloma effects were observed at ≥0.6 mg/kg, two patients treated at the 1.2 mg/kg dose level experienced severe, abrupt, and progressive respiratory insufficiency, culminating in death.

RA190 was identified in U.S. Pat. No. 9,913,834, which is incorporated by reference in its entirety, as an RPN13 inhibitor that blocks proteasome-mediated deubiquitination and proteolysis (6). Although binding to UCH37 can also occur in vitro (6), several lines of evidence including cell labeling (10), degrader (11) and knockout studies (12) suggest that RPN13 is RA190's principle cellular target. RA190 and the related RA183 (13) exhibit antineoplastic activity, including against bortezomib-resistant MM, and against solid tumors in pre-clinical models of ovarian cancer (10, 13, 14), human papillomavirus (HPV)-associated and several other solid cancers (6, 12, 15-18). Like RA190 and RA183 (13), the diphenyldihaloketones CLEFMA and EF-24 also adduct to RPN13 and inhibit proteasome function (19), and the pharmacophore has been further investigated herein.

The small molecule RA190 (10), a prototypic inhibitor of RPN13, and its more potent analog RA183 (13), the structures of which are shown below, were thought to offer a promising approach for treatment of ovarian cancer:

RA190

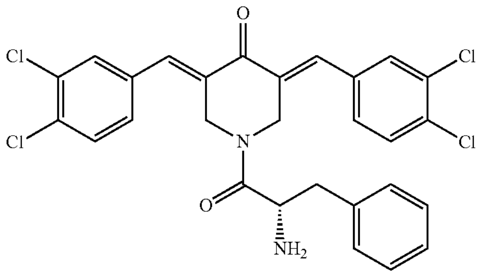

RA183

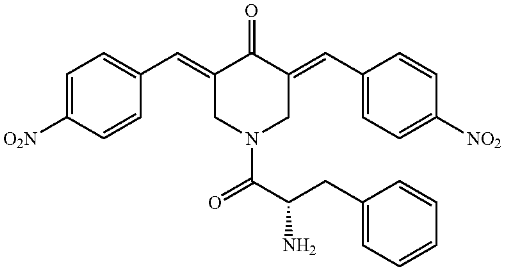

Each of these molecules adducts RPN13 Cysteine 88 that resides within a groove required for binding of RPN13 to the proteasome via RPN2. However, in cytotoxicity assays, these RPN13 inhibitors (iRPN13) are not as potent as bortezomib based upon their IC50 against cancer cell lines. GSH metabolism counteracts the cytotoxic effects of RA190 and RA183. There thus remains a need for small molecule RPN13 inhibitors useful as anti-cancer agents. It has been found that addition of a chloroacetamide moiety to these compounds, resulting in RA371 and RA375, respectively (see Table 1), enhanced their potency, presumably by reacting with, and thereby reducing intracellular GSH and its competition for binding to RPN13.

Ovarian cancer is a promising target for these molecules because RPN13, which is encoded by ADRM1, is consistently over-expressed in high grade serous carcinoma, and this occurs in the precursor lesion (17). Amplification of ADRM1 is most common in ovarian cancer and is associated with shorter time to recurrence and overall survival (20, 21), although it does not predict sensitivity to RA190 in cell lines (17). Ectopic ADRM1 overexpression in cell lines increases proliferation, migration, and growth in soft agar, and knock-down of ADRM1 expression results in apoptosis, and it has been suggested as an oncogene and novel therapeutic target for ovarian cancer (21). Further, RPN13 knockout mice are viable (61), suggesting it may be a safer drug target.

Chronic accumulation of misfolded polyubiquitinated proteins is associated with ovarian cancer, and it is exacerbated by proteasome inhibition (22, 23). The Unfolded Protein Response (UPR) is triggered in an effort to restore proteostasis and relieve endoplasmic reticulum stress and, if unresolved, leads to p53-independent apoptosis (24, 25). Elevated generation of intracellular reactive oxygen species (ROS) is frequently associated with malignant transformation due to oncogene activation and/or enhanced metabolism in tumor cells and confers oxidative injury. This potentially provides a therapeutic window and treatment with proteasome inhibitor bortezomib rapidly induces oxidative stress that is considered a major contributor to its anticancer properties (26, 27).

Because of the potential for competition with, or inactivation by, cellular glutathione, incorporation of alternative warheads, including chloroacetamide, intended to lower cellular glutathione levels (28, 29) were tested, thereby limiting inactivation of the chalcone-based RPN13 inhibitors and increasing oxidative stress and their antitumor potency.

In seeking compounds with higher potency and specificity towards RPN13, analogs of RA190 and RA183 were designed using molecular modeling and knowledge of its pharmacophore. The addition of a methyl group to the core piperidone moiety was examined. Introduction of the methyl group at the C2 position adds an additional chiral center and renders the compound asymmetric. It was thought this may impact specificity towards its target due to the structural hindrance, or the metabolite profile because of the electron releasing inductive effect of the methyl group. Therefore, the potency of stereoisomers of RA413, a chiral RPN13 analog, were compared. It was discovered that the potency of the S-isomer at the C2 position was 2-6 fold more active than the R-isomer (referred to as RA413S and RA413R, respectively). Surprisingly the 'S' isomer, RA413S, turned out to be 4 fold more active then 'R' isomer, RA413R, which indicates the importance of spacial-confirmation of the molecule towards the specificity and potency.

The mechanism of action of RA413S and its associated rapid cancer cell death in vitro and anti-tumor effect in mice were investigated. In particular, the ability of RA413S to induce mitophagy, deplete mitochondrial ATP production and glycolysis in ovarian cancer thereby promoting the rapid cell death, were investigated. The data obtained helps to determine the effect of RPN13 inhibition on the mitochondrial parkin function which is responsible for the degradation of defective mitochondria through mitophagy. Loss of function of RPN13 results in accumulated defective mitochondria and its aggregated proteins and ultimately leads to ATP depletion and cancer cell death.

The prototypic bis-benzylidine piperidone-based inhibitor RA190 is a Michael acceptor that adducts Cysteine 88 of RPN13. Probing the pharmacophore has shown the benefit of the central nitrogen-bearing piperidone ring moiety compared to a cyclohexanone, the importance of the span of the aromatic wings from the central enone-piperidone ring, the contribution of both wings, and that substituents with stronger electron withdrawing groups were more cytotoxic. Potency was further enhanced by coupling of a second warhead to the central nitrogen-bearing piperidone as RA375 (see Table 1) which exhibited ten-fold greater activity against cancer lines than RA190, reflecting its nitro ring substituents and the addition of a chloroacetamide warhead. Treatment with RA375 caused a rapid and profound accumulation of high molecular weight polyubiquitinated proteins and reduced intracellular glutathione levels, which produce endoplasmic reticulum and oxidative stress, and trigger apoptosis. RA375 was highly active against cell lines of multiple myeloma and diverse solid cancers and demonstrated a wide therapeutic window against normal cells. For cervical and head and neck cancer cell lines, those associated with human papillomavirus were significantly more sensitive to RA375. While ARID1A-deficiency also enhanced sensitivity 4-fold, RA375 was active against all ovarian cancer cell lines tested. RA375 inhibited proteasome function in muscle for >72h after single i.p. administration to mice, and treatment reduced tumor burden and extended survival in mice carrying an orthotopic human xenograft derived from a clear cell ovarian carcinoma.

Accordingly, the present invention provides insight into structural variations which can individually and collectively improve drug binding to RPN13, presumably by adducting Cys-88 (6, 12, 13), and informs design of molecules more potent than the prototype RA190 (10). The flexibility of the core unit allows numerous modifications around the pharmacophore without disturbing target specificity. Building upon previous findings with the RA-chemical series (10, 13, 43-45), and related inhibitors (19), useful structure-activity relationships and analogs with a second warhead (RA371 and RA375) have been identified as having increased potency. It is noteworthy that the related RPN13 inhibitors CLEFMA and EF24 have also demonstrated therapeutic activity against preclinical cancer models via related mechanisms (19).

Cancer cells critically differ from normal cells in higher metabolic rate, ROS and aberrant protein synthesis (46, 47). Proteasomes play a pivotal role managing this excessive metabolism and maintaining protein homeostasis, as the continued over-accumulation of mis-folded proteins is toxic to cells via UPR-induced apoptosis, thereby providing a therapeutic window for proteasome inhibitors (47). Several proteasome inhibitors have proven efficacious against hematologic malignancies, although failure later due to resistance, significant neurological side effects, and inactivity against solid tumors remain challenges. The PSMBS-targeted proteasome inhibitors are developed from polypeptide backbones or large natural compounds that may not readily enter solid tumors. Indeed, bortezomib exhibited limited activity against s.c. ES2 xenografts (48) and in patients against ovarian cancer (49-55) suggesting the need for proteasome inhibitors with a different backbone that better access solid tumor tissues.

Prior proteasome inhibitors each target one of the three proteolytic functions located in the 20S catalytic subunit, the chymotrypic activity of PSMB5. This redundancy of proteasome inhibition function may also explain how these proteasome inhibitors are tolerated by normal cells and the host. The two receptors, RPN10 and RPN13, on the 19S RP co-operate in recognizing ubiquitinated proteins that are targeted for degradation (56). In mice, liver-specific deletion of either RPN10 or RPN13 produced limited effects, but simultaneous loss of both RPN10 and RPN13 caused severe liver injury accompanied by massive accumulation of ubiquitin conjugates (57). This is consistent with cooperative roles of RPN10 and RPN13, and therefore some redundancy, in ubiquitin recognition of the proteasome. Furthermore, several additional ubiquitin receptors have been described for the 19S RP, such as DSS1 and RAD23A/B, also suggesting considerable redundancy (56). Likewise, while RPN13 promotes UCH37 activity, an additional DUB enzyme USP14 also plays an important role in deubiquitinating substrate proteins, thus potentially explaining the tolerability of systemic administration of RPN13 inhibitors. RPN13 was identified as a target of RA190 by adding a biotin tag for labeling studies (RA190B), but this strategy is not available for RA371 and RA375 without compromising the pharmacophore. However, the compounds compete RA190B binding to RPN13 in cell lysates.

RPN13 is an unusual proteasome component in that under normal conditions a single molecule binds to either one end or the other of the proteasome to direct the asymmetric degradation of a polyubiquitinated substrate rather than simultaneous processing from both ends (58). Since RPN13 is over expressed in cancer (17), Kisselev has hypothesized that the covalent RA inhibitors block both ends of the proteasome, whereas in normal cells only one end is blocked and the other can utilize alternative ubiquitin receptors to maintain some proteasome function (14). However, recent structural data suggest that these RA inhibitors act to prevent RPN2 binding and thus association with the 19S RP (4, 59).

The ubiquitin chain topology determines how ubiquitination establishes precise communication in cells. While K48-linked ubiquitinated proteins are tagged for degradation, K63, K33 and K11 linked proteins are tagged for cell cycle maintenance and activation/in-activation of signaling pathways and DNA damage repair (56). While the RA compounds caused accumulation of K48-linked substrates, this was not the case for K63-linked polyubquitinated proteins (not shown).

RA375 has emerged as a compound with excellent pharmacodynamics and reduction of tumor burden and prolongation of the survival of mice carrying an orthotopic human ovarian cancer xenograft. Since bortezomib has not proven effective against ovarian and other solid cancers, further exploration of this new class of RPN13 inhibitors, potentially in combination with doxorubicin, is warranted because of their novel mechanism of action.

To further elucidate the pharmacophore and minimal structural features necessary for RPN13 binding and antineoplastic activity, a new series of compounds based upon bis-benzylidine ring moieties with various modifications in and around the ring were synthetized Table 1 shows the IC50 of a number of compounds of the invention, as well as prior compounds, against HeLa and SKOV3 cells.

TABLE 1

$IC_{50}$ of compounds 1-57 against HeLa and SKOV3 cells.

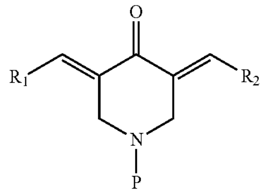

| S. No | Code | R1 | R2 | P | HeLa (nM) | SKOV3 (nM) |
|---|---|---|---|---|---|---|
| 1 | RA7 | 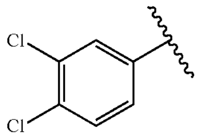 [SMILES: *c1ccc(Cl)c(Cl)c1] | 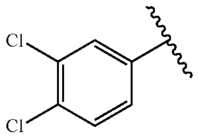 [SMILES: *c1ccc(Cl)c(Cl)c1] | H | 532 | 654 |
| 2 | RA190 | 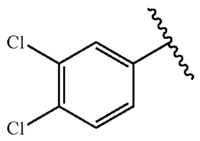 [SMILES: *c1ccc(Cl)c(Cl)c1] | 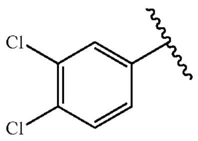 | 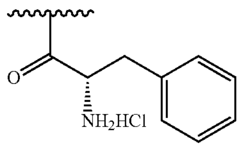 | 85 | 75 |
| 3 | RA190 ACR | 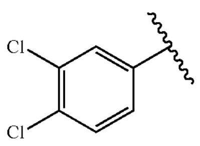 [SMILES: *c1ccc(Cl)c(Cl)c1] | 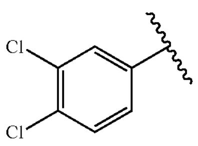 [SMILES: *c1ccc(Cl)c(Cl)c1] | 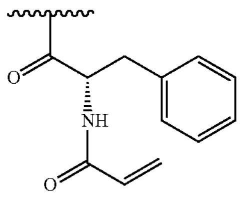 [SMILES: *C(=O)[C@H](Cc1ccccc1)NC(=O)C=C] | 42 | 62 |

TABLE 1-continued
IC$_{50}$ of compounds 1-57 against HeLa and SKOV3 cells.
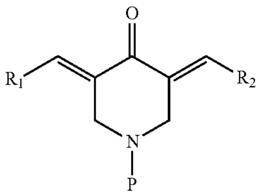
| S. No | Code | R1 | R2 | P | HeLa (nM) | SKOV3 (nM) |
|---|---|---|---|---|---|---|
| 4 | RA190Ac | 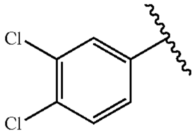 [SMILES: *c1ccc(Cl)c(Cl)c1] | 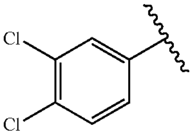 [SMILES: *c1ccc(Cl)c(Cl)c1] | 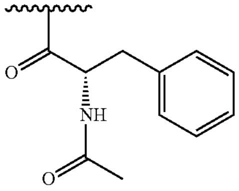 [SMILES: *C(=O)[C@H](Cc1ccccc1)NC(C)=O] | 46 | 68 |
| 5 | RA190P | 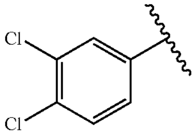 [SMILES: *c1ccc(Cl)c(Cl)c1] | 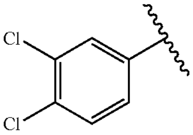 [SMILES: *c1ccc(Cl)c(Cl)c1] | 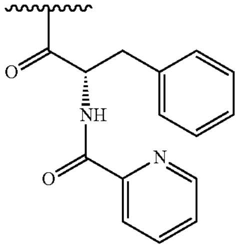 [SMILES: *C(=O)[C@H](Cc1ccccc1)NC(=O)c1ccccn1] | 55 | 64 |
| 6 | RA190SA | 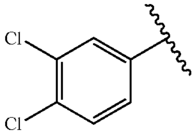 [SMILES: *c1ccc(Cl)c(Cl)c1] | 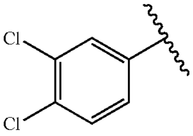 [SMILES: *c1ccc(Cl)c(Cl)c1] | 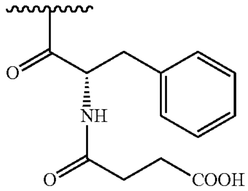 [SMILES: *C(=O)[C@H](Cc1ccccc1)NC(=O)CCC(=O)O] | 121 | 253 |
| 7 | RA190NMS | 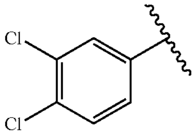 [SMILES: *c1ccc(Cl)c(Cl)c1] | 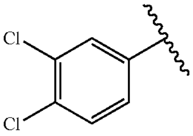 [SMILES: *c1ccc(Cl)c(Cl)c1] | 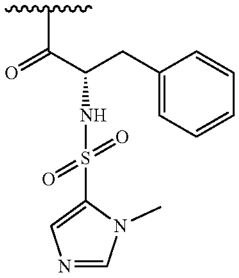 [SMILES: *C(=O)[C@H](Cc1ccccc1)NS(=O)(=O)c1cncn1C] | 78 | 94 |
| 8 | RA190IAS | 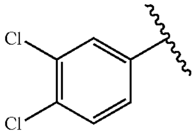 [SMILES: *c1ccc(Cl)c(Cl)c1] | 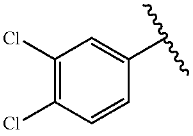 [SMILES: *c1ccc(Cl)c(Cl)c1] | 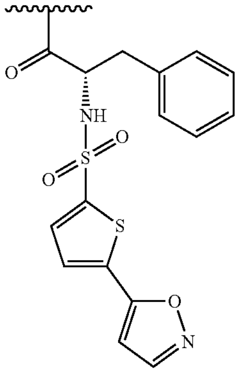 [SMILES: *C(=O)[C@H](Cc1ccccc1)NS(=O)(=O)c1ccc(-c2ccno2)s1] | 211 | 342 |

TABLE 1-continued
IC$_{50}$ of compounds 1-57 against HeLa and SKOV3 cells.
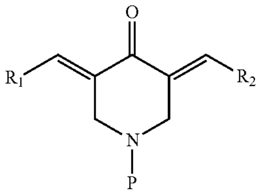
| S. No | Code | R1 | R2 | P | HeLa (nM) | SKOV3 (nM) |
|---|---|---|---|---|---|---|
| 9 | RA190Bn | 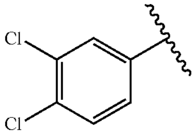 [SMILES: *c1ccc(Cl)c(Cl)c1] | 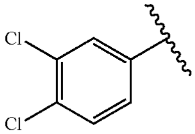 [SMILES: *c1ccc(Cl)c(Cl)c1] | 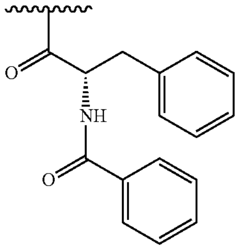 [SMILES: *C(=O)[C@H](Cc1ccccc1)NC(=O)c1ccccc1] | 86 | 121 |
| 10 | RA190PyC | 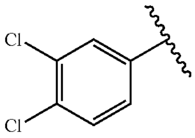 [SMILES: *c1ccc(Cl)c(Cl)c1] | 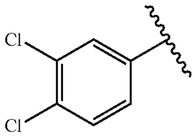 [SMILES: *c1ccc(Cl)c(Cl)c1] | 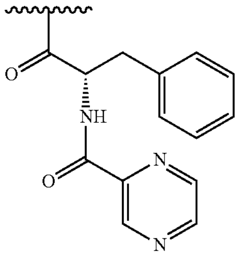 [SMILES: *C(=O)[C@H](Cc1ccccc1)NC(=O)c1cnccn1] | 65 | 84 |
| 11 | RA232 | 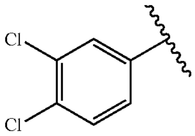 [SMILES: *c1ccc(Cl)c(Cl)c1] | 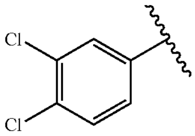 [SMILES: *c1ccc(Cl)c(Cl)c1] | 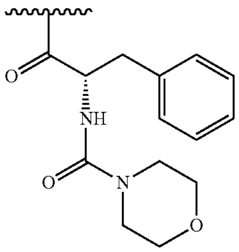 [SMILES: *C(=O)[C@H](Cc1ccccc1)NC(=O)N1CCOCC1] | 61 | 77 |
| 12 | RA230 | 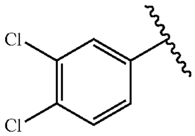 [SMILES: *c1ccc(Cl)c(Cl)c1] | 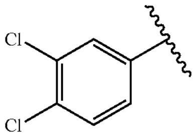 [SMILES: *c1ccc(Cl)c(Cl)c1] | 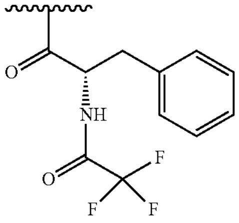 [SMILES: *C(=O)[C@H](Cc1ccccc1)NC(=O)C(F)(F)F] | 47 | 69 |
| 13 | RA233 | 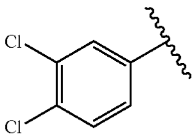 [SMILES: *c1ccc(Cl)c(Cl)c1] | 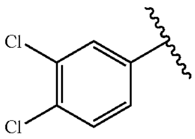 [SMILES: *c1ccc(Cl)c(Cl)c1] | 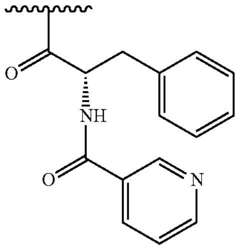 [SMILES: *C(=O)[C@H](Cc1ccccc1)NC(=O)c1cccnc1] | 76 | 98 |

TABLE 1-continued
IC$_{50}$ of compounds 1-57 against HeLa and SKOV3 cells.
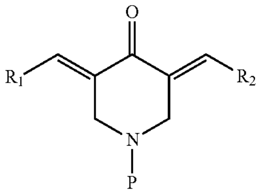
| S. No | Code | R1 | R2 | P | HeLa (nM) | SKOV3 (nM) |
|---|---|---|---|---|---|---|
| 14 | RA234 | 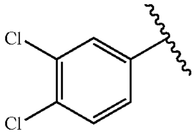 [SMILES: *c1ccc(Cl)c(Cl)c1] | 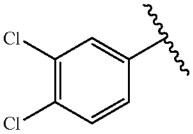 [SMILES: *c1ccc(Cl)c(Cl)c1] | 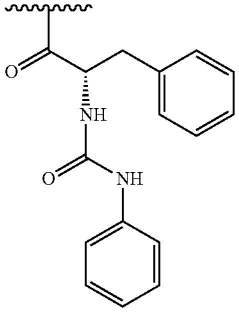 [SMILES: *C(=O)[C@H](Cc1ccccc1)NC(=O)Nc1ccccc1] | 143 | 235 |
| 15 | RA231 | 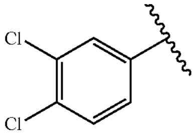 [SMILES: *c1ccc(Cl)c(Cl)c1] | 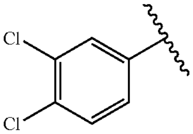 [SMILES: *c1ccc(Cl)c(Cl)c1] | 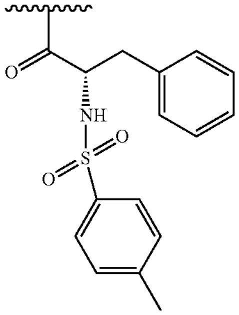 [SMILES: *C(=O)[C@H](Cc1ccccc1)NS(=O)(=O)c1ccc(C)cc1] | 111 | 167 |
| 16 | RA190VA | 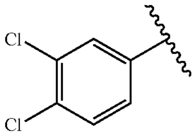 [SMILES: *c1ccc(Cl)c(Cl)c1] | 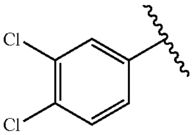 [SMILES: *c1ccc(Cl)c(Cl)c1] | 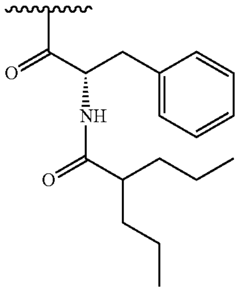 [SMILES: *C(=O)[C@H](Cc1ccccc1)NC(=O)C(CCC)CCC] | 74 | 87 |
| 17 | RA310 | 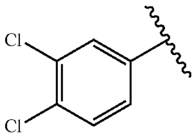 [SMILES: *c1ccc(Cl)c(Cl)c1] | 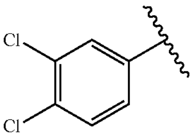 [SMILES: *c1ccc(Cl)c(Cl)c1] | 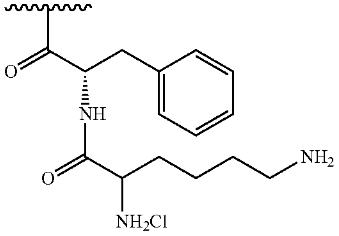 | 543 | 446 |

TABLE 1-continued
$IC_{50}$ of compounds 1-57 against HeLa and SKOV3 cells.
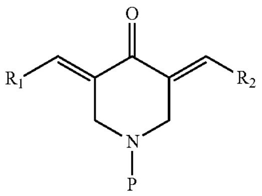
| S. No | Code | R1 | R2 | P | HeLa (nM) | SKOV3 (nM) |
|---|---|---|---|---|---|---|
| 18 | RA310Ac | 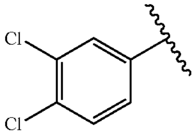 [SMILES: *c1ccc(Cl)c(Cl)c1] | 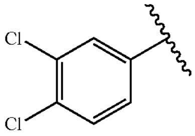 [SMILES: *c1ccc(Cl)c(Cl)c1] | 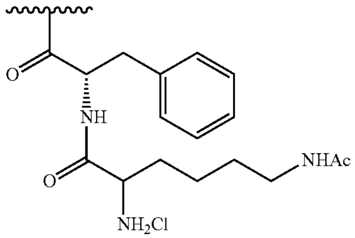 | 195 | 284 |
| 19 | RA195Bn | 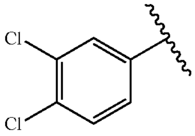 [SMILES: *c1ccc(Cl)c(Cl)c1] | 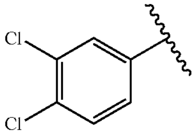 [SMILES: *c1ccc(Cl)c(Cl)c1] | 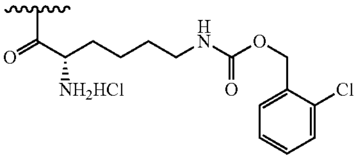 | 146 | 171 |
| 20 | RA190CA | 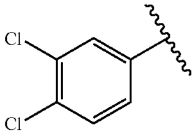 [SMILES: *c1ccc(Cl)c(Cl)c1] | 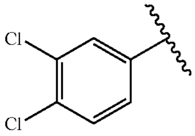 [SMILES: *c1ccc(Cl)c(Cl)c1] | 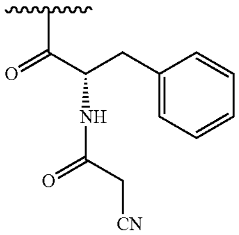 [SMILES: *C(=O)[C@H](Cc1ccccc1)NC(=O)CC#N] | 51 | 84 |
| 21 | RA190TMB | 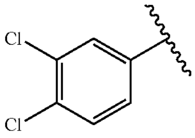 [SMILES: *c1ccc(Cl)c(Cl)c1] | 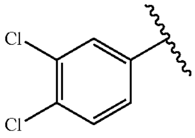 [SMILES: *c1ccc(Cl)c(Cl)c1] | 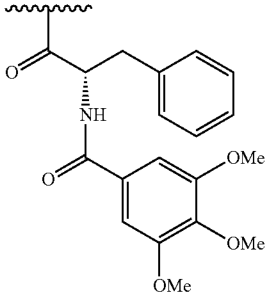 [SMILES: *C(=O)[C@H](Cc1ccccc1)NC(=O)c1cc(OC)c(OC)c(OC)c1] | 94 | 112 |
| 22 | RA190MU | 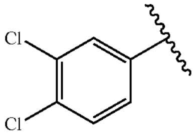 [SMILES: *c1ccc(Cl)c(Cl)c1] | 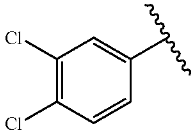 [SMILES: *c1ccc(Cl)c(Cl)c1] | 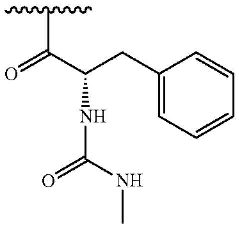 [SMILES: *C(=O)[C@H](Cc1ccccc1)NC(=O)NC] | 141 | 239 |

TABLE 1-continued
IC50 of compounds 1-57 against HeLa and SKOV3 cells.
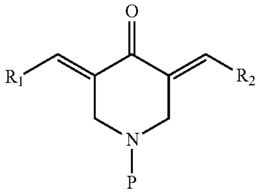
| S. No | Code | R1 | R2 | P | HeLa (nM) | SKOV3 (nM) |
|---|---|---|---|---|---|---|
| 23 | RA190AHA | 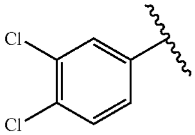 [SMILES: *c1ccc(Cl)c(Cl)c1] | 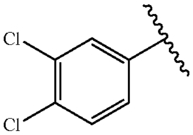 [SMILES: *c1ccc(Cl)c(Cl)c1] | 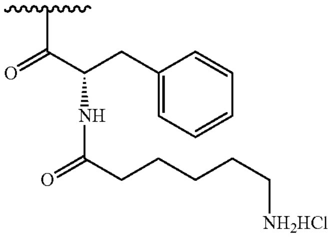 | 62 | 88 |
| 24 | RA190VBA | 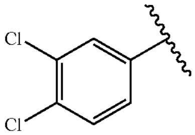 [SMILES: *c1ccc(Cl)c(Cl)c1] | 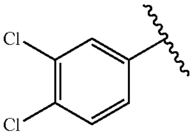 [SMILES: *c1ccc(Cl)c(Cl)c1] | 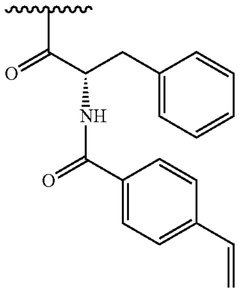 [SMILES: *C(=O)[C@H](Cc1ccccc1)NC(=O)c1ccc(C=C)cc1] | 94 | 178 |
| 25 | RA228 | 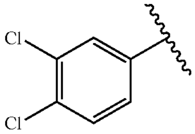 [SMILES: *c1ccc(Cl)c(Cl)c1] | 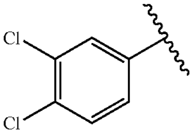 [SMILES: *c1ccc(Cl)c(Cl)c1] | 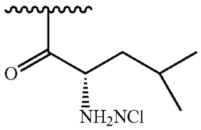 | 66 | 98 |
| 26 | RA7-Val | 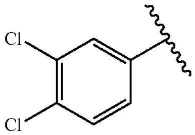 [SMILES: *c1ccc(Cl)c(Cl)c1] | 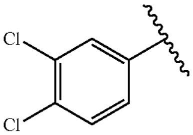 [SMILES: *c1ccc(Cl)c(Cl)c1] | 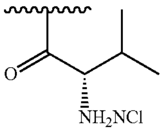 | 64 | 72 |
| 27 | RA7-His | 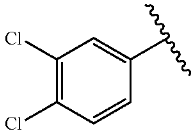 [SMILES: *c1ccc(Cl)c(Cl)c1] | 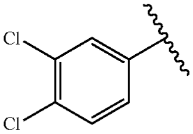 [SMILES: *c1ccc(Cl)c(Cl)c1] | 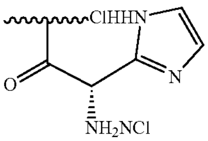 | 132 | 166 |
| 28 | RA221 | 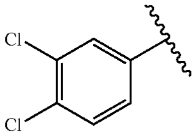 [SMILES: *c1ccc(Cl)c(Cl)c1] | 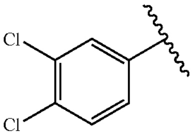 [SMILES: *c1ccc(Cl)c(Cl)c1] | 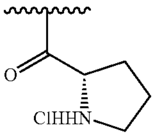 | 43 | 59 |
| 29 | RA295 | 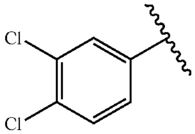 [SMILES: *c1ccc(Cl)c(Cl)c1] | 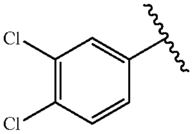 [SMILES: *c1ccc(Cl)c(Cl)c1] | 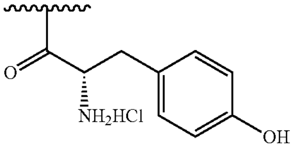 | 89 | 116 |

TABLE 1-continued
IC$_{50}$ of compounds 1-57 against HeLa and SKOV3 cells.
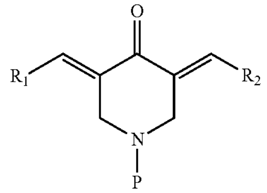
| S. No | Code | R1 | R2 | P | HeLa (nM) | SKOV3 (nM) |
|---|---|---|---|---|---|---|
| 30 | RA195 | 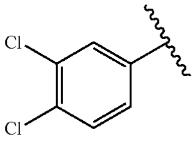 | 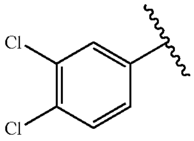 [SMILES: *c1ccc(Cl)c(Cl)c1] | 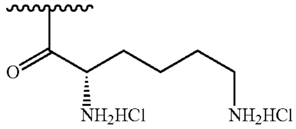 | 109 | 132 |
| 31 | RA7-Gly | 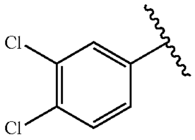 | 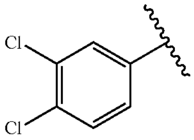 [SMILES: *c1ccc(Cl)c(Cl)c1] | 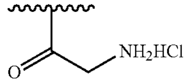 | 65 | 78 |
| 32 | RA7-Ala | 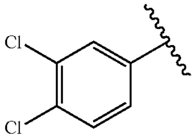 | 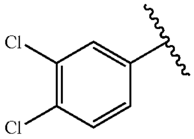 [SMILES: *c1ccc(Cl)c(Cl)c1] | 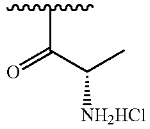 | 68 | 92 |
| 33 | RA7-Ile | 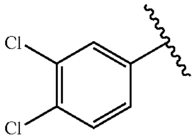 | 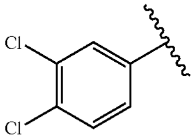 [SMILES: *c1ccc(Cl)c(Cl)c1] | 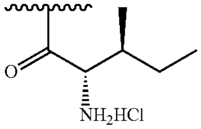 | 72 | 101 |
| 34 | RA7-IleC | 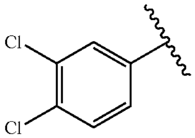 | 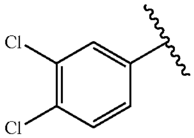 [SMILES: *c1ccc(Cl)c(Cl)c1] | 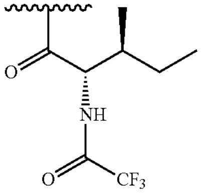 [SMILES: *C(=O)[C@@H](NC(=O)C(F)(F)F)[C@@H](C)CC] | 61 | 77 |
| 35 | RA190MS | 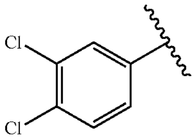 | 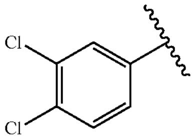 [SMILES: *c1ccc(Cl)c(Cl)c1] | 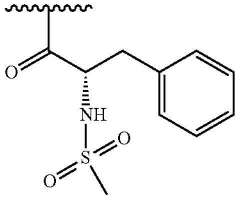 [SMILES: *C(=O)[C@H](Cc1ccccc1)NS(C)(=O)=O] | 86 | 133 |
| 36 | RA371 | 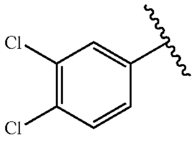 | 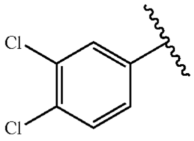 [SMILES: *c1ccc(Cl)c(Cl)c1] | 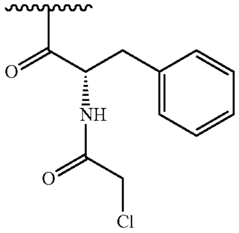 [SMILES: *C(=O)[C@H](Cc1ccccc1)NC(=O)CCl] | 44 | 47 |

TABLE 1-continued
IC$_{50}$ of compounds 1-57 against HeLa and SKOV3 cells.
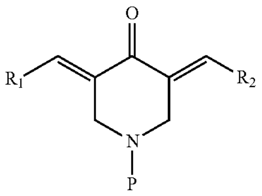
| S. No | Code | R1 | R2 | P | HeLa (nM) | SKOV3 (nM) |
|---|---|---|---|---|---|---|
| 37 | RA-asy | 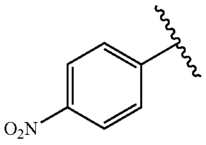 [SMILES: *c1ccc([N+](=O)[O-])cc1] | 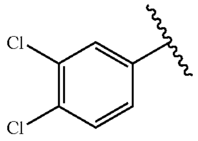 | H | 312 | 398 |
| 38 | RA-asyP | 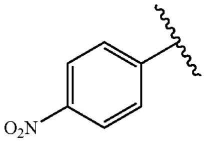 [SMILES: *c1ccc([N+](=O)[O-])cc1] | 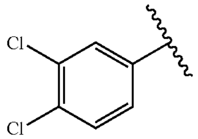 | 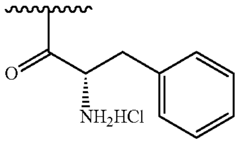 | 48 | 62 |
| 39 | RA183Acr | 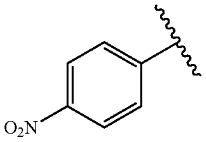 | 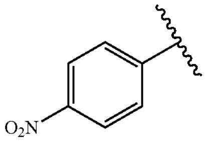 | 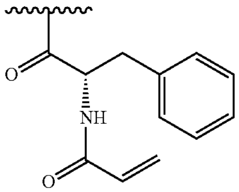 | 49 | 64 |
| 40 | RA183Ac | 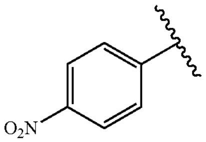 | 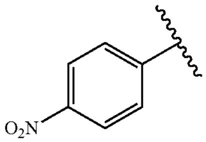 | 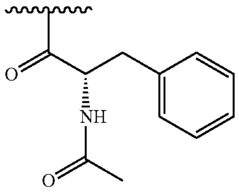 [SMILES: *C(=O)[C@H](Cc1ccccc1)NC(C)=O] | 56 | 71 |
| 41 | RA183CF3 | 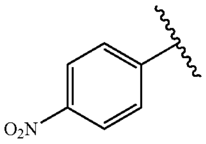 | 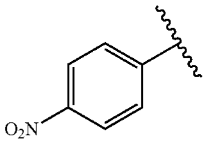 | 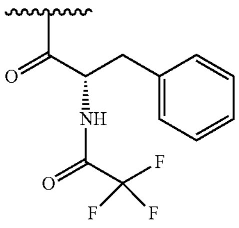 [SMILES: *C(=O)[C@H](Cc1ccccc1)NC(=O)C(F)(F)F] | 45 | 79 |
| 42 | RA375 | 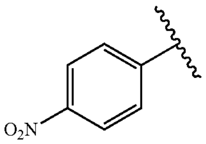 [SMILES: *c1ccc([N+](=O)[O-])cc1] | 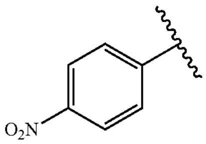 [SMILES: *c1ccc([N+](=O)[O-])cc1] | 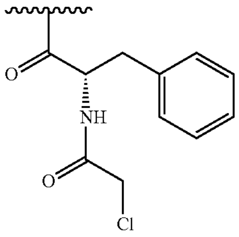 [SMILES: *C(=O)[C@H](Cc1ccccc1)NC(=O)CCl] | 13 | 26 |
| 43 | DHBC | 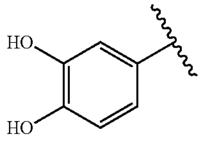 [SMILES: *c1ccc(O)c(O)c1] | 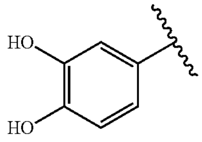 [SMILES: *c1ccc(O)c(O)c1] | H | 667 | 788 |

TABLE 1-continued
IC$_{50}$ of compounds 1-57 against HeLa and SKOV3 cells.
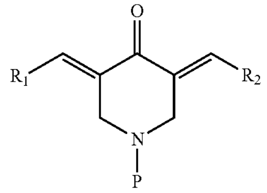
| S. No | Code | R1 | R2 | P | HeLa (nM) | SKOV3 (nM) |
|---|---|---|---|---|---|---|
| 44 | HBC | 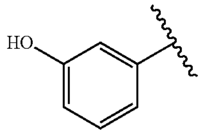 [SMILES: *c1cccc(O)c1] | 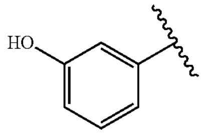 [SMILES: *c1cccc(O)c1] | H | 453 | 531 |
| 45 | RA-CTF | 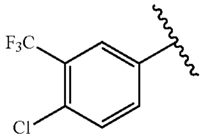 [SMILES: *c1ccc(Cl)c(C(F)(F)F)c1] | 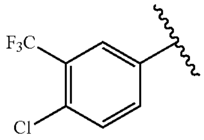 | H | 324 | 457 |
| 46 | RA-CTFP | 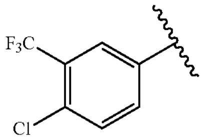 [SMILES: *c1ccc(Cl)c(C(F)(F)F)c1] | 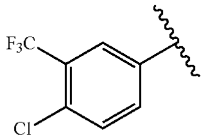 | 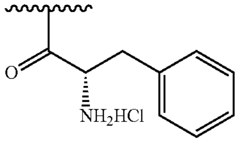 | 56 | 81 |
| 47 | RA181 | 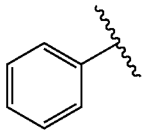 [SMILES: *c1ccccc1] | 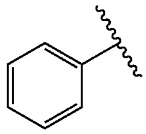 [SMILES: *c1ccccc1] | 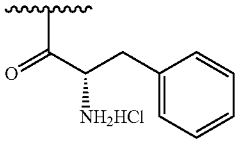 | 63 | 89 |
| 48 | RA-4Cl | 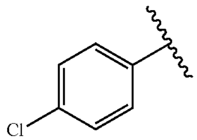 | 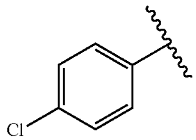 [SMILES: *c1ccc(Cl)cc1] | 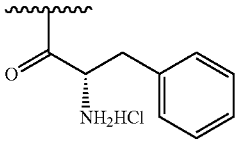 | 71 | 83 |
| 49 | RA-TMP | 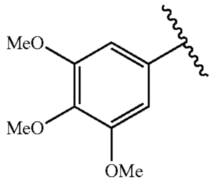 [SMILES: *c1cc(OC)c(OC)c(OC)c1] | 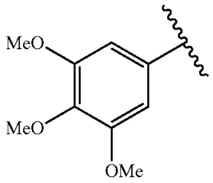 [SMILES: *c1cc(OC)c(OC)c(OC)c1] | 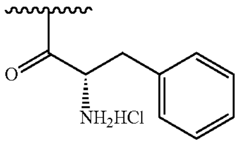 | 78 | 125 |
| 50 | RA-BT | 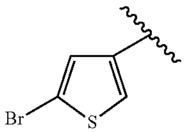 [SMILES: *c1csc(Br)c1] | 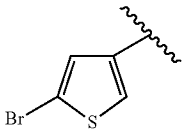 | H | 454 | 642 |
| 51 | RA-BTP | 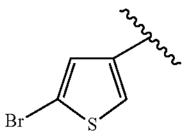 [SMILES: *c1csc(Br)c1] | 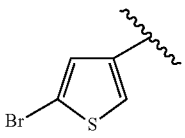 [SMILES: *c1csc(Br)c1] | 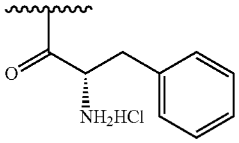 | 212 | 243 |

TABLE 1-continued
IC$_{50}$ of compounds 1-57 against HeLa and SKOV3 cells.
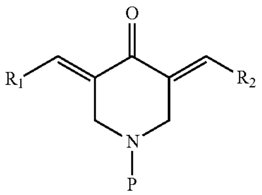
| S. No | Code | R1 | R2 | P | HeLa (nM) | SKOV3 (nM) |
|---|---|---|---|---|---|---|
| 52 | RA-BTPCA | 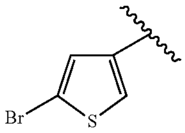 [SMILES: *c1csc(Br)c1] | 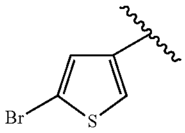 | 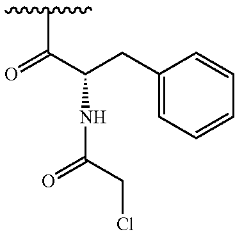 [SMILES: *C(=O)[C@H](Cc1ccccc1)NC(=O)CCl] | 132 | 189 |
| 53 | RA-biP | 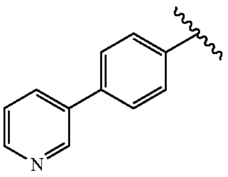 [SMILES: *c1ccc(-c2cccnc2)cc1] | 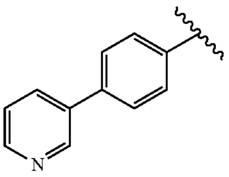 [SMILES: *c1ccc(-c2cccnc2)cc1] | H | 1432 | 1786 |
| 54 | RA-Cinn | 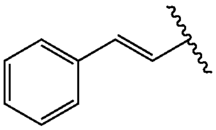 [SMILES: */C=C/c1ccccc1] | 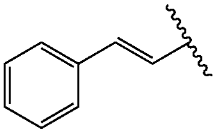 [SMILES: */C=C/c1ccccc1] | H | >5000 | >5000 |
| 55 | RA181C | 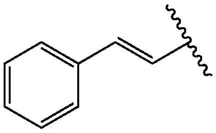 [SMILES: */C=C/c1ccccc1] | 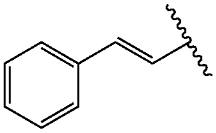 [SMILES: */C=C/c1ccccc1] | 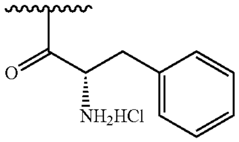 | >2500 | >2500 |
| 56 | RA190H | 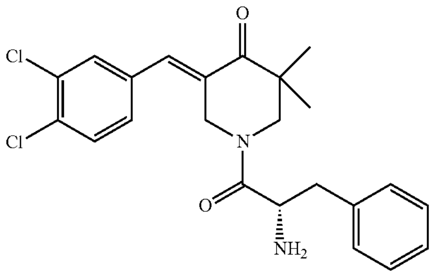 | | | 562 | |
| 57 | RA190B | 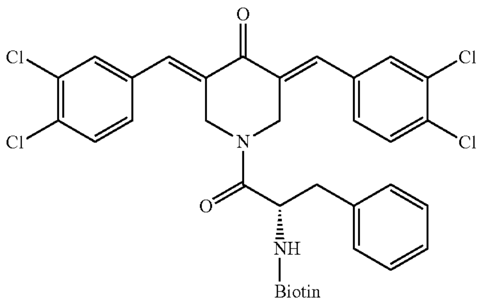 | | | 346 | |

Biotinylated RA190 (RA190B, FIG. 1A) is utilized as a probe to detect covalent binding to its cellular target(s) in detergent lysates of cancer cell lines (10). Using this approach, a predominant band of 42 KDa was labeled by RA190B and subsequently identified as RPN13 (10). Here, the ability of compounds (FIG. 1A) to compete with RA190B binding to its 42 kDa cellular target (FIG. 1B) were examined. Compounds, including bortezomib as a negative control, were incubated with HeLa cell lysate and then RA190B added. Upon SDS-PAGE, transfer to PVDF membrane, and probing of these lysates with HRP-streptavidin it was evident that nitrogen-bearing piperidone ring moieties (RA190, RA181, RA190H, and RA338) competed labeling by RA190B to a greater extent compared to a cyclohexanone bis-benzylidine moiety, RA142C.

The ability of RA181, but not RA181C, to compete with RA190B binding to the 42 kDa cellular target suggests that the span of the aromatic wings is an important factor for RPN13 binding (FIG. 1B). The half molecule RA190H did compete RA190B labeling, suggesting that a single aromatic wing and enone functionality may suffice. However, the IC50 for killing HeLa cells by RA190H is 6-fold higher than for RA190, 562 nM versus 85 nM respectively (See Table 1), and only weakly caused an accumulation of high molecular weight polyubiquitinated proteins (FIG. 1C), suggesting both are optimal. The compounds which competed binding of RA190B to its 42 kDa cellular target, RA181 and RA338, also produced a rapid accumulation of high molecular weight polyubiquitinated proteins when added to cells. Conversely, RA181C, RA142C, and RA181C, which failed to compete binding by RA190B, produced only minimal accumulation of polyubiquitinated proteins (FIG. 1C) and exhibited >2500 nM $IC_{50}$ in cell killing assays (See Table 1).

Figure 2:
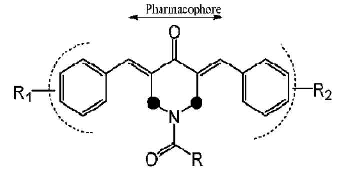
FIG. 2 illustrates the impact of modifications around the RA190 core moiety.
Figure 2:
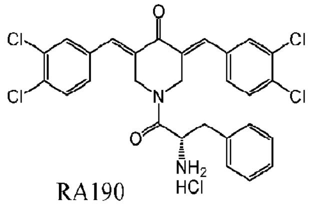
Figure 2:
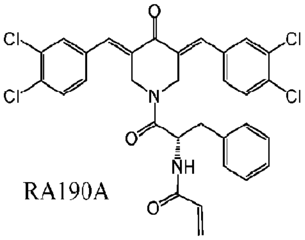
Figure 2:
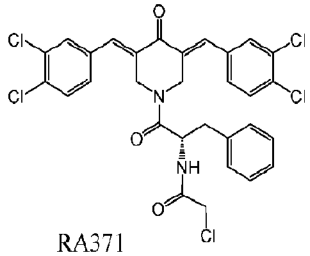
Figure 2:
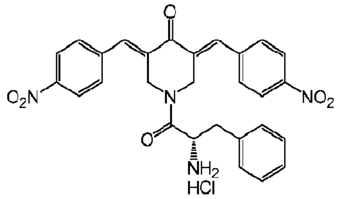
Figure 2:
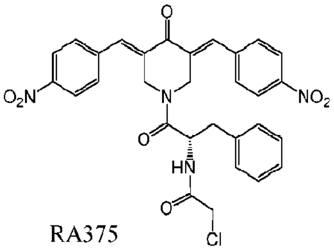
Figure 2:
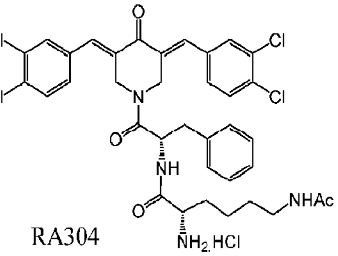
Figure 2:
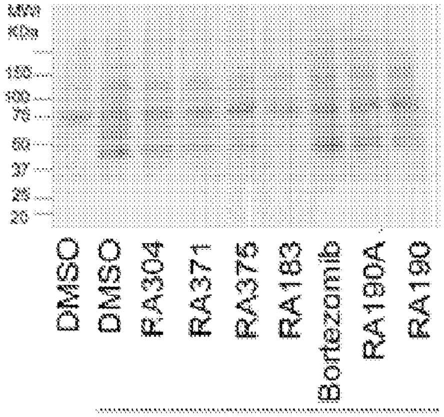

When the first series of 36 compounds (Table 1) were tested using an XTT assay for their cytotoxicity against two human cell lines derived from a cervical cancer (HeLa) and an ovarian cancer (SKOV3), enhanced potency was evident with the addition of a war head to the free amine in RA190, with increased potency from H<$COCH_3$<$COCF_3$<CO—CH'$CH_2$<CO—$CH_2$Cl. This enhanced potency was not noticeably associated with increased aqueous solubility. Addition of a second charged amino acid, lysine, to the phenyl alanine of RA190 (compounds 17, 18 and 19 in Table 1) achieved significant aqueous solubility but decreased potency. Compound 17 (RA310) achieved complete aqueous solubility with 3-fold decreased potency compared to RA190. Chloroacetamide-containing RA371 (compound 36 in Table 1 and FIG. 2A) was the most potent molecule in this series. The impact of substituents of the aromatic ring on the potency of molecules was also examined. The presence of either an electron withdrawing group (EWG) or an electron donating group (EDG) influences the reactivity of a Michael acceptor towards the target protein but can also impact specificity/selectivity. Compounds 37-49 were synthesized using a variety of EWG/EDG substituents on the aromatic ring. The most promising substituents identified in the first series ($COCH_3$<$COCF_3$<CO—CH═$CH_2$<CO—$CH_2$Cl) were chosen to couple with core ring "N" and tested all the analogs for their activity against the two cancer cell lines. Molecules possessing substituents with stronger EWG ($NO_2$>F>Cl>H>OMe>OH) effects were the most potent in the series. Remarkably, RA375 (compound 42 in Table 1 and FIG. 2A) exhibited ten-fold greater activity against the two cancer lines than RA190, likely reflecting ring substituents with the strongest EWG and the potent chloroacetamide moiety. In a competition assay, pre-incubation of OV2008 cancer cell lysate with selected compounds, including RA375, abrogated the binding of RA190B to its 42 KDa cellular target to varying degrees (FIG. 2B) that were consistent with their IC50 values for cell killing.

Figure 3:
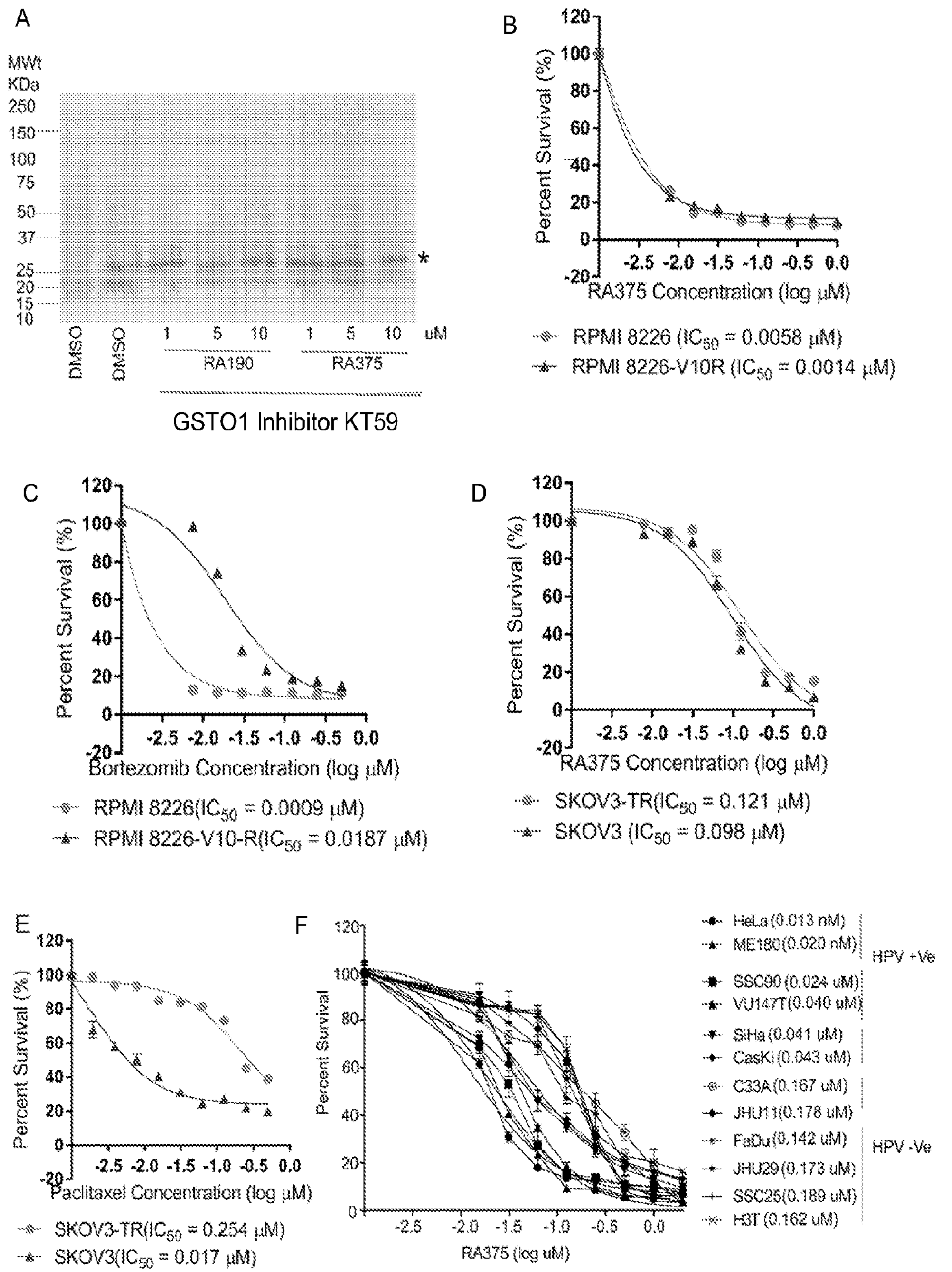
FIG. 3 illustrates the impact of RA375 on GSTO1 binding by KT59 and cancer cell viability.

Compounds containing hydroxyl substituents (43 and 44, Table 1) exhibited complete aqueous solubility but 5-8 fold decreased potency compared to RA190. The impact on potency of replacing the aromatic ring with a small heterocycle and bulky groups was examined. Heterocycle replacement (Compounds 51 and 52, Table 1) led to 3-4 fold decreased cytotoxic potency whereas the biphenyl replacement caused a 7 fold decrease in activity. Surprisingly extension of one unsaturated bond leads to 20-25 fold reduced activity (Compounds 54, 55, Table 1). By contrast, the compounds possessing a chloroacetamide group, RA371 and RA375 (compounds 36 and 42, Table 1), were the most potent in the series. Although chloroacetamide is the active component of several candidate GSTO1 inhibitors (28, 29), in a competition assay using KT59 as a click chemistry probe (28), there was no evidence of RA375 competing its binding to GSTO1 (FIG. 3A).

The cyclohexanone frame of these molecules tends to assume conformational isomerism which might negatively influence properties. A bridge between two $SP^3$ carbons of the cyclohexanone may confer a more restricted confirmation that can affect the reactivity of the Michael acceptor (compounds 56-67, Table 2). Bridged compounds exhibited one to two fold decreased cytotoxicity compared to without the bridge, and were not further pursued for these uses. Instead, RA371 and RA375 were selected for further studies.

TABLE 2

$IC_{50}$ of bridge compounds 58-70 against HeLa and SKOV3 cells.

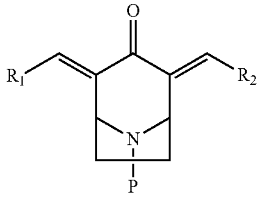

| | | | | | HeLa | SKOV3 |
|---|---|---|---|---|---|---|
| 58 | RA330 | 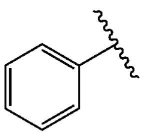 [SMILES: *c1ccccc1] | 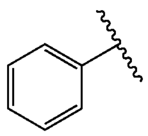 [SMILES: *c1ccccc1] | H | 239 | 278 |

TABLE 2-continued
IC$_{50}$ of bridge compounds 58-70 against HeLa and SKOV3 cells.
| | | | | | HeLa | SKOV3 |
|---|---|---|---|---|---|---|
| | | | 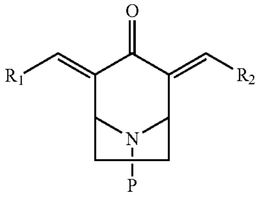 | | | |
| 59 | RA336 | 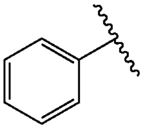 [SMILES: *c1ccccc1] | 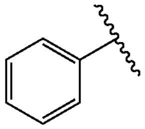 [SMILES: *c1ccccc1] | C(O)=CH=CH2 | 146 | 185 |
| 60 | RA337 | 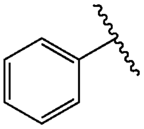 [SMILES: *c1ccccc1] | 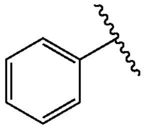 [SMILES: *c1ccccc1] | C(O)CH3 | 186 | 231 |
| 61 | RA335 | 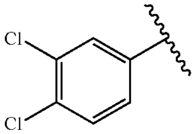 [SMILES: *c1ccc(Cl)c(Cl)c1] | 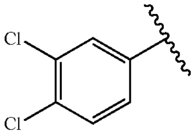 [SMILES: *c1ccc(Cl)c(Cl)c1] | C(O)CH3 | 161 | 251 |
| 62 | RA329 | 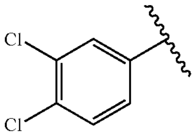 [SMILES: *c1ccc(Cl)c(Cl)c1] | 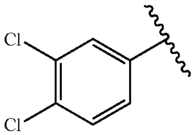 [SMILES: *c1ccc(Cl)c(Cl)c1] | H | 407 | 471 |
| 63 | RA338 | 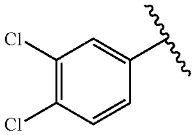 | 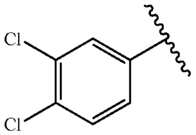 [SMILES: *c1ccc(Cl)c(Cl)c1] | 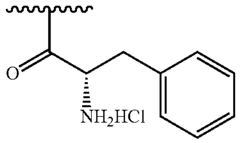 | 66 | 81 |
| 64 | RA334 | 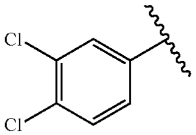 | 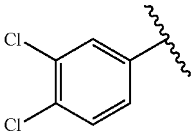 [SMILES: *c1ccc(Cl)c(Cl)c1] | C(O)=CH=CH2 | 101 | 186 |
| 65 | RA339 | 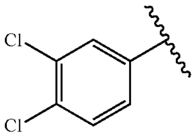 | 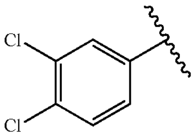 [SMILES: *c1ccc(Cl)c(Cl)c1] | 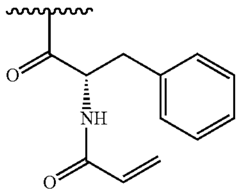 [SMILES: *C(=O)[C@H](Cc1ccccc1)NC(=O)C=C] | 46 | 54 |
| 66 | RA331 | 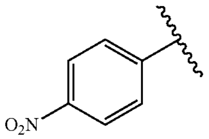 | 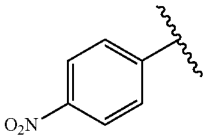 | H | 236 | 301 |

TABLE 2-continued $IC_{50}$ of bridge compounds 58-70 against HeLa and SKOV3 cells.

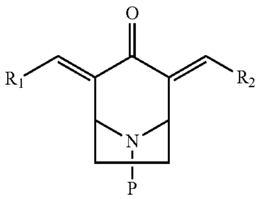

| | | | | | HeLa | SKOV3 |
|---|---|---|---|---|---|---|
| 67 | RA333 | 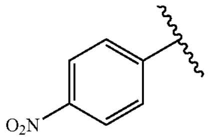 | 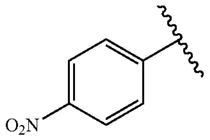 | C(O)=CH=CH2 | 112 | 167 |
| 68 | RA332 | 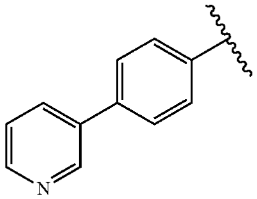 [SMILES: *c1ccc(-c2cccnc2)cc1] | 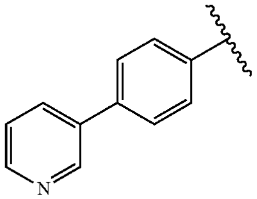 [SMILES: *c1ccc(-c2cccnc2)cc1] | H | 243 | 376 |
| 69 | RA340 | 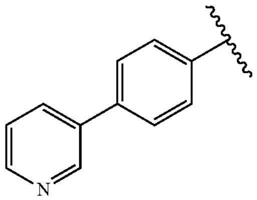 [SMILES: *c1ccc(-c2cccnc2)cc1] | 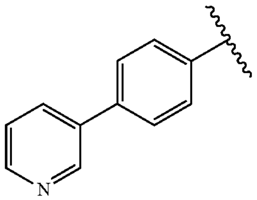 [SMILES: *c1ccc(-c2cccnc2)cc1] | C(O)=CH=CH2 | 184 | 259 |
| 70 | RA342 | 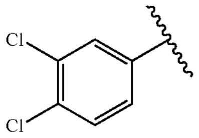 | 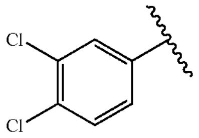 [SMILES: *c1ccc(Cl)c(Cl)c1] | 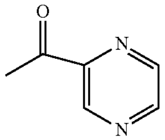 | 122 | 181 |

Effect of Inventive Compounds on Diverse Cancer Cell Lines

The cytotoxic efficacy of selected compounds was assessed against multiple myeloma (MM) cell lines, as this is a validated clinical target for the licensed proteasome inhibitors. Cell lines were treated for 48 hr with 2-fold titrations of each compound (Table 3) and their effect on proliferation compared to RA190, the structurally-related DUB inhibitors b-AP15 (31) and VLX1570 (32), using the MTT assay. The MM lines were most sensitive to RA375 treatment (Table 3). Bortezomib-treated patients and cell lines typically develop resistance (33, 34). When testing its potency against two MM cell lines that were selected for resistance in vitro by extended culture in bortezomib (V10R), RA375 is similarly efficacious against both the bortezomib-resistant derivative lines and their parental lines, consistent with a distinct mode of action from bortezomib (Table 3 and FIGS. 3B-3C).

TABLE 3

$IC_{50}$ values (nM) of compounds for cell lines derived from diverse cancer types and normal tissues.

| | | Compounds | | | |
|---|---|---|---|---|---|
| Cancer Type | Cell Lines | RA190 | RA183 | RA375 | Bortezomib |
| Cervical | HeLa | 85 | 112 | 13 | |
| (HPV +ve) | SiHa | 603 | 263 | 41 | |
| | CaSki | 324 | 312 | 43 | |
| | ME180 | 183 | 293 | 20 | |
| Cervical | HT3 | | | 162 | |
| (HPV −ve) | C33A | | | 167 | |
| Head & Neck | SSC90 | | | 24 | |
| (HPV +ve) | VU147T | | | 40 | |
| Head & Neck | SSC25 | | | 189 | |
| (HPV −ve) | JHU11 | | | 178 | |
| | JHU29 | | | 173 | |
| | FaDu | | | 142 | |
| Ovarian | OVCAR3 | 120 | 78 | 17 | |
| | OVCAR5 | 64 | 56 | 12 | |
| | ES2 | 115 | 75 | 19 | |
| | TOV21G | 83 | 44 | 6 | |
| | SKOV3 | 73 | 54 | 26 | |
| | SKOV3-TR | 109 | 77 | 22 | |
| | A2780 | 139 | 161 | 37 | |
| | ID8 (murine) | 211 | 198 | 44 | |

TABLE 3-continued

IC50 values (nM) of compounds for cell lines derived from diverse cancer types and normal tissues.

| Cancer Type | Cell Lines | RA190 | RA183 | RA375 | Bortezomib |
|---|---|---|---|---|---|
| | | Compounds | | | |
| Colon | HCT116 | 239 | 193 | 89 | 3.2 |
| | HCT116 ARID1A$^{-/-}$ | 164 | 155 | 20 | 2.8 |
| Multiple Myeloma | MM.1S | 72 | 46 | 11 | |
| | RPMI8226 | 45 | 88 | 9 | |
| | RPMI8226-V10R | 47 | 139 | 6 | |
| | ANBL6 | 67 | 58 | 12 | |
| | ANBL6-V10R | 55 | 103 | 16 | |
| Prostate | LNCaP | 242 | 186 | 60 | |
| | PC3 | 162 | 133 | 27 | |
| Triple Negative Breast | HS578T | 78 | 89 | 3 | |
| | MDA-MB231 | 134 | 124 | 22 | |
| | HCC1806 | 52 | 44 | 17 | |
| Human Foreskin Fibroblast | HFF | >1000 | >1000 | >1000 | >100 |
| Mouse Skin | Keratinocytes | >1000 | >1000 | >1000 | >100 |

An initial survey of cytotoxicity for a panel of epithelial cancer cell lines suggested that ovarian, triple negative breast cancer (TNBC), and colon cancer cell lines were particularly sensitive to RA375. RA375 showed similar potency in both a paclitaxel-resistant SKOV3 clone and its parental cell line (Table 3 and FIG. 3D-3E). RA375 was synergistic with doxorubicin in several ovarian cancer lines (Table 3). Recent work suggested that the mutant TP53-driven TNBC subtype, like high grade ovarian cancer, is highly dependent on proteasome function (35) and RA375 showed significant potency against a small panel of TNBC lines. RA375 also potently inhibited TNBC and ovarian cancer cell colony formation FIG. 4A, 4B.

Figure 5:
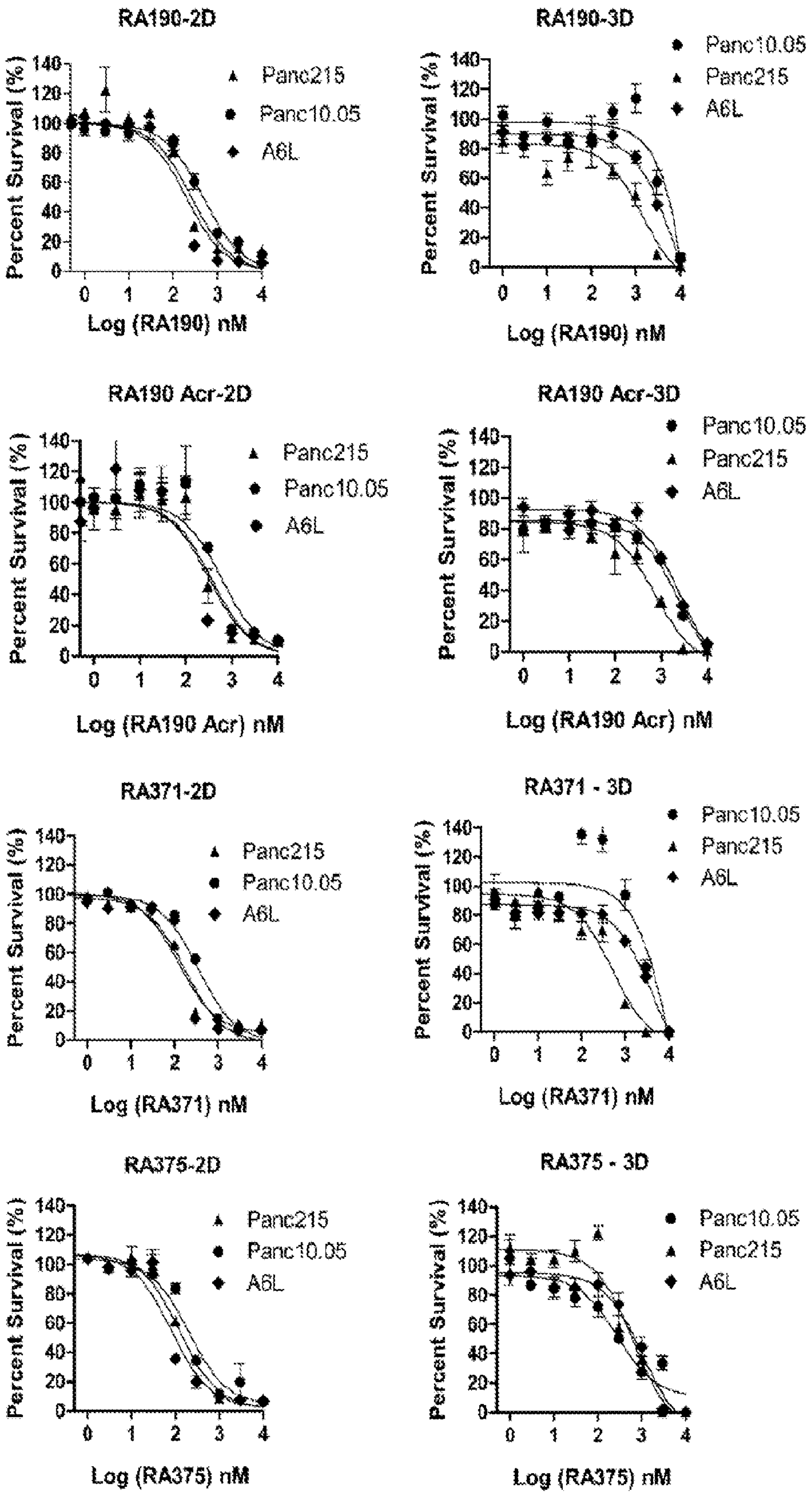
FIG. 5 illustrates the effects of compounds against pancreatic cancer cell growth. A panel of pancreatic cancer cell lines (Panc 10.05, Panc 215 and A6L) growing in 2D culture (left) as compared to 3D culture (right) were measured at 48 hr after growth in the presence of compounds at indicated concentrations. For 2D killing assays, 5000 cells/well were plated in a 96 well plate in 504, medium. After 24 hr cells were treated with compounds in 504, medium and incubated at 37° C. for 96 hr. After the incubation medium was removed, 0.2% SDS was added (50 μL/well) and incubated at 37° C. for 2 hrs. Then 150 μL of SYBR Green I solution (1:750 in water) was mixed with the cell lysate, and the fluorescence measured using FLUOstar-Galaxy plate reader. For 3D killing assays, 3000 cells/well seeded in a 384 well plate (Corning spheroid microplate, cat No. 3830) in 25 μL medium. After confirming spheroid formation (200-400 μm) at day 3, drug solutions (25 μL) were added to corresponding wells. At day 6, 10% SDS (5 μL) was added to each well followed by 50 μL, of cell-titer-glo reagent. The microplate was vigorously mixed for 2 min on an orbital shaker to induce cell lysis and release cellular ATP, 100 μL transferred to a white flat bottom 384-well plate (Sigma 460372). After briefly centrifuging the plate to remove bubbles the ATP quantification was measured using a Wallac 1420 multi label counter.

Cervical cancer is also a promising target because the HPV E6 oncoprotein drives transformation by proteasome-mediated degradation of key cellular targets, notably the p53. RA375 promoted the rapid onset of apoptosis in HPV16+ CaSki and SiHa and HPV18+ HeLa cells (Table 3). The same phenomenon was clear in HPV+ head and neck cancer lines (FIG. 3F). Overall, HPV negative cervical and head and neck cancer lines, were ~4 fold less sensitive to RA375 than HPV+ lines, regardless of HPV genotype. Human pancreatic cancer-derived cell lines were substantially less sensitive to these compounds whether using MTT assay in either a 2D or 3D culture format (FIG. 5).

Impact of Glutathione Metabolism on RA375 Potency

Figure 4:
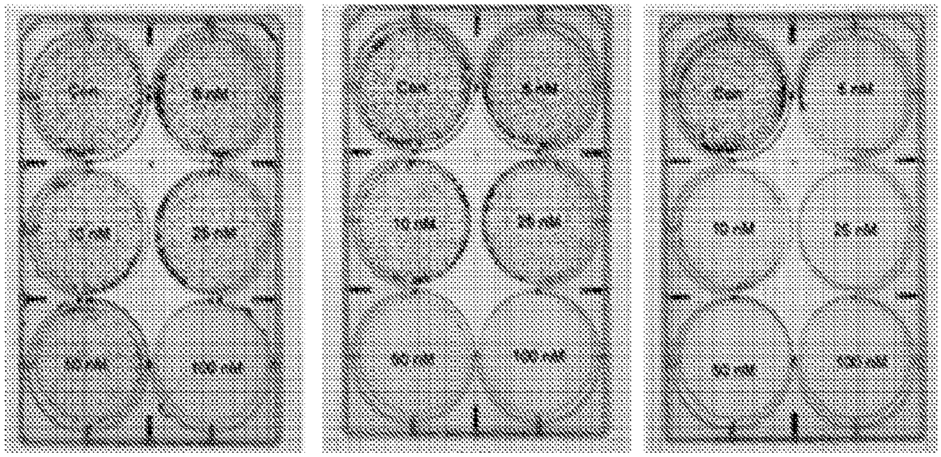
FIG. 4 illustrates the impact of RA190, RA371 and RA375 on clonogenicity, cell viability and levels and size of polyubiqutinated proteins. Cells were treated with compounds at the indicated doses and incubated for 14 days to allow colony formation. The plates were stained with 1% crystal violet in methanol and clusters containing 50 or more cells were scored as a colony.
Figure 4:
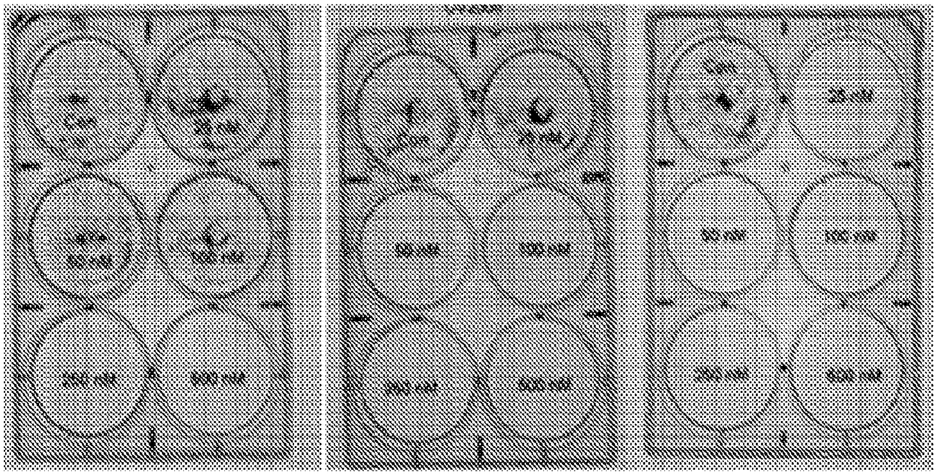
Figure 4:
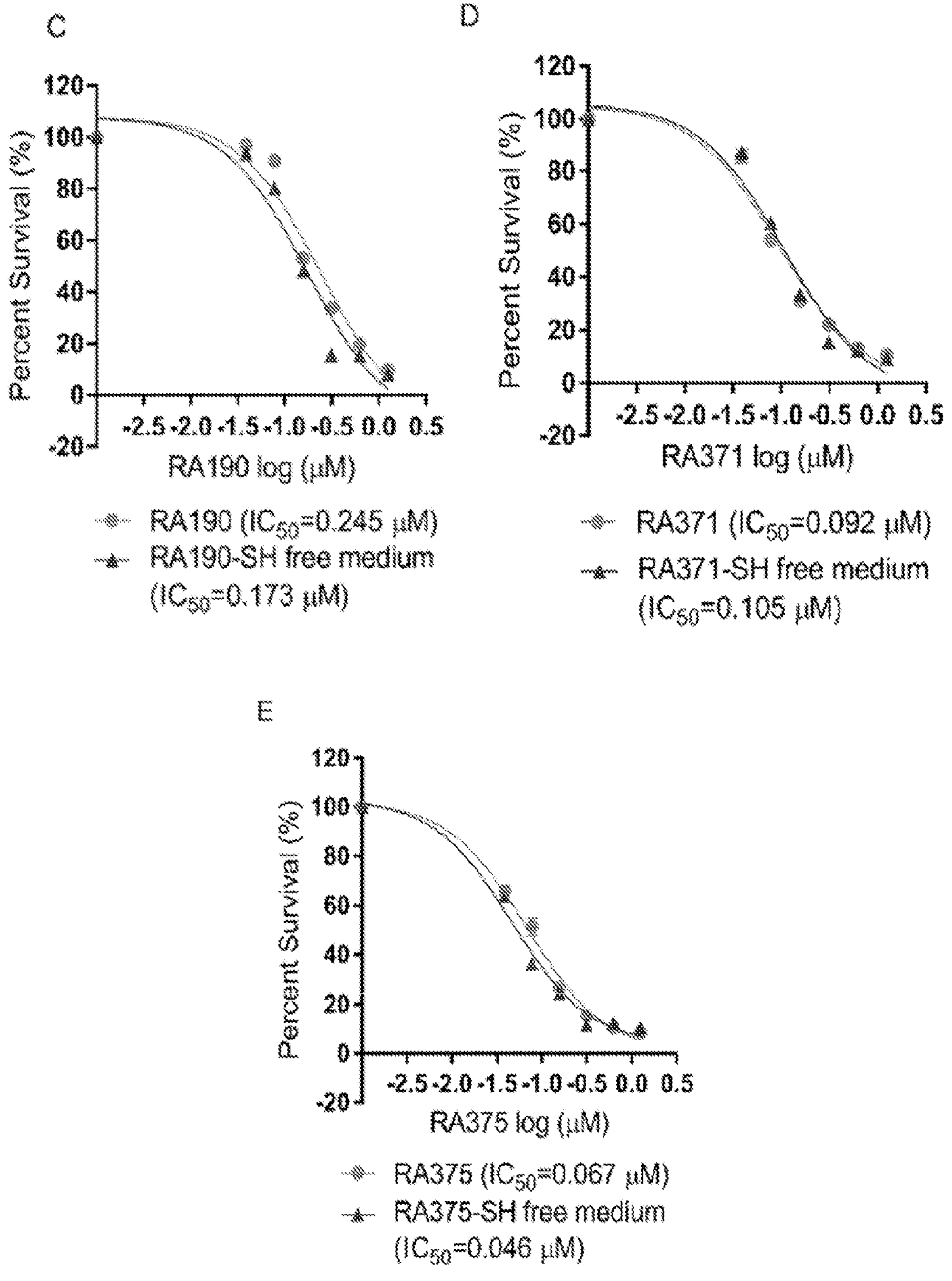
Figure 6:
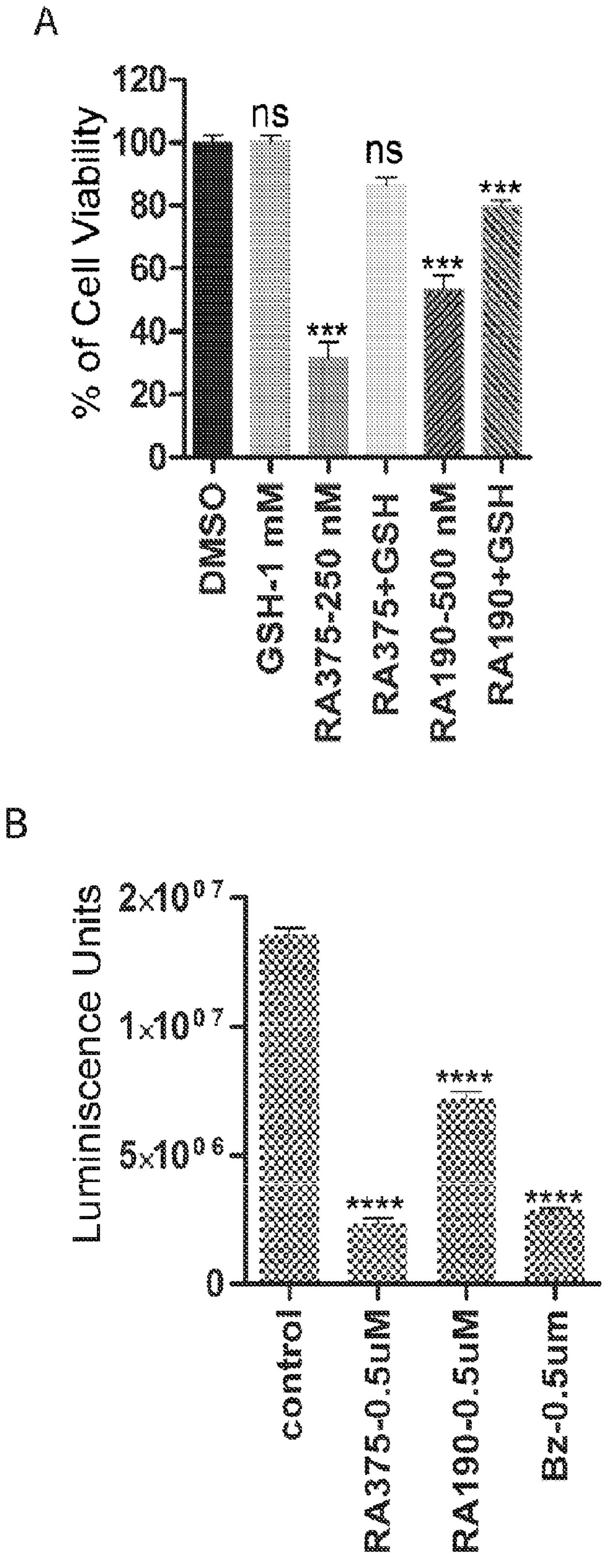
FIG. 6 illustrates the effect of GSH on RA375 activity.

To determine whether reaction of extracellular thiols impacts the potency of the RA371 and RA375, MTT assays were performed on SKOV3 cells either in the presence or absence of cysteine and methionine in the cell culture medium (although 10% FBS was utilized that had not been dialyzed to support cell viability). No significant difference in the activity of compounds in media with, versus without, cysteine and methionine was noted (FIG. 4C-4E). Addition of glutathione (GSH) to 0.5 mM in the SKOV3 cell culture medium reduced the cell killing effect of 250 nM RA375 ($p<0.001$) and 500 nM RA190 ($p<0.001$) as compared to without (FIG. 6A). Bortezomib profoundly reduced cellular GSH levels (FIG. 6B) in SKOV3 cells ($p<0.001$) as previously reported in other cell types (26, 27). Similarly, RA375, and to a lesser extent RA190 (each $p<0.001$), reduced intracellular GSH levels (FIG. 6B), implying that these compounds may act in part by depleting GSH levels in cancer cells, and thus contribute to the ROS-associated cell killing effects in addition to their ER stress related to proteasome inhibition.

Loss of ARID1A function is a common driver of ovarian and some other cancer types, and it confers vulnerability to inhibition of GSH (36). The parental HCT116 cell line was 4-fold less sensitive to RA375 than its isogenic ARID1A knockout, although this difference was less apparent for RA183, RA190 and bortezomib (Table 3). There was no significant difference in the sensitivity of ARID1A wild type (OVCAR3, OVCAR5, ES2) and deficient (TOV21G, SKOV3, A2780) ovarian cancer lines to RA375 treatment (Table 3) (37).

Induction of Unresolved ER Stress, ROS and Subsequent Apoptosis by RA375

Figure 7:
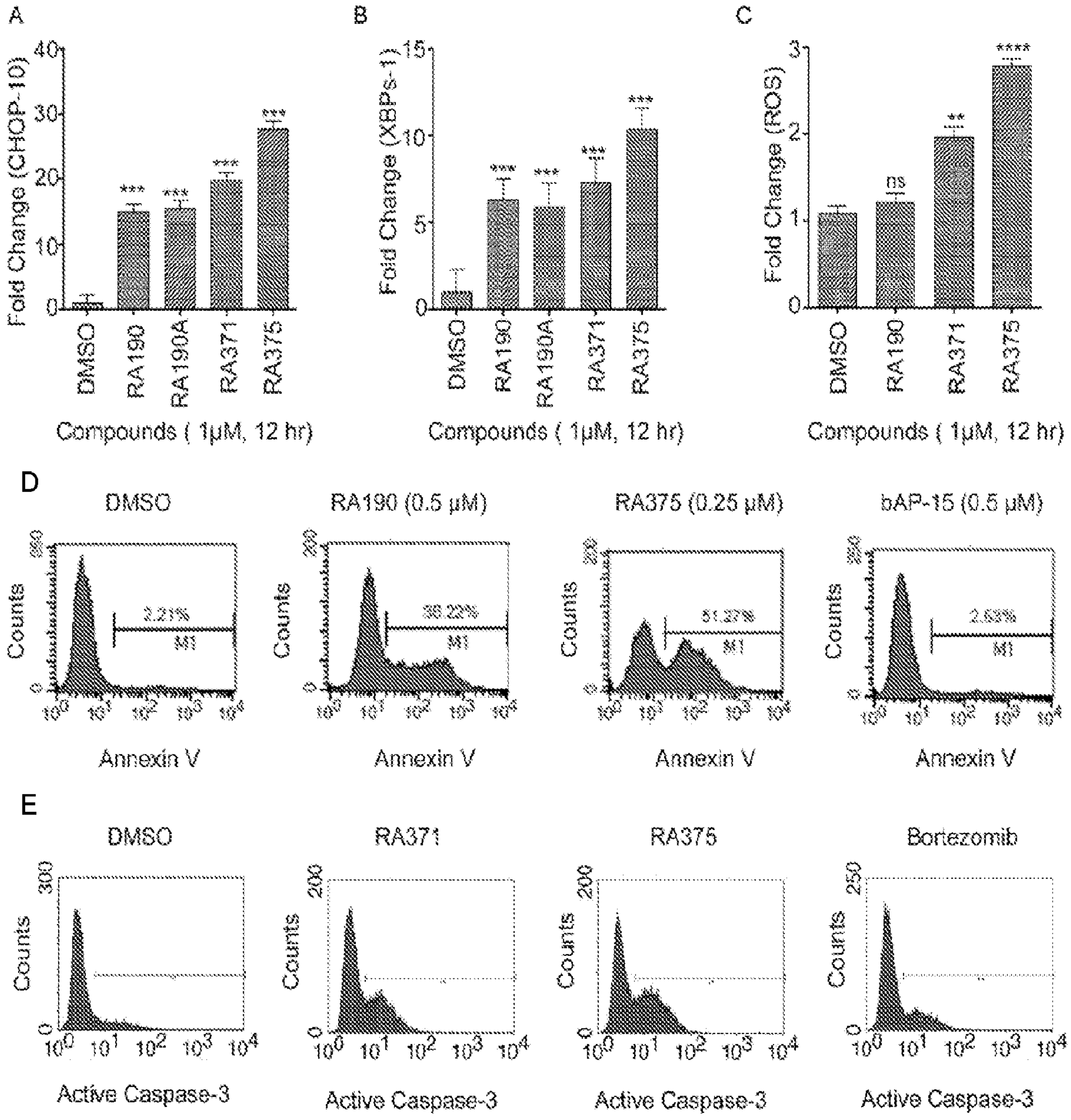
FIG. 7 illustrates RA375 activates UPR signaling, ROS production and apoptosis.
Figure 8:
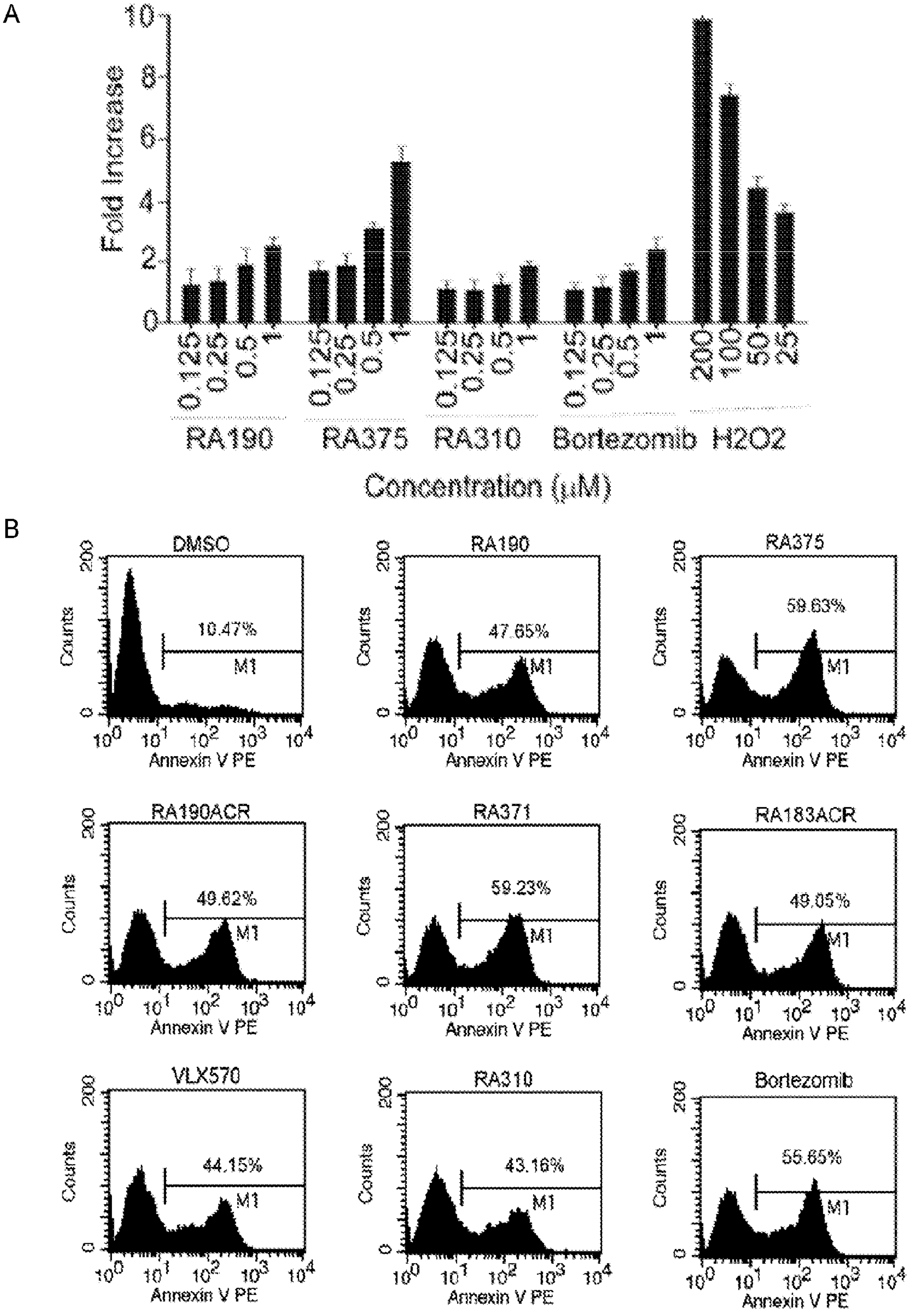
FIG. 8 illustrates activation of ROS production and apoptosis by compounds.

Inhibition of proteasome function (10) triggers the unfolded protein response (UPR) and thereafter apoptosis independently of p53 signaling (38-40). Early UPR-induced signaling is rapidly upregulated by RA375 treatment of ES2 cells including CHOP-10 mRNA (FIG. 7A) and XBP1 spliced mRNA (FIG. 7B). RA371 and RA375 induced significantly higher levels of CHOP-10 mRNA than RA190 ($p<0.01$ and $p<0.001$ respectively, FIG. 7A), whereas only RA375 induced significantly higher levels of XBP1 spliced mRNA ($p<0.001$, FIG. 7B). Since RA375 depleted cellular GSH (FIG. 6B), reducing protection from oxidative stress, reactive oxygen species (ROS) were monitored by flow cytometry in cells treated with $H_2$DCFDA which is cleaved to a fluorescent product by ROS, and treatment with $H_2O_2$ was used as a positive control. ROS were significantly induced in ES2 cells by RA371 and RA375 (FIG. 7C), although only RA375 induced significantly higher levels than RA190 ($p<0.01$). Similar results were seen in SKOV3 cells, and RA375 induced higher levels of ROS than RA190 or bortezomib (FIG. 8A). Unresolved UPR and ROS activate apoptosis in cancer cells, and annexin V-cell surface labeling was detected 12 hr after treatment of ES2 cells with 0.5 μM RA190 or 0.25 μM RA375 resulted in 38% and 50% cells undergoing apoptosis respectively (FIG. 7D). A similar phenomenon was observed with SKOV3 cells (FIG. 8B). Treatment of ES2 cells with RA371 and RA375 also induced rapid cleavage of Caspase 3, an apoptosis marker (FIG. 7E). Since RA375 is more potent in vitro, it was advanced for preliminary murine studies.

Safety and Pharmacodynamics of RA375

Initial toxicity testing was performed in female Balb/c mice with RA375. Groups of mice (n=3) were injected intra peritoneally (i.p.) with a single dose of RA375 (5, 10, 20, 40, 60, 100 mg/Kg in 25% β-hydroxypropyl cyclodextrin) and endpoints evaluated included clinical observation and body weight for one week. No adverse effects were noted with RA375 at even the highest dose. Administration of RA375 (40 mg/Kg, n=5) on alternate days for two weeks produced no observable toxicities or weight loss.

Figure 9:
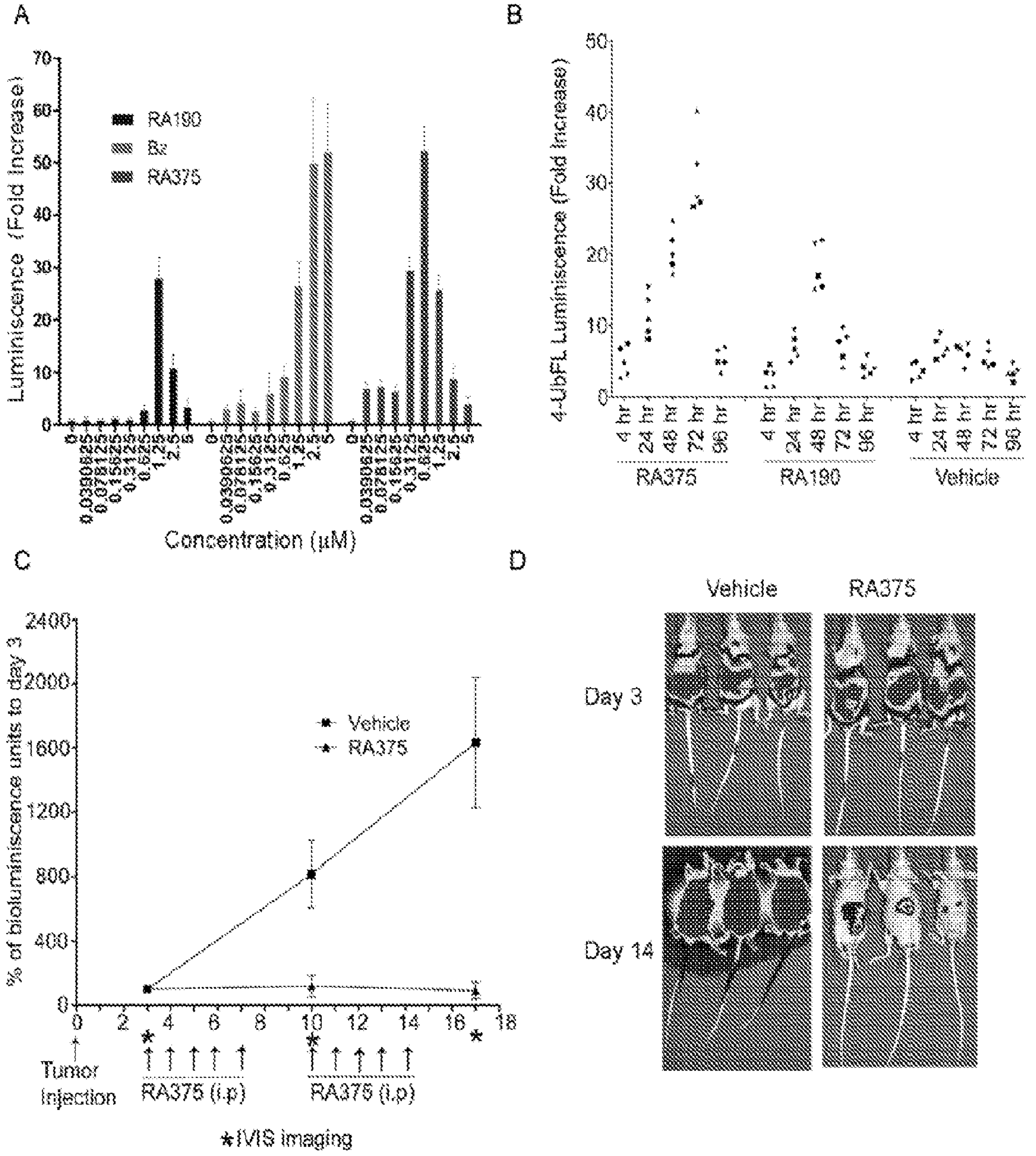
FIG. 9 illustrates RA375 inhibits proteasome function and reduces ovarian tumor burden in mice.

To monitor proteasome activity in living cells, a construct was used expressing a fusion protein comprising four tandem repeats of ubiquitin fused in frame with firefly luciferase (4UbFL) (41) to cause this otherwise stable reporter protein to undergo rapid proteolytic degradation via the proteasome. To assess their capacity to inhibit cellular proteasome function, 293T cells were transiently transfected with the 4UbFL construct and then 24 h later treated with compounds for 4 hours prior to assay of luciferase activity. Like bortezomib, RA375 induced a dramatic increase in bioluminescence, consistent with stabilization of 4UbFL, in a dose dependent manner. At very high concentrations the luciferase activity dropped because of cellular toxicity. RA375 was 2-fold more potent than bortezomib and 4-fold more potent than RA190 (FIG. 9A).

To test for proteasome inhibition by RA375 in vivo, an electroporation delivery was employed to transfect the leg muscle of mice with the 4UbFL reporter plasmid. After i.p. injection of luciferin, the enzymic activity of luciferase expressed by the 4UbFL DNA vector in the muscle tissue was visualized as bioluminescence using an IVIS imager. At two days post electroporation of the 4UbFL DNA, mice were imaged, and base line luminescence recorded. The control group (n=5) of mice was treated i.p. with vehicle alone and additional groups (n=5) treated i.p. with single 40 mg/Kg doses of RA375 or RA190 (FIG. 9B). After 4 h, 24 h, 48 h, 72 h and 96 h post treatment mice were again imaged, and bioluminescence was quantified. Stronger increases in bioluminescence were observed after treatment with RA375 than RA190 indicating greater inhibition of proteasome function in vivo (FIG. 9B).

Figure 10:
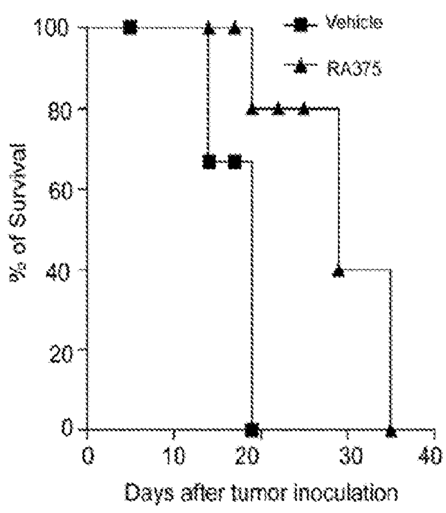
FIG. 10 illustrates RA375 treatment enhances survival of mice bearing ES2-luc xenograft. The experiment was performed as described in FIGS. 9C and 9D and the survival data was presented using Kaplan-Meier analysis and the statistical significance by the log rank test.

Therapeutic Effect of RA375 on Human Xenograft Model of Clear Cell Ovarian Carcinoma ES2 is a human cell line derived from a high grade ovarian clear cell carcinoma (42). The efficacy of RA375 against the ES2 xenograft model expressing luciferase (ES2-luc) was tested. Nude female mice were inoculated with ES2-luc cells into the peritoneal cavity. After 3 days the mice were imaged for their basal luminescence activity and randomized into two groups (n=8). One group was treated with the vehicle alone (25% β-hydroxypropyl-cyclodextrin solution in water) and the other group treated with RA375 (10 mg/Kg) daily for 5 days on treatment, two off, for 2 weeks. Mice were imaged after the first and second week of treatment for their luciferase activity to assess tumor burden. RA375 significantly reduced tumor burden (FIG. 9C-9D) without apparent weight loss or side effects and extended survival (p=0.04; FIG. 10).

Chirality

Rendering iRPN13s chiral and asymmetric through the addition of a single methyl to the core piperidone moiety can increase potency against cancer cell lines, and results in compounds of formula (I) shown below:

Formula (I)

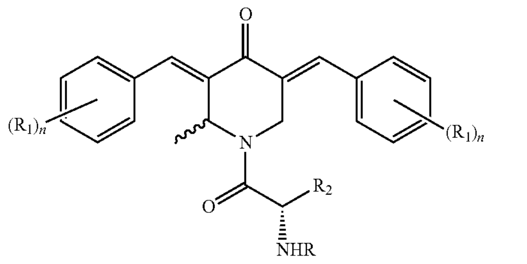

R in Formula (I) is defined as H, $C(O)CH_2Cl$, $C(O)CH_3$, $C(O)CH{=}CH_2$, or $C(O)N(H)CH_3$;

$R_1$ in Formula (I) is defined as halogen or nitro;

$R_2$ in Formula (I) is defined as side group from an alpha amino acid;

and n is defined as an integer from 0-5, inclusive, wherein the compound of formula (I) is not

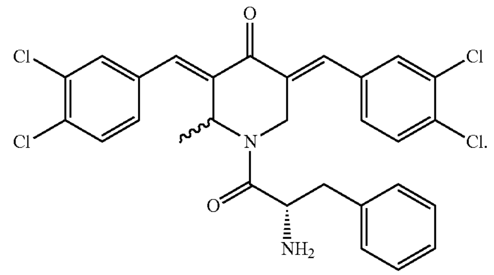 [SMILES: CC1/C(=C\c2ccc(Cl)c(Cl)c2)C(=O)/C(=C/c2ccc(Cl)c(Cl)c2)CN1C(=O)[C@@H](N)Cc1ccccc1]

A "side group from an alpha amino acid" is defined as the portion of an amino acid that does not include the adjacent amino and carboxylate functionalized carbons. For example, in RA413 the side group from an alpha amino acid (i.e. $R_2$) is the benzyl side group from phenyl alanine. In exemplary embodiments, R2 is benzyl (from phenylalanine), or 4-aminoethyl (from lysine).

In some embodiments, the phenyl ring substituents (i.e. $(R_1)_n$) are nitro, in particular 4-nitro, dichloro, in particular 3,4-dichloro, and fluoro, such as 2-fluoro or 4-fluoro.

In some embodiments, when $R_2$ is the phenylalanine side group and R is H, then $(R_1)_n$ is not 3,4-dichloro.

In some embodiments, the S-isomer is more active than the R-isomer. The enhanced cytotoxicities of these compounds are associated with improved binding to RPN13 in cell lysates, mitochondrial ATP depletion, oxidative stress and glutathione depletion, rapid accumulation of high molecular weight polyubiquitinated proteins with a consequent unresolved ubiquitin proteasome system (UPS) stress response. Cytotoxicity was associated with an early biomarker of apoptosis, increased surface annexin V binding. BRCA2 and ATM deficiency conferred increased sensitivity of cancer cell lines to these iRPN13s as well as cisplatin. Western blot analyses indicates that the DNA damage repair pathway may be disrupted by the iRPN13 due to the depletion of the nuclear pool of ubiquitin as it accumulates in the high molecular weight polyubiquitinated protein aggregates. Indeed, a synergistic cytotoxic response was evident upon combination treatment of the OVCAR3 ovarian cancer cell line with the DNA damaging agent cisplatin and the RPN13 inhibitor RA414, suggesting that this approach warrants further exploration for the treatment of ovarian cancer.

Figure 11:
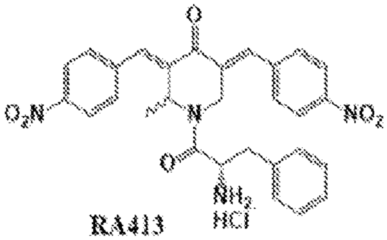
FIG. 11 illustrates the chemical structures of RA413, RA419, RA462, and RA467.
Figure 11:
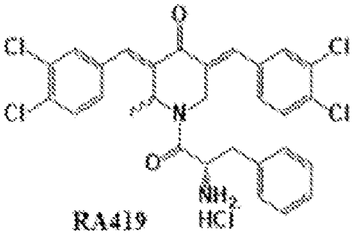
Figure 11:
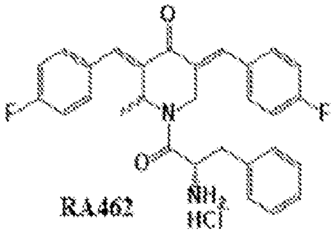
Figure 11:
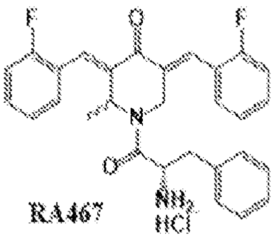
Figure 12:
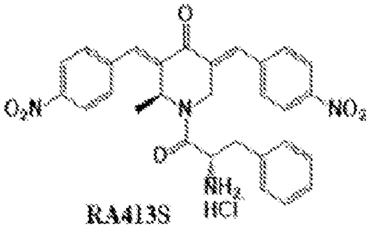
FIG. 12 illustrates the chemical structures of RA413S, RA413R, and RA414.
Figure 12:
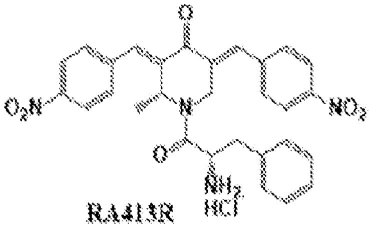
Figure 12:
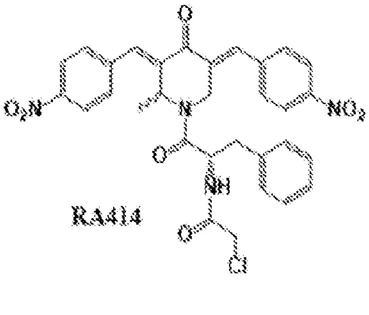

Optimization Strategy to Design Novel RPN13 Inhibitors:

In previous studies seeking to improve specificity, potency and solubility of candidate iRPN13s, several libraries of molecules were generated to probe the pharmacophore of the bis-benzylidinepiperidone core unit (10, 13). Preliminary molecular modelling data suggested that introducing asymmetry within the core unit might improve RPN13 binding. Based on these considerations, a methyl group was introduced at the piperidone ring carbon atom next to the nitrogen to render the molecule asymmetric and chiral. Several compounds were selected from the library and a methyl group was introduced (FIG. 11). All four racemic compounds were tested for cytotoxicity first in SKOV3, a human ovarian cancer derived cell line. RA413 was the most potent molecule in this series with an IC50 of 86 nM (Table 4A). While RA413 was similarly potent to its parental molecule, RA183, it was selected for further characterization and optimization. Since RA413 is racemic, each chiral form was synthesized, RA413S and RA413R (FIG. 12). Interestingly RA413S was 4-fold more cytotoxic for SKOV3 than RA413R (Table 3A). Cytotoxicity for normal cells (human foreskin fibroblasts (HFF), and prostate epithelial cells (PrEC) was minimal, with IC50 values >2500 nM, suggesting a robust therapeutic window.

Addition of the chloroacetamide to RA183 produces the more potent analog RA375. Likewise, addition of chloroacetamide to RA413 produced a highly potent mixed isomer RA414 (FIG. 12), with an IC50 of 3 nM for HeLa cells, compared to 23 nM for RA413S and 112 nM for RA183 (See Tables 1A-1C). The increase in potency conferred by the chloroacetamide warhead likely reflects soaking up intracellular GSH, as described for RA375.

TABLE 3A

Cytotoxicity induced by compounds of formula (I) drug treatments in diverse cancer cell lines as determined by MTT assay.

| | | Compound/cytotoxicity IC50 (nM) | | | | | | |
|---|---|---|---|---|---|---|---|---|
| BRCA status | Cell line name | RA413S | RA413R | RA413 | RA414 | RA462 | RA467 | RA375 |
| BRCA2 + VE | T22 | 1364 | | | | | | |
| BRCA2 − VE | BR5-FvB1 | 125 | | | | | | |
| BRCA2 − VE | BR5-Luc | 5.7 | | | | | | |
| BRCA2 + Ve | C2KmFvB1 | 550 | | | | | | |
| | HCT116 | 80 | | | 20 | | | 89 |
| | A2780 | 20 | | | 3.5 | | | 37 |
| | TOV21G | 3.6 | 20 | 42 | 1.1 | | | |
| | HeLa | 23 | 172 | 96 | 3 | | | 13 |
| | ID8-vegf | 60 | | 192 | <40 | 123 | 167 | 44 |
| | SKOV3 | 40 | 161 | 86 | <20 | 112 | 126 | 26 |
| | SKOV3-TR | 60 | | | <20 | | | 22 |
| | TC1-Lu | 114 | 1795 | | 40 | | | |
| | DLD1 | 164 | | | <40 | | 474 | 24 |
| BRCA2 − VE | DLD-BRCA2-Ve | 55 | | | <40 | | 502 | 18 |
| | DLD-Seckle | 55 | | | <40 | | | 43 |
| | RPE1 | 41 | | | <40 | | | 41 |
| | RPE1-ATMKO | 24 | | | <40 | | | |
| | SSC90 | 125 | | 312 | <20 | | | |
| | OVCAR3 | 69 | | | <20 | 105 | 120 | |
| | CasKi | 27 | 220 | | | | | 3 |
| | SiHa | 34 | 139 | | 7.5 | | | |
| BRCA1 + Ve | UWB1.289 + BRCA1 | | <20 | | | | | |
| BRCA1null | UWB1.289 | 43.9 | | | <20 | | | |
| | FaDu | 78 | | 300 | 78 | | | |
| | OV2008 | 40 | | 150 | | | | |
| | VU93 | 100 | | 625 | 40 | | | |
| | HS578T | 40 | | | 1.5 | | | |
| | MDA-MB-468 | 75 | | | <20 | | | |
| | MCF7 | 250 | | | 75 | 750 | 750 | |
| | HCC1395 | 75 | | | <15 | 250 | 250 | |
| | SUM1315 | 258 | | | 20 | | | 19 |
| | SUM149 | 20 | | | <20 | | | |
| | PEA1 | 70 | | | 30 | | | |
| | PEA2 | 64 | | | 30 | | | 60 |
| | PEO1 | 31 | | | 30 | | | 27 |
| | PEO4 | 41 | | | 30 | | | |
| | PEO14 | 92 | | | 30 | | | |
| | ES2 | 40 | | | 7.5 | 96 | 112 | |
| | HEC-1A | 207 | 268 | | 196 | | | |
| | KLE | 1458 | 1433 | | 1120 | | | |
| | LNCAP | | | | 24 | | | |
| | DU145 | | | | 17 | | | |
| | PC3 | | | | 12 | | | |

TABLE 4B

Cytotoxicity induced by related compound drug treatments in diverse cancer cell lines as determined by MTT assay.

| | | Compound/cytotoxicity IC50 (nM) | | | | |
|---|---|---|---|---|---|---|
| BRCA status | Cell line name | RA190 | RA183 | RA419S | RA415 | RA411 |
| BRCA2 + VE | T22 | 16325 | | 1541 | | |
| BRCA2 − VE | BR5-FvB1 | 250 | | 250 | | |
| BRCA2 − VE | BR5-Luc | 38 | | 41.2 | | |
| BRCA2 + Ve | C2KmFvB1 | 436 | | 206 | | |
| | HCT116 | 239 | 193 | | | |
| | A2780 | 139 | 161 | | | |
| | TOV21G | 148 | 53 | | | |

TABLE 4B-continued

Cytotoxicity induced by related compound drug treatments in diverse cancer cell lines as determined by MTT assay.

| | | Compound/cytotoxicity IC50 (nM) | | | | |
|---|---|---|---|---|---|---|
| BRCA status | Cell line name | RA190 | RA183 | RA419S | RA415 | RA411 |
| | HeLa | 85 | 112 | 173 | | 16 |
| | ID8-vegf | 211 | 198 | | 274 | |
| | SKOV3 | 73 | 54 | | | 257 |
| | SKOV3-TR | 109 | 77 | | | |
| | TC1-Lu | | | 274 | | |
| | SSC90 | 625 | | | 80 | |
| | OVCAR3 | 120 | 78 | | | |
| | CasKi | 324 | 312 | 153 | | |
| | SiHa | 603 | 263 | | | |
| | FaDu | 300 | 150 | | | |
| | OV2008 | | 80 | | | |
| | VU93 | 625 | | | 150 | |
| | HS578T | 78 | 89 | | | |
| | MDA-MB-468 | 300 | 250 | | | |
| | MCF7 | 750 | | | | |
| | HCC1395 | 0.35 | | | | |
| | SUM1315 | 1370 | | | | |
| | SUM149 | 233 | | | | |
| | PEA1 | 386 | | | | |
| | PEA2 | 396 | | | | |
| | PEO1 | 232 | | | | |
| | PEO4 | 168 | | | | |
| | PEO14 | 375 | | | | |
| | ES2 | 115 | 75 | | | |
| | HEC-1A | 431 | 378 | | | |
| | KLE | 1593 | 989 | | | |
| | LNCAP | 242 | 186 | | | |
| | PC3 | 162 | 133 | | | |

TABLE 4C

Cytotoxicity induced by existing compound drug treatments in diverse cancer cell lines as determined by MTT assay

| | | Compound/cytotoxicity IC50 (nM) | | | | | | | |
|---|---|---|---|---|---|---|---|---|---|
| BRCA status | Cell line name | VLX1570 | CP | OLA | BZ | DOX | Vin | Carf | Top |
| BRCA2 − VE | BR5-FvB1 | 250 | 2500 | 30 | <20 | <20 | | | |
| BRCA2 − VE | BR5-Luc | 4.8 | 332 | 500 | 4.1 | 237 | | | |
| BRCA2 + Ve | C2KmFvB1 | 572 | 7593 | 7961 | 3.2 | 27 | 13.4 | 8.2 | 666 |
| | A2780 | | | | 3 | | | | |
| | HeLa | 111 | | | 3 | | | | |
| | ID8-vegf | | | | 1.5 | | | | |
| | SKOV3 | 128 | | | 1.5 | | | | |
| | SKOV3-TR | 300 | | | | | | | |
| | TC1-Lu | | | | 4.5 | | | | |
| | DLD1 | | 24790 | 23000 | 4.8 | | | | |
| BRCA2 − VE | DLD-BRCA2-Ve | | 8540 | 1869 | 2.5 | | | | |
| | DLD-Seckle | | 964 | 14000 | 1.7 | | | | |
| | RPE1 | | 2086 | 23200 | 3.5 | | | | |
| | RPE1-ATMKO | | 963 | 111 | 2.6 | | | | |
| | SSC90 | | | | 15 | | | | |
| | OVCAR3 | 18 | 3034 | | 30 | | | | |
| | CasKi | 68 | | | | | | | |
| | SiHa | 54 | | | | | | | |
| BRCA1 + Ve | UWB1.289 + BRCA1 | | | 994 | | | | | |
| BRCA1null | UWB1.289 | | | 581 | | | | | |
| | VU93 | | | 30 | | | | | |
| | HS578T | | | | 13 | | | | |
| | HCC1395 | | 250 | 750 | | | | | |
| | SUM149 | | | | 30 | | | | |
| | PEA1 | | 7519 | | 30 | | | | |
| | PEA2 | | 9846 | | 30 | | | | |
| | PEO1 | | 7990 | | 31 | | | | |
| | PEO4 | | 19470 | | 31 | | | | |
| | PEO14 | | 1378 | | 30 | | | | |

TABLE 4C-continued

| Cytotoxicity induced by existing compound drug treatments in diverse cancer cell lines as determined by MTT assay | | | | | | | | | |
|---|---|---|---|---|---|---|---|---|---|
| | | Compound/cytotoxicity IC50 (nM) | | | | | | | |
| BRCA status | Cell line name | VLX1570 | CP | OLA | BZ | DOX | Vin | Carf | Top |
| | HEC-1A | | 1342 | | 153 | | | | |
| | KLE | | | | 1192 | | | | |

(CP = Cisplatin; OLA = olaparib; BZ = bortezomib; DOX = Doxorubicin; Vin = Vincristine; Carf = Carfilzomib; Top = Topotecan)

Figure 13:
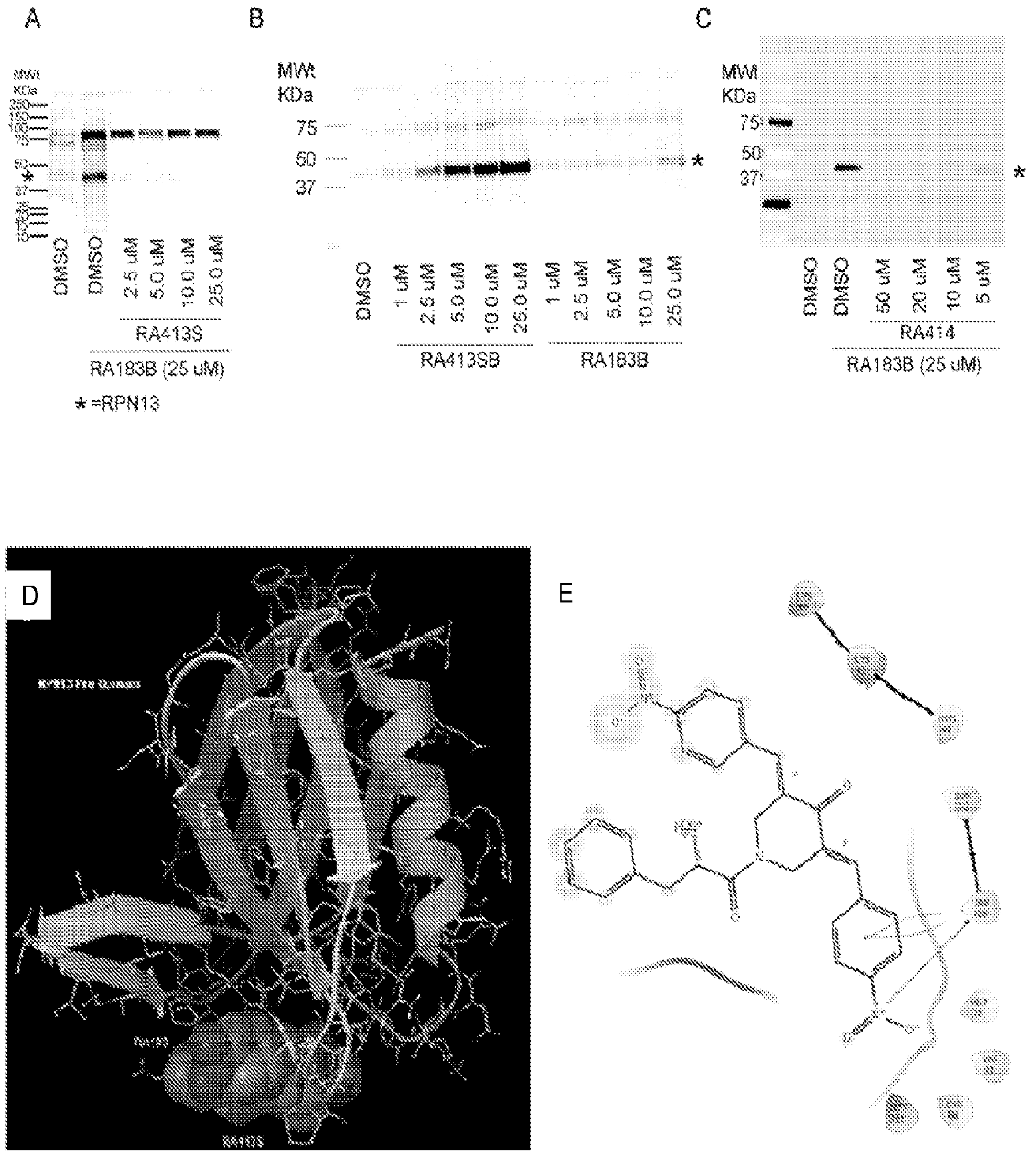
FIG. 13 illustrates the testing and modeling of drug binding to RPN13. After treatment samples were separated by SDS-PAGE and transferred to a PVDF membrane which was probed with HRP-streptavidin to detect biotinylated proteins. Docked complexes of RA molecules and the RPN13 Pm Domain were done in the Schrodinger glide application. Pink lines represent hydrogen bonds, green lines represent π-π interactions.
Figure 13:
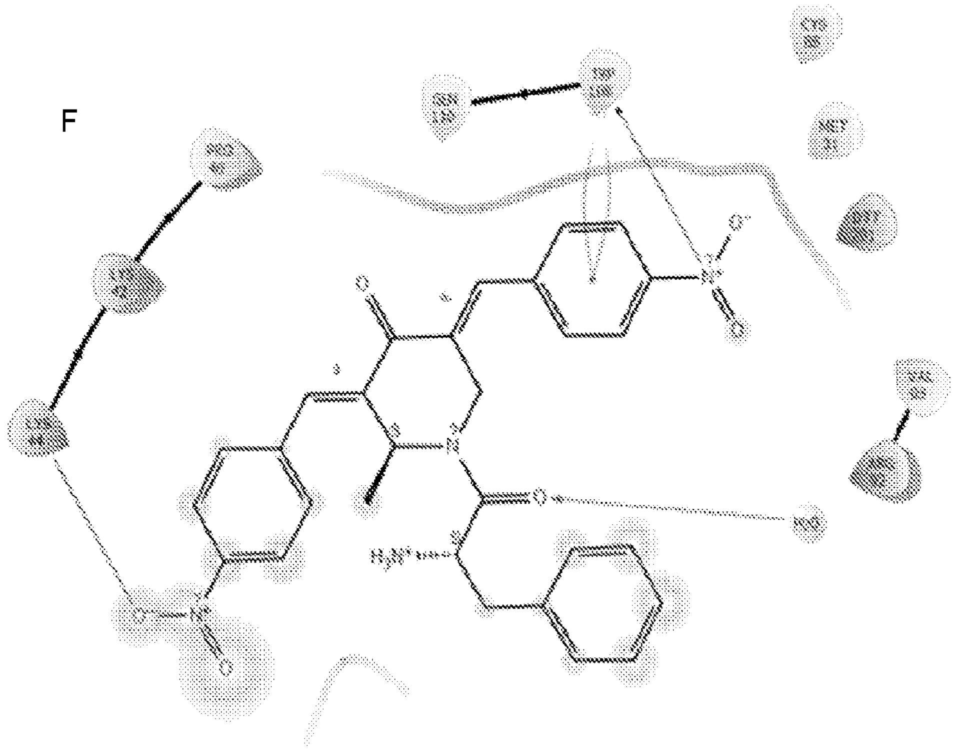
Figure 13:
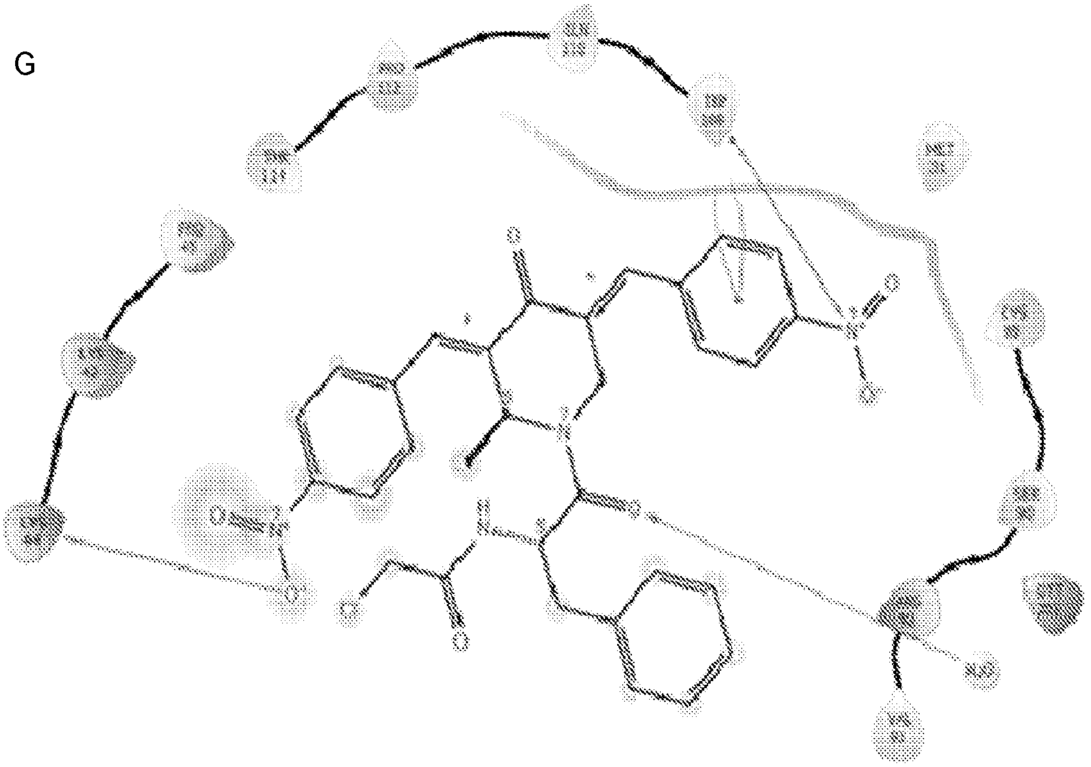

RPN13 Binding:

It has been shown preciously that RA183 adducts Cysteine 88 of RPN13 (13). To examine whether RA413S and RA414 bind similarly to RPN13, competition assays were performed using biotinylated RA183 (RA183B) as a probe (FIG. 13A). Briefly, SKOV3 cell lysate was pre-treated with different concentrations of RA413S and then labelled with RA183B. Samples were subjected to SDS-PAGE and transferred to a PVDF membrane. The membrane was probed with HRP-Streptavidin antibody, and the blot developed using chemiluminescence. Imaging revealed that the binding of RA183B to RPN13 was competed by RA413S in a dose dependent manner, suggesting that they bind the same cysteine 88 residue (FIG. 13A).

Biotinylated RA413S (RA413SB) was synthesized and its binding to RPN13 assessed. A direct labelling assay in cell lysate of ES2, a human ovarian cancer-derived cell line, using RA413B and RA183B was performed. Binding of RA413SB to RPN13 was substantially stronger than for RA183B, consistent with the higher potency of RA413S than RA183 in cytotoxicity assays (FIG. 13B). Binding of RA183B to the 42 kDa cellular protein is inhibited by pre-incubation with RA414, suggesting that it also adducts Cysteine 88 of RPN13 (FIG. 13C).

To further explore binding of the compounds to RPN13, molecular modeling studies were performed using Schrodinger software. In the docking studies, RA414 showed a superior Glide Score of −5.43 kcal/mol, with a good binding energy value of (MMGBSA) −49.69 kcal/mol. RA413S exhibited an intermediate Glide Score of −3.70 kcal/mol and a binding energy value of (MMGBSA) −35.96 kcal/mol. Finally, RA183 had the weakest Glide Score of −2.87 kcal/mol and a binding energy value of (MMGBSA) −34.18 kcal/mol. This modeling suggests additional hypotheses to account for the relative RPN13 binding and potencies in cytotoxicity assays of RA414, RA413S and RA183 (FIG. 13D).

Figure 14:
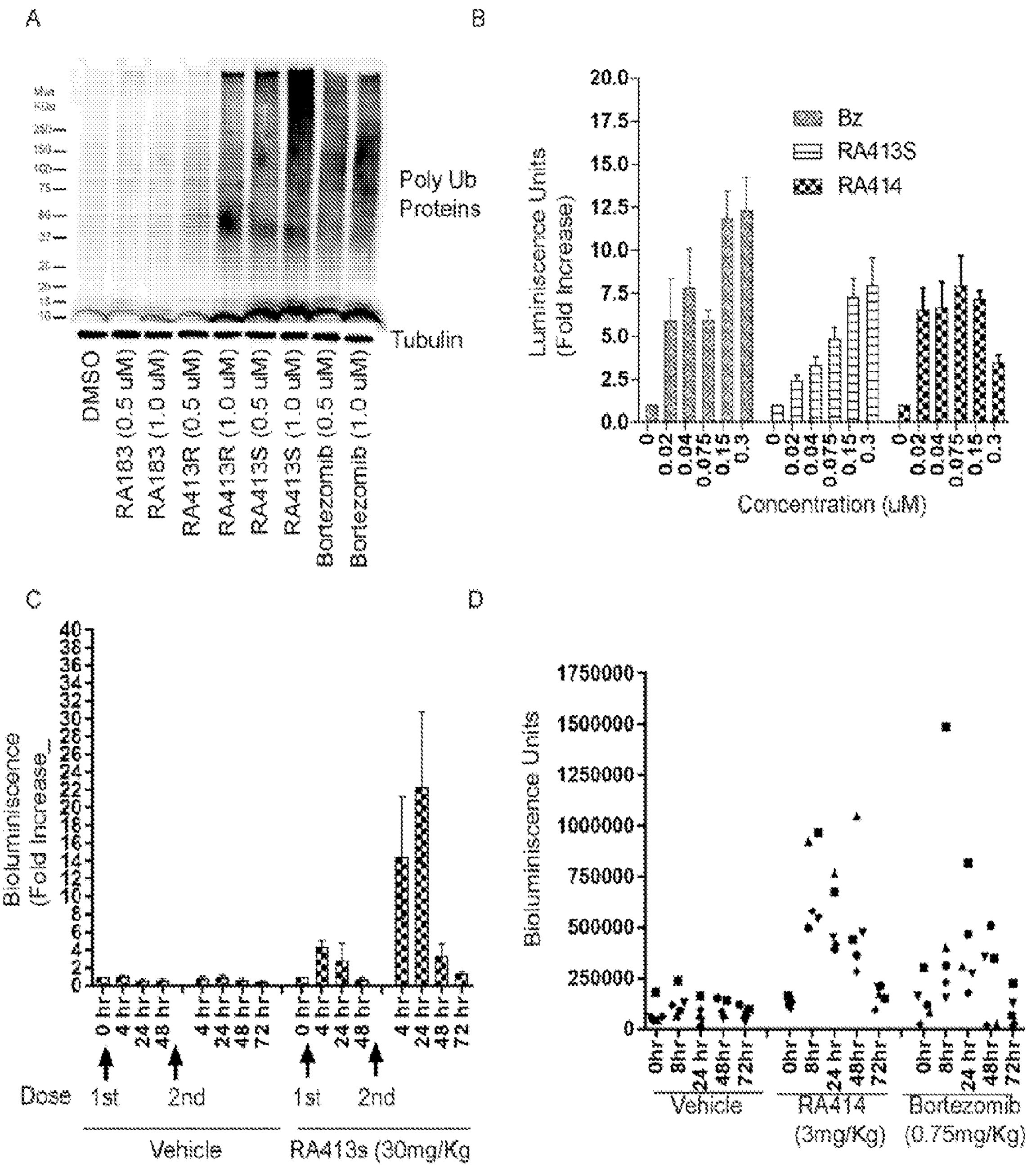
FIG. 14 illustrates compounds inhibiting proteasome function and possess on target activity in vivo.
Figure 21:
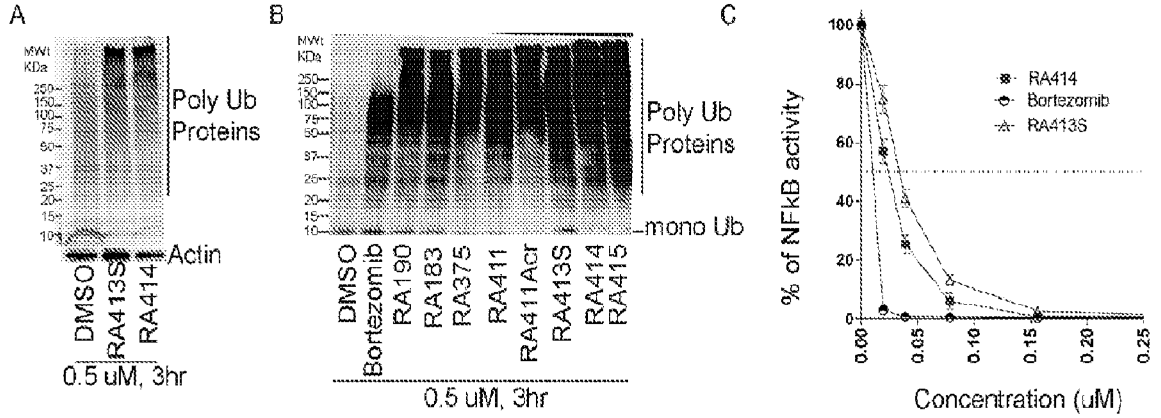
FIG. 21 illustrates high molecular weight polyubiquitinated protein accumulation measured by Western blot analysis using anti-ubiquitin monoclonal antibody.

The effect of RA413S and RA414 on proteasome function was examined in ovarian cancer cell lines in comparison with RA183, RA190, RA375 and bortezomib. All enhanced the accumulation of polyubiquitinated proteins in SKOV3 cells (FIG. 14A). Treatment of SKOV3 with the candidate iRPN13 compounds enhanced the accumulation of the highest molecular weight polyubiqitinated proteins that did not fully enter the gel. Notably, RA413S was more potent compared to its R isomer and parent compound RA183 in triggering this accumulation (FIG. 14A). Similar results were obtained in HeLa cells derived from a human cervical cancer, and in the human colon cancer cell line HCT116 with RA413S and RA414 (FIGS. 21A & 21B).

Activation of NF-κB is regulated by IκB proteins. IκB-α ubiquitination and degradation is an important step for the nuclear localization of NF-kB and activation of its transcriptional program. It was previously observed that RA183 inhibits this signaling pathway with an IC50 of 0.1 μM (13) as determined using 293T cells stably expressing NFkB-Luc reporter. Using the same system showed dose dependent decrease in NF-κB activity with RA413S that was more potent than for RA183, and RA414 was more active than RA413S (FIG. 21C).

Next examined was the effect of compounds on proteasome function using a DNA construct that expresses a reporter gene comprising firefly luciferase fused to four molecules of ubiquitin (4UbFL) at its amino terminus (41). The 4UbFL is rapidly degraded by active proteasomes, resulting in a low level of enzymic activity and bioluminescence. Upon proteasome inhibition, increased 4UbFL activity can be measured by luminescence assay using luciferin as a substrate as the protein is stabilized. Treatment of ES2 cells stably expressing 4UbFL with RA413S and RA414 increased bioluminescence in a dose dependent manner. The concentration dependence was consistent with the IC50 of the compounds, but was measured at 4 h, well before the onset of cell death (FIG. 14B).

Pilot safety studies were performed in CD1 mice (n=3/dose group of healthy female mice aged 6-8 weeks) with increasing single doses delivered i.p. and the NOAEL (no-observed-adverse-effect level) was selected for further animal studies. Intraperitoneal administration of RA413S was tolerated at 30 mg/Kg without weight loss or any other clinically noticeable toxicities, whereas the NOAEL for RA414 was 3 mg/Kg. Bortezomib was dissolved in a minimal amount of DMSO and further diluted with saline before injection in a dose finding study. An NOAEL of 0.75 mg/Kg was identified for bortezomib via this route. To measure on-target inhibition of proteasome activity in mice, a leg muscle of CD-1 mice was transduced with the 4UbFL reporter construct. The time course of stabilization of 4UbFL expressed in the muscle tissue after delivery of a single dose of RA413S or RA414 by i.p. injection was followed using an IVIS200 imager. Briefly, mouse leg muscle was electroporated with 4UbFL plasmid and basal bioluminescence was measured after 24 hr using IVIS200 imager after injecting luciferin substrate. Mice were randomized (n=5/group) and treated with compounds in PEG400: Cremophor: Tween40 combination or vehicle alone as shown in Table 5 with one dose delivered by intraperitoneal injection. The mice were again imaged at 4 h, 24 h, 48 h post treatment. The RA413S treatment group exhibited a 4-6 fold increased bioluminescence at 4 h and 24 h, that returned to basal levels by 48 hr. At the 72 hr time point another dose of RA413S formulated in b-HPCD was administered by i.p. injection, and the mice were again imaged at 4, 24, 48, and 72 hr. RA413S increased the bioluminescence by 14-22 fold at 4 hr and 24 hr later, and this returned to the basal level by 72 hr. This data indicates on-target activity of the compounds in vivo, and this pharmacodyanmic study informs the design of a dosing regimen for tumor treatment studies. RA413S formulated in b-HPCD (β-hydroxy propyl cyclodextrin) shows higher and longer on-target activity compared to the PEG400: Cremophor: Tween40 formulation (FIG. 14C). Based on these observations the b-HPCD formulation was selected for RA413S. RA414 was soluble in the PEG system only, but it possessed on-target activity over 72 hr similar to bortezomib. These data suggest an every third day dosing regimen is appropriate for RA413S, RA414, and bortezomib by intraperitoneal delivery.

TABLE 5

Dosing regimen of compounds and IVIS imaging schedule (bHPCD = beta-hydroxypropyl cyclodextrin)

| Compound | $1^{st}$ dose (ip) | Mice (n = 5) | Formulation | IVIS schedule (hours) | $2^{nd}$ dose (ip) | Formulation | Imaging schedule |
|---|---|---|---|---|---|---|---|
| Vehicle | | CD1 | PEG400: Cremophor: Tween40 | 0, 4, 24, 48 | | 25% bHPCD | 0, 4, 24, 48, 72 |
| RA413S | 30 mg/kg | CD1 | PEG400: Cremophor: Tween40 | 0, 4, 24, 48 | 30 mg/kg | 25% bHPCD | 0, 4, 24, 48, 72 |
| RA414 | 3 mg/kg | CD1 | PEG400: Cremophor: Tween40 | 0, 4, 24, 48, 72 | | | |
| Bortezomib | 0.75 mg/kg | CD1 | DMSO and Saline | 0, 4, 24, 48, 72 | | | |

Mitochondrial Effects of RA413S Treatment:

Bortezomib reduces mitochondrial membrane potential, PINK1/Parkin mitophagy gene expression levels, and caused perinuclear clustering of mitochondria, yet it changes neither mitochondrial dynamics nor mitophagy rate (64). Parkin plays an important role in regulating the clearance of mitochondrial proteins during mitophagy and this mitochondrial E3 ubiquitin ligase is recruited to the proteasome via RPN13 (60), suggesting mitochondrial function may be impacted by iRPN13. MitoTracker is a commercially available fluorescent dye that covalently br5Mitotracker to stain HeLa cells after RA413S treatment for 18 hr, mitochondrial depolarization was evident over time as a weaker signal visualized by fluorescent microscopy (FIG. 15A) as well as the perinuclear clustering of mitochondria previously seen with bortezomib (64). Similar results were obtained with RA413S treatment in a murine ovarian cancer model cell line BR5 (74) although the effects were less prominent (FIG. 15B), consistent with its lower sensitivity to RA413S (Table 3A).

To assess the effect of RA413S treatment on mitochondrial electron transport chain (ETC) dysfunction, ATP production was analyzed using a luciferase-based assay for ATP-dependent production of bioluminescence using luciferin as substrate. Briefly, firefly luciferase expressing ES2 cells were treated for 4 hr with compounds at sublethal doses and the bioluminescence was measured in intact cells using luminometer by adding luciferin. A reduced bioluminescence with RA183 and RA413S was observed, indicating reduced intracellular ATP levels. Surprisingly, this was not evident with bortezomib treatment (FIG. 15C) as bortezomib produces mitotoxicity, reducing ATP production in neuronal cells (75). This is associated with enhanced glycolysis while bortezomib suppresses oxidative phosphorylation (OXPHOS) (66).

Figure 15:
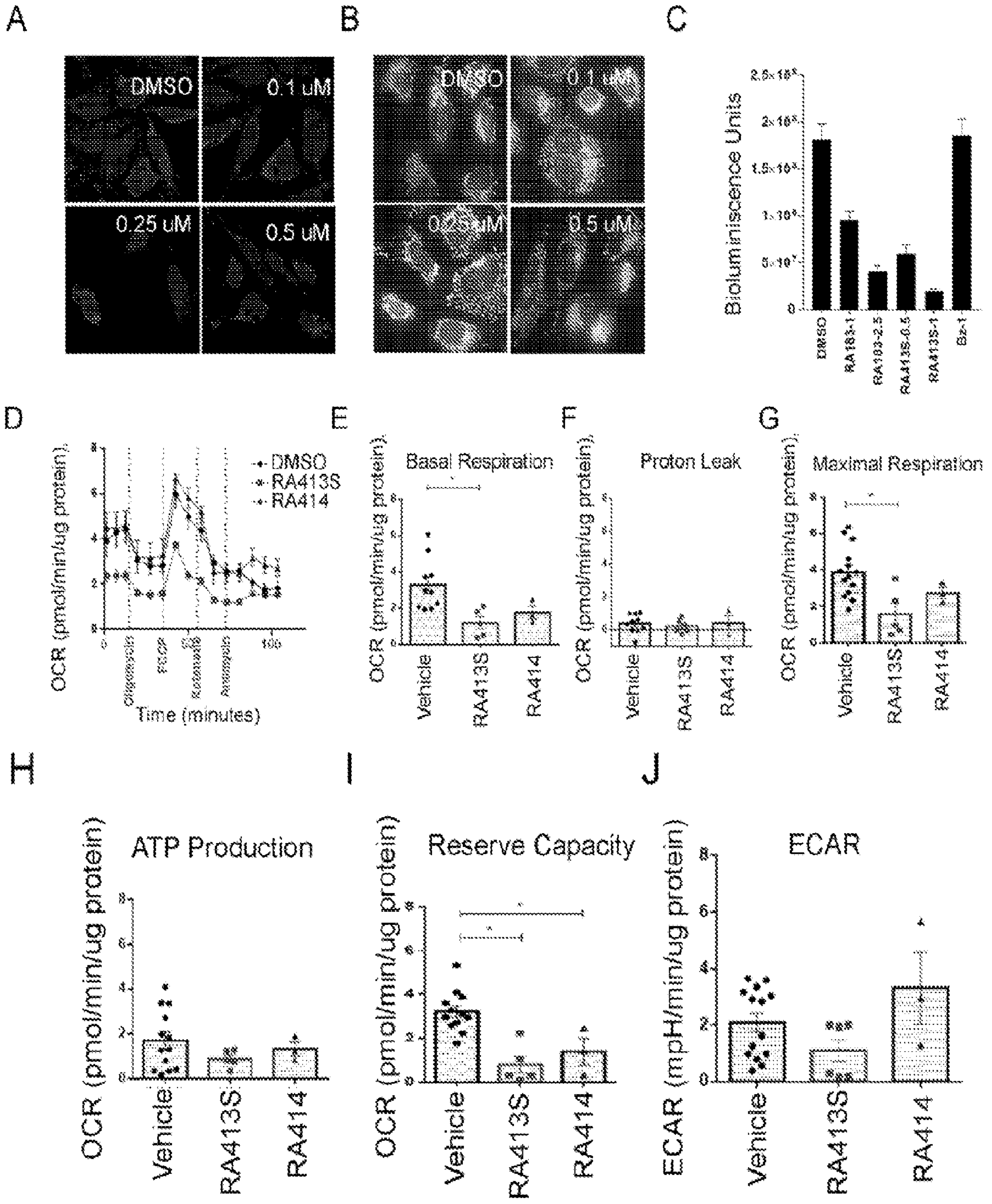
FIG. 15 illustrates RA413S induces mitochondrial damage and alters cellular bioenergetics. Cells were fixed and stained with MitoTracker (red [A]/yellow [B] pseudocoloring and Hoechst (blue)). Fragmented mitochondria is visible in RA413S treated samples. RA183 and RA413S treatment caused reduction of ATP-dependent luminescence after addition of luciferin in a seahorse assay in ES2 cells upon treatment with RA413S (100 nM) and RA414 (100 nM) or vehicle (DMSO) for 12 hr.

Since RA413S appears to impact mitochondrial function, a Seahorse XF flux analyzerwas used to measure oxygen consumption rate (OCR) as a measure of OXPHOS, and extracellular acidification rates (ECAR) as a measure of lactate production by glycolysis in a microplate, in real-time using multiple conditions per assay well using ES2 cells. During the mitochondrial stress test, baseline OCR measurements were followed by the addition of the compound oligomycin to measure ATP-linked respiration. Upon addition of the uncoupler FCCP, maximal respiration is measured. Maximal respiration was significantly reduced in ES2 cells treated with RA413S relative to the vehicle or RA414-treated groups (FIG. 15G). At the end of the assay, a mix of rotenone and antimycin A was injected to provide a measure of non-mitochondrial respiration. This analysis demonstrated that RA413S suppressed oxidative phosphorylation rates in ES2 cells. The reduction in OXPHOS should result in cells utilizing glycolysis to produce the energy they need. To determine the impact of RA413S on glycolysis, ES2 cells were incubated in medium without glucose or pyruvate and the baseline ECAR was measured. Addition of glucose allows the measurement of the glycolysis rate. This was followed by the injection of oligomycin which inhibits mitochondrial ATP production and shifts the energy production to glycolysis. The consequent rise in ECAR measures the cellular maximum glycolytic capacity. ES2 cells treated with RA413S displayed a significant decrease in their glycolytic capacity relative to the vehicle-treated group. Thus, ES2 cells demonstrated significant reduction in OXPHOS, glycolysis and ATP production with RA413S treatment but surprisingly not with RA414 (FIG. 15D).

Figure 16:
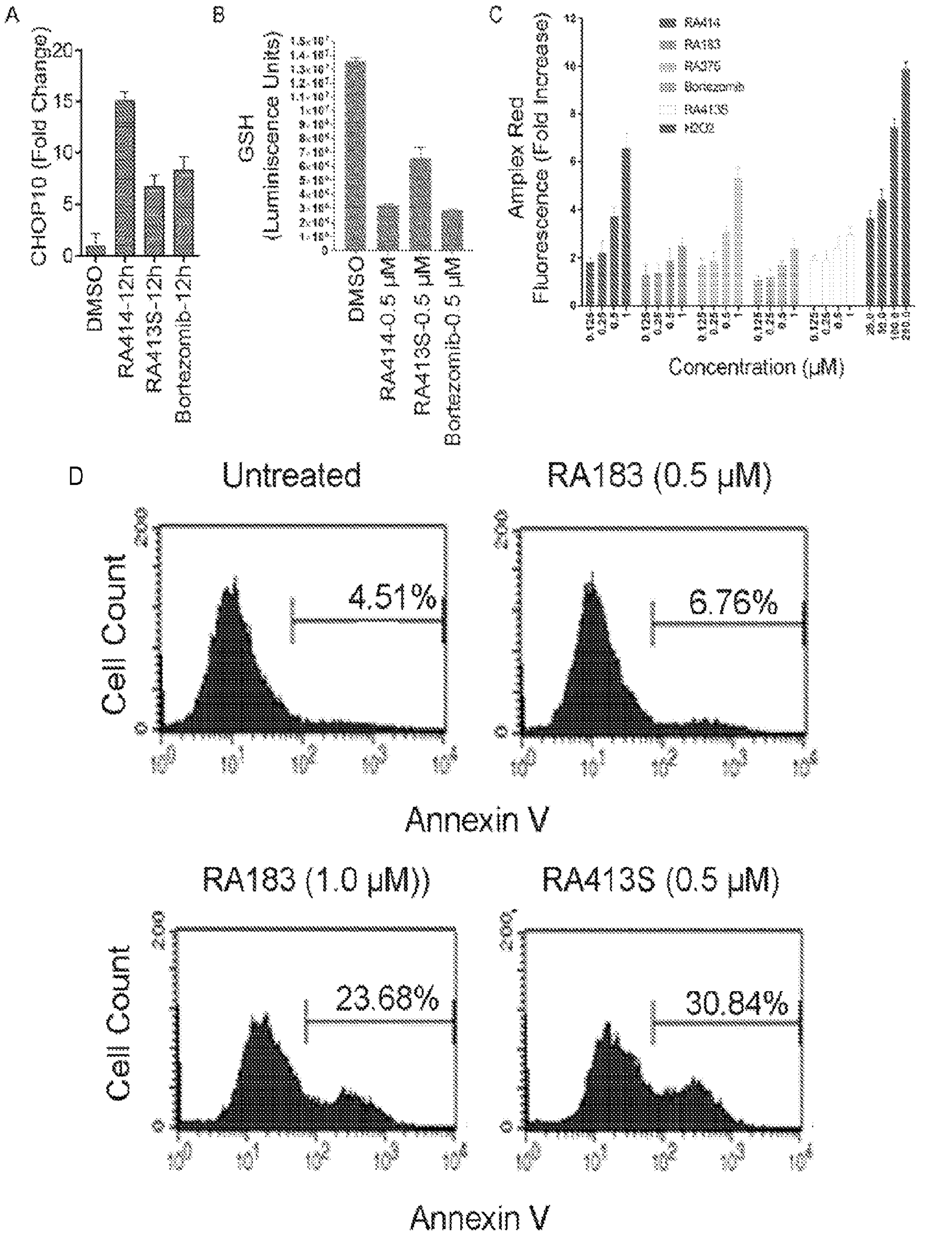
FIG. 16 illustrates RA413S and RA414 induce ER and oxidative stress in ES2 cells triggering their apoptotic cell death.
Figure 22:
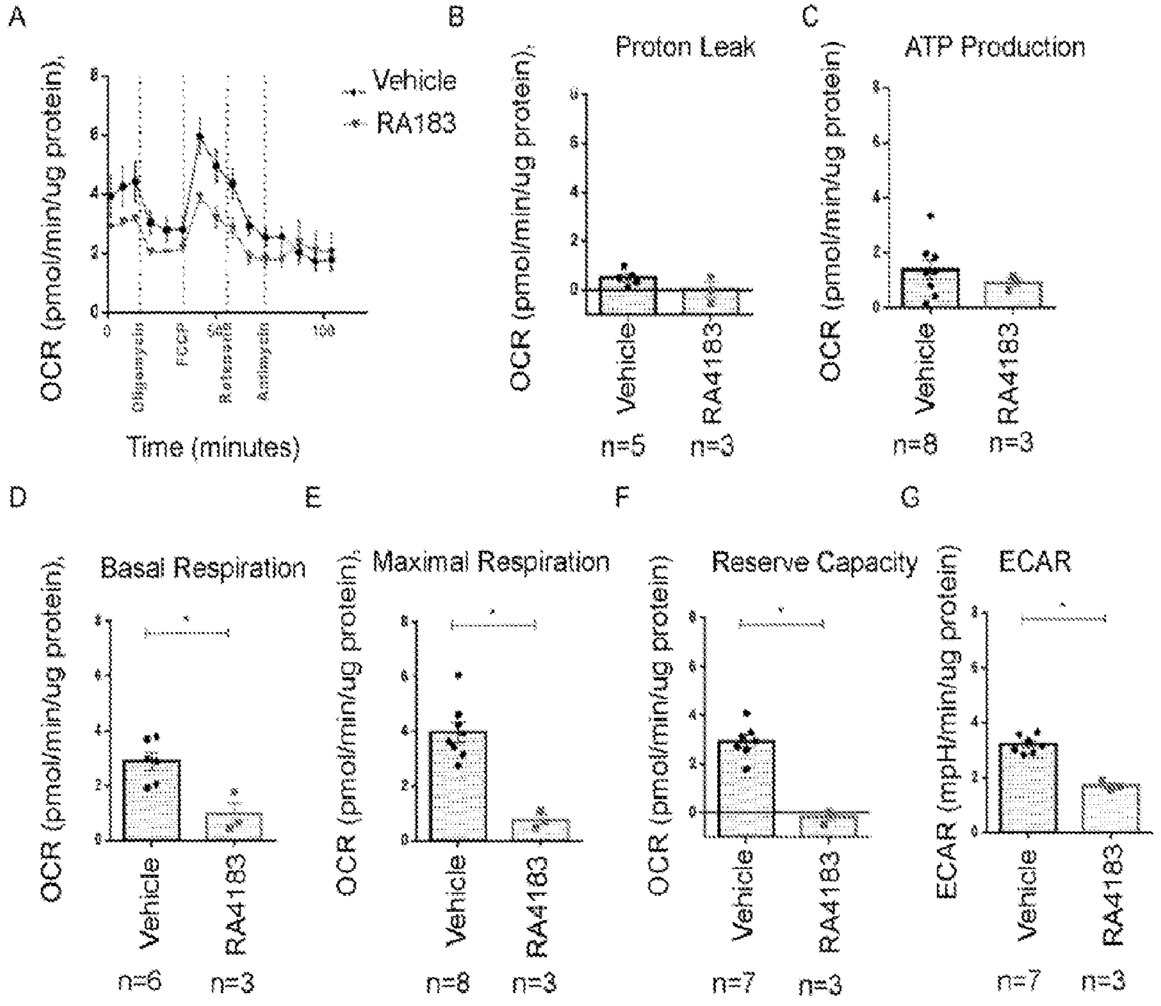
FIG. 22A illustrates the effect of RA183 on cellular bioenergetics in a Seahorse assay in ES2 cells upon treatment with 250 nM of RA183 or vehicle (DMSO) for 12 hr.
FIG. 22B illustrates proton leak induced by RA183 or vehicle for 12 hr.
FIG. 22C illustrates the effect of RA183 or vehicle on ATP production.
FIG. 22D illustrates the effect of RA183 or vehicle on basal respiration.
FIG. 22E illustrates the effect of RA183 or vehicle on maximal respiration.
FIG. 22F illustrates the effect of RA183 or vehicle on reserve capacity.
FIG. 22G illustrates the effect of RA183 or vehicle on ECAR.

Consistent with the luciferase-based assay of intracellular ATP levels (FIG. 15C), an almost 4-fold decrease of ATP production was observed after 12 hr of RA413S treatment (FIG. 15H). This ATP production is a reflection of mitochondrial oxygen consumption rate. As shown in FIG. 15D, RA413S treatment for 12 hr significantly decreases overall oxygen consumption in the Seahorse mitochondrial stress test, most notably the basal respiration rate (FIG. 15E) as well as the maximal respiration rate (FIG. 15F), but reduction of ATP production did not reach significance (FIG. 16G). Likewise, a reduction of basal respiration rate (FIG. 15F), and maximal respiration rate (FIG. 15F) was observed with RA414 but it did not reach significance. ETC inhibition by RA413S and RA414 significantly reduced the cellular energy reserve in ES2 cells, which is essential for maintaining cellular function (FIG. 15I). A trend of downnregulation of intracellular pH change (ECAR) after 24 hr RA413S treatment was also observed (FIG. 15J), although this was not seen with RA414. As ECAR is the direct denominator of glycolysis, the data suggest that RA413S treatment may also inhibit glycolysis in ES2 cells. Taken together, RA413S treatment affects ES2 cancer cells in multiple pathways; i) inhibition of glycolysis in the cytoplasm, and ii) inhibition of the mitochondrial ETC. Both the pathways ultimately reduce ATP production. Similar patterns were observed in ES2 cells with the treatment of RA183 (FIG. 22), suggesting that it also acts like RA413S to starve the cancer cells of their energy source, but RA414 may act differently.

Figure 23:
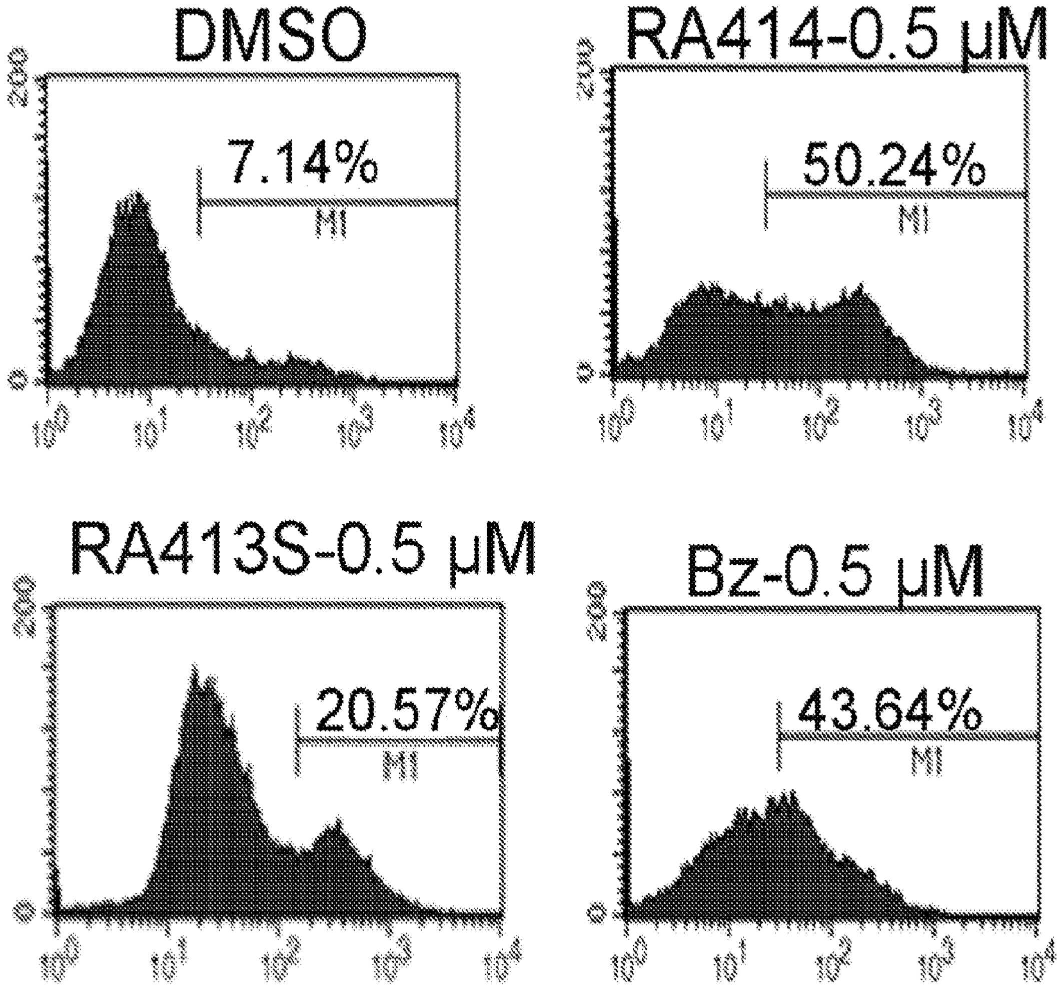
FIG. 23 illustrates SKOV3 cells treated with compounds at indicated doses for 12 hr then re-suspended in 100 μL binding buffer with 5 μL of Annexin V-PE and 5 μL of 7-AAD. After a 15 min incubation at RT, the cells were analyzed by flow cytometry using a FACSCalibur and CellQuest software.

Altered Oxidative Stress Causes Apoptosis in Cancer Cells with Compounds Treatment Recent insights indicate that ER stress and oxidative stress are highly interrelated biological process which regulate a wide range of signaling pathways in cells. ROS generation plays a critical role in the initiation of proteasome inhibitor induced apoptotic cascade (65). Oxidative stress is characterized by an imbalance between the production of ROS and the availability of free GSH. Generation of ROS is considered an early event in the process of apoptotic cell death (68). To counteract ROS, cells upregulate antioxidant pathways including intracellular glutathione (GSH). GSH is the most abundant intra cellular non-protein thiol and it can reduce the potency of iRPN13s. Conversely, iRPN13s reduce GSH upregulation and increase cellular ROS. Thus the impact of RA413S and RA414 on an ER stress marker, CHOP10 mRNA, was determined by RT-PCR, GSH levels were measured using a fluorometric GSH assay kit, ROS by Amplex Red assay and as a biomarker of early apoptosis, and surface Annexin V staining was measured by flow cytometry. As expected bortezomib, RA413S, and RA414 each significantly increased CHOP10 transcript levels (FIG. 16A), and reduced intracellular GSH concentrations (FIG. 16B). RA414, RA375, RA413S, RA183, and bortezomib, in order of potency, raised the level of ROS in a dose-dependent manner (FIG. 16C). Further, RA413S more potently activated a biomarker of early apoptosis, and surface display of Annexin V, than RA183 (FIG. 16D). Results were observed in another ovarian cancer cell line, SKOV3, that further suggested that RA414 is more potent for inducing cell killing than RA413S (FIG. 23). In sum, these findings indicate that the induction of cellular and mitochondrial ROS upon RA183, RA413S, or RA414 treatment contributes to their cytotoxicity.

In Vivo Therapeutic Efficacy of RA413S and RA414 Against Syngeneic and Xenograft Mouse Models of Ovarian Cancer The maximum tolerated dose (MTD) was tested in an effective preclinical dose determination strategy, of both RA413S and RA414 in groups of 3 healthy female CD1 mice (4-6 weeks old) per dose level using >10% weight loss and/or the emergence of clinically unacceptable symptoms as end points. The starting doses were based on previous studies with RA183. Doses were escalated incrementally in steps of not more than 50%. When either of these endpoints was met, dose escalation was halted and the prior dose was set as the MTD. Next determined was the effect of 3 repeated doses of each compound every third day in healthy female CD1 mice and repeat dose MTDs of 20 mg/kg for RA413S and 10 mg/kg for RA414 were identified.

Figure 17:
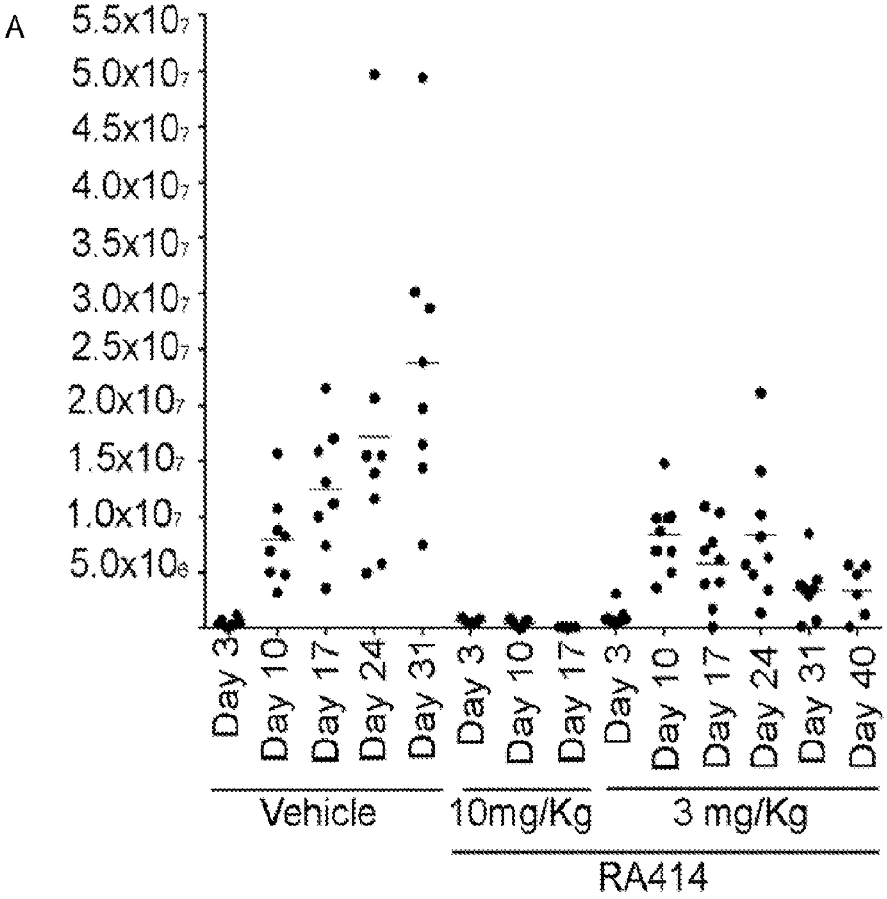
FIG. 17 illustrates tumor growth inhibition and on-target effect of RA414 in a syngeneic mouse model of ovarian cancer.
Figure 17:
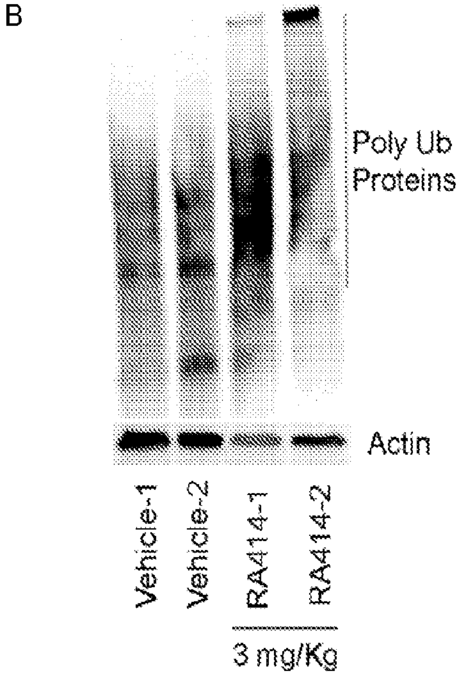

To assess therapeutic efficacy the ID8-VegfDefb29 cell line was utilized in a syngeneic mouse model of ovarian cancer expressing luciferase (62). ID8 was first derived from spontaneous malignant transformation of C57BL/6 mouse ovarian surface epithelial cells in vitro (69). ID8-Vegf Defb29 cells represent a more aggressive variant of ovarian cancer in which VEGF provides vascular growth which is augmented by the presence of DEFB29 (62). C57BL/6 mice were injected i.p. with ID8-VegfDefb29 cells stably expressing firefly luciferase ($0.5\times10^6$ cells) in PBS (100 μL). After 72 hrs, mice were imaged for their basal luminescence levels using an IVIS200 imager. Mice with visible luminescence were randomized into equal groups including vehicle (n=8), RA414 (3 mg/Kg, n=8), RA414 (10 mg/Kg, n=8) and treated every three days for up to 3 weeks. Mice were imaged every week to measure bioluminescence expressed by tumor after administration of luciferin. In the vehicle group, all 8 mice showed enlarged abdomens due to ascites formation. On day 24 two mice were sacrificed after collection of ascites, and the remainder required euthanasia on day 31 (FIGS. 17A and 17B). Administration of RA414 at 10 mg/kg (3 doses delivered every three days) regressed the tumor completely in 50% of the mice with less than 10% weight loss. However, the remaining 50% of the mice did not tolerate the dose (>10% weight loss) or died, indicating this is above the MTD in tumor-bearing mice. Administration of RA414 at 3 mg/Kg (9 doses delivered every three days) was well tolerated by the mice and inhibited tumor growth (FIG. 17A). Furthermore, analysis of ascites cells collected on day 24 from two RA414-treated mice by Western blotting with antibody to ubiquitin demonstrated the accumulation of high molecular polyubiquitinated proteins that was absent from ascites of control mice (FIG. 17B). This is consistent with proteasome inhibition within the ascites cells by the 3 mg/mL RA414 treatment regimen.

Figure 18:
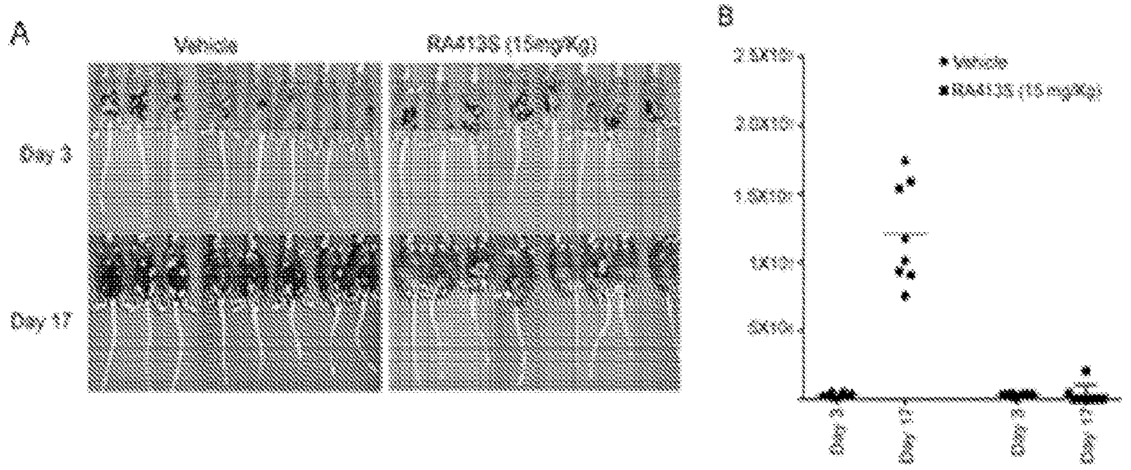
FIG. 18 illustrates tumor growth inhibition of RA413S in a syngeneic mouse model of ovarian cancer.

To examine the in vivo activity of RA413S, female C57BL/6 mice were administered ID8-VegfDefb29 intraperitoneally in a syngeneic mouse model of ovarian cancer expressing luciferase (62) and imaged by IVIS200 on day 3 just before treatment to ensure tumor take and for randomization (FIG. 18A). Treatment was initiated on day 3 and the mice were imaged again after treatment with either vehicle or RA413S (15mg/Kg/every 3 days/total 5 doses) on day 17 using IVIS200 imaging to quantify the bioluminescence expressed by the tumor cells (FIGS. 18A and 181B). This treatment produced a significant decrease in tumor burden compared to vehicle ($p<0.0001$).

Figure 19:
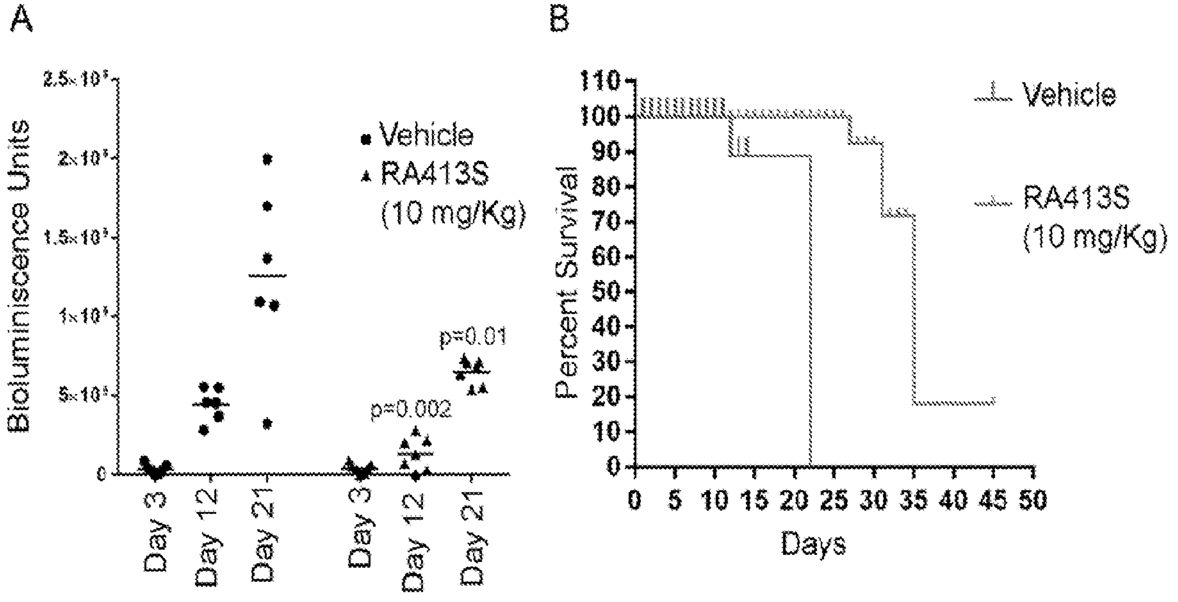
FIG. 19 illustrates tumor growth inhibition effect of RA413S against ovarian cancer xenograft.

The efficacy of RA413S was assessed against a human ovarian cancer xenograft model. Briefly, female nude mice were injected interperitoneally (i.p.) with ES2-luc cells ($1\times10^6$) in 100 μL PBS and the basal luminescence was measured after three days using IVIS 200 imaging after injecting luciferin. Tumor-bearing mice were randomized into two groups to receive either vehicle alone (n=7) or RA413S (n=7, 10 mg/Kg/every 3 days/total 12 doses). Over the treatment period mice were imaged every week for bioluminescence to monitor tumor growth. Mice treated with RA413S tolerated the drug and showed significantly reduced tumor burden (FIG. 19A) and significantly increased survival (FIG. 19B).

Synergistic Activity of iRPN13 with DNA Damaging Agent Cisplatin

Figure 20:
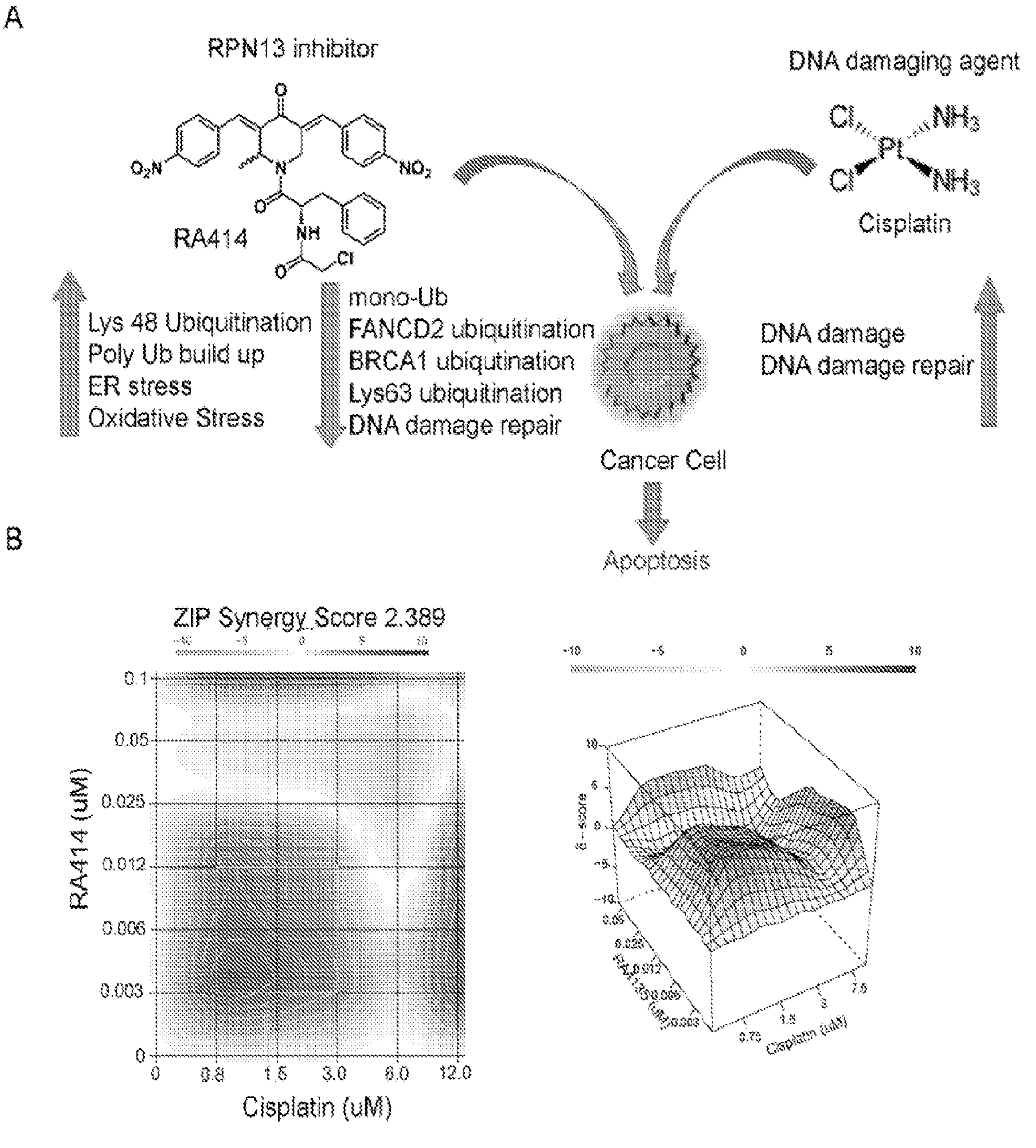
FIG. 20 illustrates the synergy of cisplatin and RA414 in vitro.

Platinum agents, such as cisplatin or carboplatin, are the primary therapeutic option for ovarian cancer patients. They produce DNA damage and activate the DNA damage repair pathway (DDR) in a ubiquitin-dependent manner (71). Thus, decrease in the cellular ubiquitin levels by iRPN13 may cause interruption in DDR pathway and enhance sensitivity to cisplatin (FIG. 20A). In addition to DNA damage, cisplatin treatment induces proteasomal degradation of copper transporter receptor (CTR1) protein which is responsible for cisplatin uptake in cells. This limits the killing effect of ovarian cancer cells to cisplatin but the effect can be reversed by proteasome inhibition (63). Therefore, it was examined whether cisplatin is synergistic with an iRPN13. Combination treatment with RA414 and cisplatin showed evidence of synergy in cytotoxicity of OVCAR3 cells (FIG. 20B) when the combination effect was analyzed using a SynergyFinder web application (Version 1) to determine the optimal concentration of each component. Combination treatment of RA183 and RA375 and evidence of synergy is shown below (Table 6). Synergy scores were obtained via the SynergyFinder (Version 1) web application. Higher scores, especially greater than 5, suggest synergy.

TABLE 6

Synergy scores of RA183 or RA375 in combination with approved chemotherapeutic agents.

| | | Synergy Scores | | | |
|---|---|---|---|---|---|
| Compounds | Cell Line | HSA | Loewe | Bliss | ZiP |
| Cisplatin + RA183 | OVCAR3 | 17.954 | 16.101 | 16.127 | 16.561 |
| Doxorubicin + RA183 | OVCAR3 | 17.775 | 15.183 | 15.206 | 15.6 |
| Vincristine + RA183 | OVCAR3 | 8.732 | 5.618 | 3.841 | 3.975 |
| Doxorubicin + RA375 | ID8 | 14.201 | | 6.083 | 6.08 |
| Doxorubicin + RA375 | SSC90 | 9.141 | 5.326 | 4.423 | 4.481 |
| Doxorubicin + RA375 | OVCAR3 | 10.66 | | 10.46 | 10.51 |

Discussion

Treatment of ovarian cancer cells with candidate iRPN13s RA413S and RA414 caused proteasome inhibition, increased oxidative stress and activated cellular and mitochondrial apoptosis. Alterations in the mitochondrial dependent cellular bioenergetics also resulted in depletion in ATP production and was associated with rapid onset of death of cancer cells. Treatment with RA413S inhibited tumor growth in both syngeneic and xenograft models of ovarian cancer and increased overall survival.

RA413S and RA414 both bind to RPN13 in ovarian cancer cell lysates better than their parent molecule RA183. Likewise they inhibit proteasome function and promote ER stress, oxidative stress, mitochondrial damage, ATP depletion, NF-κB inhibition, and finally activated apoptosis in cancer cells more potently than RA183. Treatment with these compounds regressed tumor growth and increased survival in mouse models of ovarian cancer, although the higher dose of RA414 produced toxicities in tumor-bearing animals suggesting 3 mg/kg is its MTD. An initial analysis of RA414 identified synergistic dose combinations with cisplatin suggesting that this might be a potent combination that could allow for the use of lower RA414 doses. Further studies are warranted to address the involvement of RPN13 in cisplatin resistance and the underlying mechanism of synergy between iRPN13 and cisplatin.

EXAMPLE S

Embodiments of the invention are exemplified by the examples that follow. These examples are intended to demonstrate the invention and not to limit the scope.

Synthesis and Characterization of Compounds

General: $^{1}H$ and $^{13}C$ NMR spectra were recorded as a CDCl3 or $CD_3OD$ or DMSO-d6 solution on a Bruker ADVANCE 400 FT NMR operating at 400 MHz. Chemical shifts are reported in parts per million. J values were measured in Hz. All commercially available materials and solvents were purchased from Sigma Aldrich or Fisher scientific.

Example 1: Synthesis and Characterization of RA375

RA375 was prepared from RA183 as shown in Scheme 1.

Scheme 1

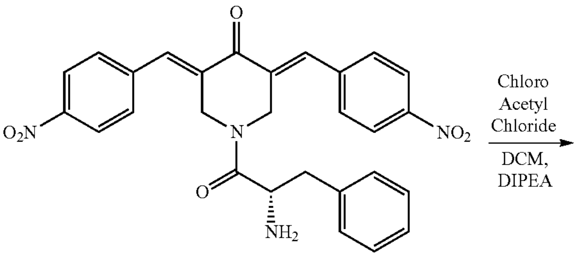

RA411

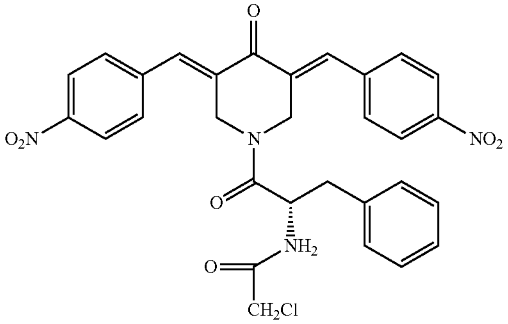

RA375

RA183 (0.63 g) dissolved in DCM was added to 3 eq of DIPEA and 1.1 eq of chloroacetyl chloride at 0° C. The reaction mixture was stirred at room temperature for 3 hr, and saturated sodium bicarbonate solution was added. Excess DCM was added and the layers were separated. The organic layer was washed with H2O and brine and dried over Na2SO4. The solvent was removed in vacuo and the residue was purified by column chromatography on silica gel eluted with ethyl acetate: hexanes to obtain RA375 with >97% purity confirmed by NMR and MS. yield, 0.47 g; 1H NMR (400 MHz, CDCl3): 2.8-2.94 (m, 2 H), 3.98 (s, 2H), 4.18-4.55 (dd, 2H), 4.72-4.99 (m, 3H), 6.98-7.05 (m, 2H), 7.22-7.47 (m, 5H), 7.63-7.67 (m, 2H), 7.71-7.82 (m, 2H), 8.28-8.45 (m, 4H); M+592.

Example 2: Synthesis and Characterization of RA371

RA371 was prepared from RA190 as shown in Scheme 2.

Scheme 2

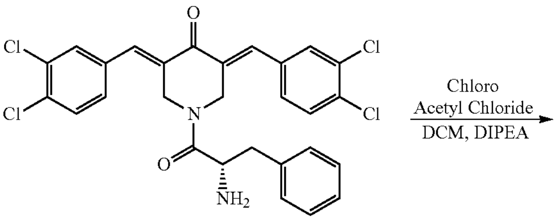

RA190

-continued

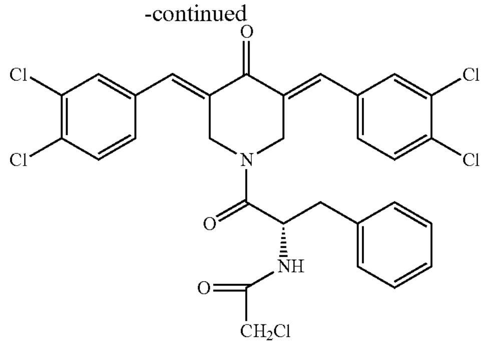

RA371

RA190 (0.54 g) dissolved in DCM was added to 3 eq of DIPEA and 1.1 eq of chloroacetyl chloride at 0° C. The reaction mixture was stirred at room temperature for 3 hr and saturated sodium bicarbonate solution was added. Excess DCM was added and the layers were separated. The organic layer washed with H2O and brine and dried over Na2SO4. The solvent was removed in vacuo and the residue was purified by column chromatography on silica gel eluted with ethyl acetate: hexanes to obtain RA371 with >97% purity confirmed by NMR and MS. yield, 0.37 g; 1H NMR (400 MHz, CDCl3): 2.78-2.97 (m, 2 H), 3.99 (s, 2H), 4.12-4.17 (m, 1H), 4.43-4.78 (dd, 2H), 4.8-4.99 (m, 2H), 6.99-7.20 (m, 3H), 7.23-7.47(m, 6H), 7.52-7.69 (m, 4H).

Example 3: Synthesis and Characterization of RA413S

RA413S was prepared as shown in Scheme 3.

Preparation of compound RA411S: To a stirred solution of compound 1 (1 mmol) in acetic acid (10 mL) was added 4-nitro-benzaldehyde (2 mmol) and then dry HCl gas was passed into the solution for 30 min continuously while stirring. The resulting yellow colored solution was left over night without stirring and the resulting precipitate was filtered and washed with cold ethanol and filtered and dried to afford compound RA411S. $^{1}$H NMR (DMSO-d6) δ 1.61 (s, 3H), 4.7 (dd, 2H, J=8.0 Hz), 4.99-5.08 (m, 1H), 7.88-8.03 (m, 10H); m/z ES+1: 380.

Preparation of compound RA412S: To a stirred solution of Boc-Phe-OH (1 mmol) in DMF (10 mL) was added HBTU (1.1 mmol), HOBT (1.1 mmol) and diisopropylethylamine (3 mmol) at 0° C. To this reaction mixture RA411S (1 mmol) in DMF (1 mL) was added and the reaction was stirred at room temperature overnight. After completion of the reaction, as indicated by TLC, the solvent was removed under reduced pressure and the resulting crude was partitioned between ethyl acetate (2×50 mL) and water. The ethyl acetate layer was washed with brine and dried over sodium sulfate. Removal of ethyl acetate under reduced pressure and column chromatography purification (using Ethyl acetate and hexanes as eluents (40:60)) afforded yellow powder.

Preparation of compound RA413S: A solution of RA412S (1 mmol) in 4M HCl in dioxane (10 mL) was stirred for 30 min at room temperature. After completion of the reaction, as indicated by TLC, dioxane was removed under vacuum and the resulting slurry was added to diethyl ether to precipitate yellow solid. The precipitate was filtered and washed with diethylether and dried to afford RA413S as the HCl salt. $^{1}$H NMR ($CD_3OD$) δ 1.4 (s, 3H), 2.6-3.1 (m, 2H), 4.32-4.81 (m, 3H), 6.01 (s, 1H), 6.81 (s, 1H), 7.01 (s, 1H), 7.1-7.92 (m, 8H), 8.23-8.52 (m, 5H); 13C NMR ($CD_3OD$);

Scheme 3

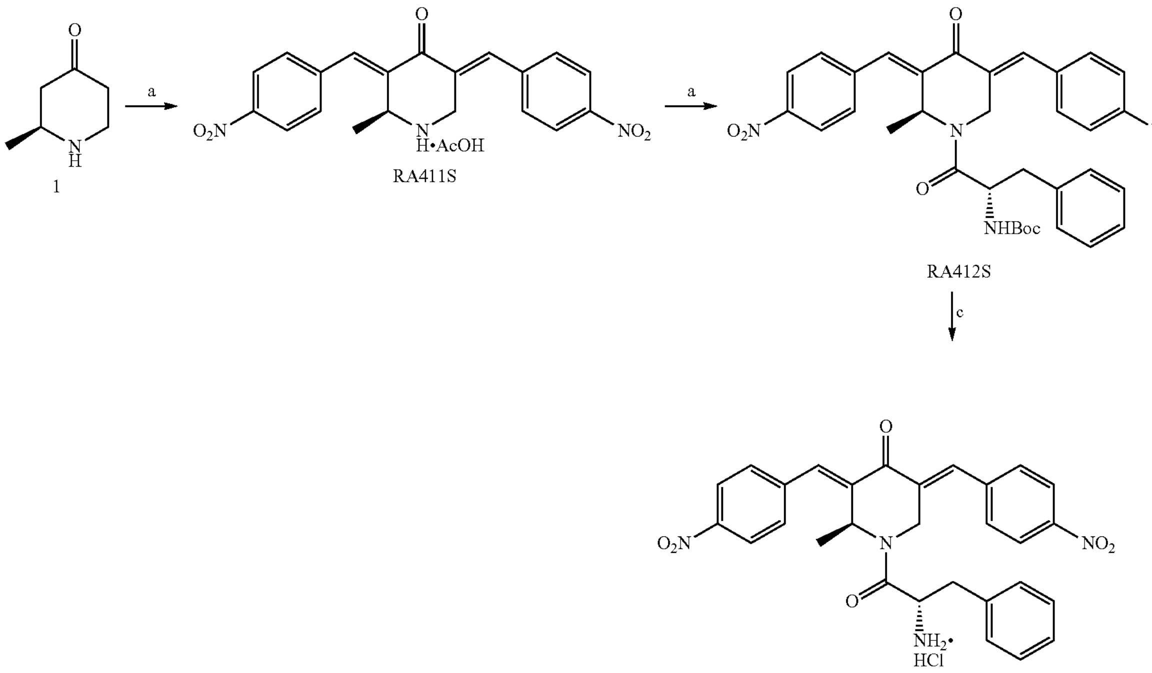

Synthesis of RA413S: (a) 4-$NO_2$—CHO, AcOH, dry HCl gas, overnight (b) DMF, Diisoproyl Ethyl amine, Boc-Phe-OH, HBTU, HOBt, overnight (c) 4M HCl in dioxane, 30 min.

δ 19.2, 39.1, 42.2, 44.6, 52.4, 126.1, 129.8, 143.3, 146.9, 151.2, 170.3, 189.7; m/z ES+1: 527.

Example 4: Synthesis and Characterization of RA414

RA414 was prepared as shown in Scheme 4.

Scheme 4

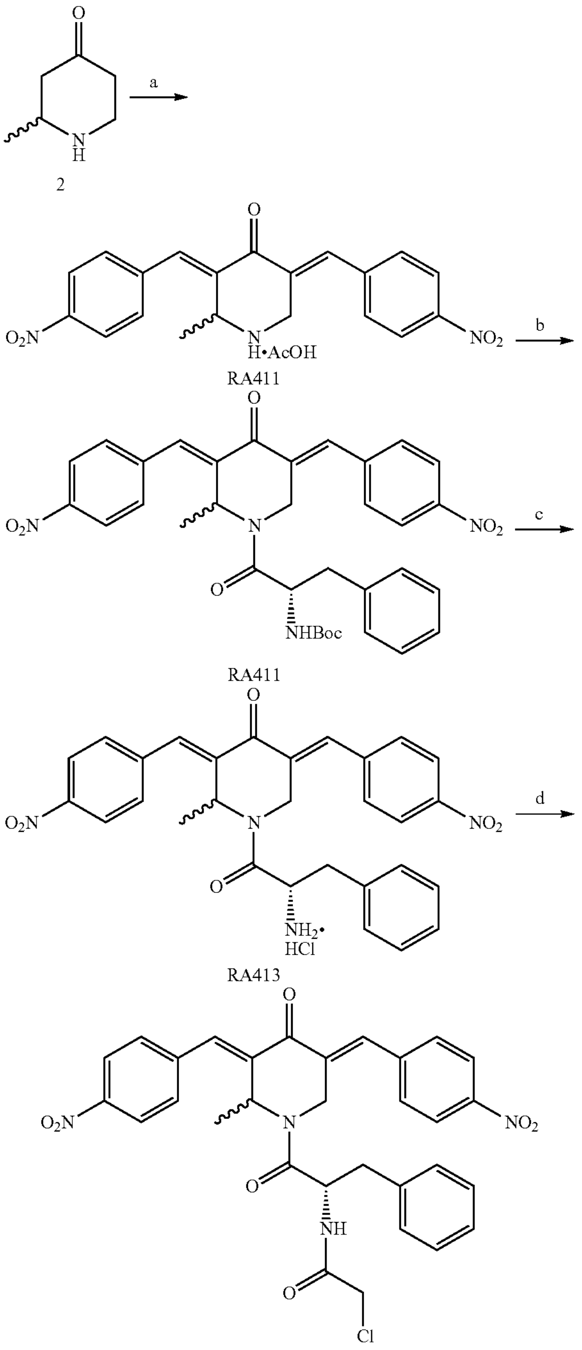

2, RA411, RA411, RA413, RA413

Synthesis of RA414: (a) 4-$NO_2$—CHO, AcOH, dry HCl gas, overnight (b) DMF, Diisopropyl Ethyl amine, Boc-Phe-OH, HBTU, HOBt, overnight (c) 4M HCl in dioxane, 30 min (d) DCM, Diisopropyl ethylamine, chloroacetyl chloride, 0° C. - rt, 30 min.

Preparation of RA414: Racemic RA413 was synthesized using the above mentioned method. To a solution of racemic RA413S (1 mmol) in dichloromethane (DCM) (20 mL) was added diisopropylethyalamine (3 mmol) and chloroacetylchloride (1 mmol) at 0° C. and the reaction mixture stirred for 30 min. After completion of the reaction, indicated by TLC, DCM was partitioned with water, separated, washed with brine and dried over sodium sulfate. DCM was removed under reduced pressure and the crude compound was purified by column chromatography using DCM:Acetone (96:4) as solvents to afford RA414 as a solid. $^1$H NMR ($CDCl_3$) δ 1.6 (s, 3H), 3.1 (dd, 2H, J=8 Hz), 3.92-4.08 (m, 2H), 4.45 (dd, 1H, J=16 Hz), 4.98-5.09 (s, 1H), 7.01-7.9 (m, 10H), 8.3-8.45 (m, 5H).

Materials and Methods

Cell lines and cytotoxicity assays: All cell lines were obtained from the American Type Culture Collection (ATCC) and cultured in the specified medium supplemented with 10% fetal bovine serum, 100 IU/mL penicillin, and 100 μg/mL streptomycin at 37° C. in a humidified 5% $CO_2$/95% air incubator. Synthesis of key compounds is described herein, and >95% purity of RA413S and RA414 were confirmed by NMR and MS. To assess drug cytotoxicity, cells were seeded at 2,500 cells/well (10,000 cells/well for MM lines) in 100 μL medium in 96-well plate and after 24 treated with compounds for 72 h, incubated according to the manufacturer's protocol with the Thiazolyl Blue Tetrazolium Bromide (Sigma, M2128) and $A_{570}$ measured using a Benchmark Plus microplate spectrophotometer (BIO-RAD). IC50 data was analyzed by Graphpad Prism software. In the chirality studies the cells were treated with compounds for 48 h, and the cells were incubated and measured via the preceeding protocols.

Antibodies, reagents, and Western Blot Analyses: Cell lysate (10-20 μg total protein) prepared in MPER (Pierce) from each sample was subjected to SDS-PAGE, transferred to PVDF membranes and analyzed by Western blot using antibodies specific Bax (#2772, Cell Signaling), ubiquitin (P4D1, sc-8017, Santa Cruz), PARP (#9542, BD Pharmingen), actin (#66009, Protein Tech Group), Tubulin(#66031, Protein Tech Group), ADRM1/Rpn13 (D9Z1U, #12019, Cell Signaling), Lys48-linkled ubiquitin (Apu 2, 05-1307, (Millipore), Annexin V (#559763, BD pharmingen), caspase-3 (51-68655X, BD Pharmingen) at the dilutions recommended by the manufacturers, and for secondary antibodies either peroxidase-linked anti-mouse IgG or anti-rabbit IgG (GE Healthcare UK Ltd) were utilized, HRP conjugated streptavidin (N100, Thermo Fisher) at the recommended dilution (1:5000). MitoTracker Red CMXRos reagent was purchased from ThermoFisher #M7512. The blots were developed using HyGLO chemiluminescent detection reagent (Denville).

Reporter assays: Sub-confluent cultures of cells were transfected with 4Ub-FL or FL plasmid using TransIT 2020 reagent (Minis Bio). Cells were seeded at 10,000 cells/well in 96-wells plate 48 h post transfection and incubated with compounds or vehicle (DMSO) at the doses and times indicated. Luciferase activity in cell lysate was determined with a luciferase assay kit (Promega) according to the manufacturer's instructions. Bioluminescence was measured by using a Glomax Multidetection system (Promega).

ATP measurement assay: To measure ATP levels in cells, luciferase based bioluminescence assay was performed. Briefly cells stably expressing firefly luciferase plated in a 6 well plate (250,000 cells/well) in growth medium. After 24 h incubation, cells were treated with compounds at indicated concentrations for the period of 4 h and the bioluminescence was measured by IVIS 200 imager in intact cells by adding luciferin substrate to the growth medium. Cell viability was assessed in parallel using an MTT assay.

Flow cytometry analysis of cell death and ROS: To measure Annexin V positive cells, $10^5$ cells were re-suspended in binding buffer, 5 μL of Annexin V-PE (Apoptosis Detection Kit I (BD Pharmingen) and 5 μL of 7-AAD were then added into the cells, which were then incubated at room temperature for 15 minutes and analyzed by flow cytometry on a FACSCalibur using CellQuest software (Becton Dickinson). For assay of ROS, $2\times10^5$ cells were plated in a 6-well plate the day before treatment with compounds or vehicle. After treatment, plates were washed once with PBS, and the cells were harvested using trypsin-EDTA. Cells were washed again with PBS and then suspended in 1 mL of PBS and incubated with 1 μM 2,7-dichlorofluorescein diacetate ($H_2$DCFDA) at 37° C. for 60 min. Cells were then washed twice with PBS and analyzed by flow cytometry.

Amplex Red Assay to measure ROS: Amplex Red reagent (#A12222, Thermo Scientific) combined with horseradish peroxidase (HRP) was used to detect $H_2O_2$. Briefly cells were treated in 96 well plates with corresponding compounds at indicated times. Next 50 μM Amplex® Red reagent plus 1 U/mL HRP in 50 mM sodium phosphate buffer, pH 7.4, were added to cells and incubated for 30 minutes at room temperature. Fluorescence was measured with a fluorescence-based microplate reader using excitation at 530±12.5 nm and detection at 580±25 nm. Background fluorescence of 969 units for Amplex® Red reagent, determined for a no-$H_2O_2$ control reaction, was subtracted from each value. $H_2O_2$ treatment (1 h) was used as positive control.

Biotin labeling Assay: Clarified cell lysate in MPER buffer was pretreated with streptavidin magna beads for 45 min at 4° C. to deplete non-specific biotinylated proteins in the cell lysate. The beads were separated and 40 μL of the pre-cleared cell lysate was incubated with compounds (20 μM) for 45 min at 4° C., and then treated with RA183B, RA190B, or RA413SB (10 μM) for 45 min at 4° C. Next, the samples were mixed with Laemmli sample buffer (BioRad) and boiled for 5 min. The proteins were separated using a 4-15% Bio-Rad Mini-PROTEAN SDS-PAGE gel (1 hr at 100 V), and transferred to PVDF membrane overnight at 4° C. (24 V). The membrane was blocked with 5% BSA in PBST for 1 hr at RT and washed for 20 minutes (3× with PBST). Then the membrane was probed with HRP-streptavidin (1:10,000 in PBST) for 1 hr at RT, washed for 30 min (3× with PBST), and developed using HyGLO chemiluminescent detection reagent (Denville) for biotin detection.

Luciferase and GSH assays: Sub-confluent cultures of cells were transfected with 4Ub-FL or FL plasmid using Lipofectamine 2000 reagent (Life Technologies). Cells were seeded at 10,000 cells/well in 96-wells plate 48 hr post transfection and incubated with compounds or vehicle (DMSO) at the doses and times indicated. Luciferase activity in cell lysate was determined with a luciferase assay kit (Promega) according to the manufacturer's instructions. Bioluminescence was measured by using a Glomax Multi-detection system (Promega). Glutathione was assayed using the Promega GSH assay kit (V6611).

Q-PCR to measure mRNA levels: Total RNA was isolated from cells using the RNeasy mini kit (Qiagen) according to the manufacturer's instructions. Extracted RNA was normalized for concentration and reverse transcribed using an iScript cDNA synthesis kit (Bio-Rad) according to the manufacturer's instructions. CHOP10 expression levels were measured by Taqman gene expression assays with Taqman gene expression master mix (Applied Biosystems) and run with a standard thermal cycling protocol. Spliced XBP1 mRNA was assayed with SsoFast EvaGreen Supermix (Bio-rad) following the protocol for the iCycler System using as primers: F: 5'-TGCTGAGTCCGCAGCAGGTG-3' and R: 5'-TGGGTCCAAGTTGTCCAGAATGCC-3'. Calculations were done according to the Livak method and normalized to the reference gene GAPDH. Each condition was replicated three times; each sample was run in triplicate.

MitoTracker Assay: HeLa cells were seeded at $1\times10^5$ cells/well into 12-well plates containing glass coverslips and grown overnight to reach 50-70% confluence. Cells were treated with RA413 (100 nM and 500 nM; 6, 8, and 12 hours), CCCP (1 μM, 30 minutes), bortezomib (500 nM, 6, 8, and 12 hours) suspended in DMSO, or DMSO as a vehicle control (6, 8, and 12 hours). Following time course, media was replaced with fresh media containing 100 nM MitoTracker Red CMXRos (resuspended in DMSO) and incubated for 45 minutes. Cells were fixed with −20° C. 100% methanol for 15 minutes then washed three times with 1× PBS. DNA was stained with Hoechst (1:5000) in PBS for 10 minutes and washed three times with 1× PBS. Coverslips were mounted on glass microscope slides using ProLong Glass Antifade Mountant. Coverslips were imaged using a Nikon epifluorescent microscope using a Nikon 60× Plan Apo Oil objective. Imaging of each condition was conducted in at least three individual experiments.

Mitochondrial Functionality Analysis: mtDNA quantification: Cells were grown in 100 mm dishes overnight to 90% confluence. Cells were treated with RA413 (100 nM, 250 nM, or 500 nM), bortezomib (500 nM), or DMSO vehicle for 18 hours. Following treatment, cells were trypsinized and centrifuged into microfuge tubes. Total DNA was extracted using the DNeasy Blood and Tissue Kit (Qiagen) by the manufacturer's protocol. Samples were collected in triplicate. DNA purity and concentration was measured with Nanodrop.

Seahorse Assay: For quantification of oxygen consumption rate, ES2 cells were seeded at 20,000 cells per well in Seahorse XF96 Analyzer plates in regular media and incubated at 37° C. with 5% $CO_2$ overnight. Cells were treated compounds for 8 hr and the media was then removed, cells were washed, Seahorse media (RPMI+17.5 mm glucose+1 mM pyruvate+2 mM glutamine) was added to wells, and the plate was incubated at 37° C. without $CO_2$ for 1 hour. The plate was then loaded into the Seahorse machine and readings of oxygen and pH levels were taken before and after injections of 3 μM oligomycin, 4 μM FCCP, 2 μM antimycin, and 2 μM rotenone. Oxygen consumption rate and extracellular acidification rate were analyzed using Wave 2.4 software.

Schrodinger Methods: Glide Ligand Docking: The ligands RA413S, RA183 and RA414 were docked into RPN13 Pm Domain protein (PDB ID: SIRS) by utilizing Glide module of Schrödinger suite Maestro V12.3. The docking was performed utilizing Standard precision (XP) mode and OPLS-3e power field and the above docking process was run in a flexible docking mode which automatically generates conformations for each input ligand. The best-docked ligands are chosen based on MM-GBSA score using Prime-MM-GBSA module of Schrodinger Maestro Suite 2020-2.

Animal studies: All animal procedures were performed according to protocols approved by the Johns Hopkins University Animal Care and Use Committee, and in accordance with the AAALAC recommendations for the proper use and care of laboratory animals (protocol MO15M375, renewed as MO18M129). Four to six week old female Nude (002019), or Balb/c (000651) mice, or CD1 mice or C57BL6 mice were purchased from Jackson Laboratories (ME, USA). Isoflurane anesthesia was used during imaging. The health conditions and/or criteria under which early euthanasia or withdrawal of an animal from the study was implemented included, but are not limited to, general signs of distress such as hunched posture, lethargy, anorexia, dehydration, rough hair coat and/or those that are directly related to the experimental procedures e.g. loss of weight >10%, lethargy, restricted movement of limbs, distended abdomen. Animals in distress were euthanized by carbon dioxide asphyxiation, and cervical dislocation was used to ensure death. This is an acceptable form of euthanasia for mice and in compliance with the recommendations of the Panel on Euthanasia of the American Veterinary Medical Association.

Electroporation Method: A patch of CD1 or Balb/c mouse leg was shaved of hair and 10 μg 4Ub-FL plasmid in 20 μL of PBS was injected into the quadriceps femoralis muscle followed immediately by injection of the 2 Needle Array to 5 mm depth encompassing the injection site and square wave electroporation (ElectroSquarePorator 833, BTX-2 Needle array 5 mm gap, Harvard apparatus) delivered as eight pulses at 106V for 20 ms with 200 ms intervals. One day post electroporation, mice were anesthetized with isoflurane, injected i.p. with luciferin (0.3 mg in 100 μL water) and optical imaging was performed to determine basal level luciferase expression. Images were acquired for 10 min with a Xenogen IVIS 200 (Caliper, Hopkinton, MA). Equally sized areas were analyzed using Living Image 2.20 software. Mice were imaged weekly during treatment.

Tumor Studies: Female C57BL6 or Nude mice were inoculated with $10^6$ ES2-Luciferase cells i.p. in 100 uL PBC, or ID8-VegfDefb29 syngeneic mouse model of ovarian cancer expressing luciferase (62) i.p. in 100 μL PBS. At day 3, mice were imaged for basal level luminescence activity with a Xenogen IVIS 200 after injection i.p. with luciferin (0.3 mg in 100 water). Mice were randomized into two groups (n=8) and treated i.p. with compounds or vehicle (25% (w/v) β-Hydroxypropylcyclodextrin in water), and imaged again on days 7 and 14. RA375 was administered i.p. at 10 mg/Kg.

Statistical analyses: Results are reported as mean ±standard deviation (s.d.). Statistical significance of differences was assessed by ordinary 1-way ANOVA using Tukey's multiple comparison test in Prism (V.8.2.0 Graphpad, San Diego, CA) to correct for the false discovery rate with the level of significance set at p≤0.05, or by two-tailed Student's t using Prism (V.5 Graphpad, San Diego, CA) with the level of significance set at p≤0.05. Survival was summarized using Kaplan-Meier methods and compared using log-rank tests. Combination indices (CI) were calculated using Synergy finder (30).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Hochstrasser M. Ubiquitin and intracellular protein degradation. Curr Opin Cell Biol. 1992; 4(6): 1024-31.
2. Dou QP, Zonder J A. Overview of proteasome inhibitor-based anti-cancer therapies: perspective on bortezomib and second generation proteasome inhibitors versus future generation inhibitors of ubiquitin-proteasome system. Curr Cancer Drug Targets. 2014;14(6):517-36.
3. Broyl A, Corthals S L, Jongen J L, van der Holt B, Kuiper R, de Knegt Y, et al. Mechanisms of peripheral neuropathy associated with bortezomib and vincristine in patients with newly diagnosed multiple myeloma: a prospective analysis of data from the HOVON-65/GMMG-HD4 trial. Lancet Oncol. 2010;11(11):1057-65.
4. VanderLinden R T, Hemmis C W, Yao T, Robinson H, Hill C P. Structure and energetics of pairwise interactions between proteasome subunits RPN2, RPN13, and ubiquitin clarify a substrate recruitment mechanism. J Biol Chem. 2017;292(23):9493-504.
5. Liu Z, Dong X, Yi H W, Yang J, Gong Z, Wang Y, et al. Structural basis for the recognition of K48-linked Ub chain by proteasomal receptor Rpn13. Cell Discov. 2019; 5:19.
6. Lu X, Nowicka U, Sridharan V, Liu F, Randles L, Hymel D, et al. Structure of the Rpn13-Rpn2 complex provides insights for Rpn13 and Uch37 as anticancer targets. Nat Commun. 2017;8:15540.
7. Lu X, Liu F, Durham S E, Tarasov S G, Walters K J. A High Affinity hRpn2-Derived Peptide That Displaces Human Rpn13 from Proteasome in 293T Cells. PLoS One. 2015;10(10):e0140518.
8. Chen X, Walters K J. Structural plasticity allows UCH37 to be primed by RPN13 or locked down by INO80G. Mol Cell. 2015;57(5):767-8.
9. Jiao L, Ouyang S, Shaw N, Song G, Feng Y, Niu F, et al. Mechanism of the Rpn13-induced activation of Uch37. Protein Cell. 2014;5(8):616-30.
10. Anchoori R K, Karanam B, Peng S, Wang J W, Jiang R, Tanno T, et al. A bis-benzylidine piperidone targeting proteasome ubiquitin receptor RPN13/ADRM1 as a therapy for cancer. Cancer Cell. 2013; 24(6): 791-805.
11. Song Y, Park P M C, Wu L, Ray A, Picaud S, Li D, et al. Development and preclinical validation of a novel covalent ubiquitin receptor Rpn13 degrader in multiple myeloma. Leukemia. 2019.
12. Song Y, Ray A, Li S, Das D S, Tai Y T, Carrasco R D, et al. Targeting proteasome ubiquitin receptor Rpn13 in multiple myeloma. Leukemia. 2016;30(9):1877-86.
13. Anchoori R K, Jiang R, Peng S, Soong R S, Algethami A, Rudek M A, et al. Covalent Rpn13-Binding Inhibitors for the Treatment of Ovarian Cancer. ACS Omega. 2018; 3(9):11917-29.
14. Kisselev A F. A novel bullet hits the proteasome. Cancer Cell. 2013;24(6):691-3.
15. Randles L, Anchoori R K, Roden R B, Walters K J. The Proteasome Ubiquitin Receptor hRpn13 and Its Interacting Deubiquitinating Enzyme Uch37 Are Required for Proper Cell Cycle Progression. J Biol Chem. 2016;291 (16):8773-83.
16. Soong R S, Anchoori R K, Yang B, Yang A, Tseng S H, He L, et al. RPN13/ADRM1 inhibitor reverses immunosuppression by myeloid-derived suppressor cells. Oncotarget. 2016;7(42):68489-502.

17. Jiang R T, Yemelyanova A, Xing D, Anchoori R K, Hamazaki J, Murata S, et al. Early and consistent overexpression of ADRM1 in ovarian high-grade serous carcinoma. J Ovarian Res. 2017; 10(1):53.
18. Yu G Y, Wang X, Zheng S S, Gao X M, Jia Q A, Zhu W W, et al. RA190, a Proteasome Subunit ADRM1 Inhibitor, Suppresses Intrahepatic Cholangiocarcinoma by Inducing NF-KB-Mediated Cell Apoptosis. Cell Physiol Biochem. 2018; 47(3):1152-66.
19. Rao G, Nkepang G, Xu J, Yari H, Houson H, Teng C, et al. Ubiquitin Receptor RPN13 Mediates the Inhibitory Interaction of Diphenyldihaloketones CLEFMA and EF24 With the 26S Proteasome. Front Chem. 2018;6:392.
20. Fejzo M S, Dering J, Ginther C, Anderson L, Ramos L, Walsh C, et al. Comprehensive analysis of 20q13 genes in ovarian cancer identifies ADRM1 as amplification target. Genes Chromosomes Cancer. 2008; 47(10):873-83.
21. Fejzo M S, Anderson L, von Euw EM, Kalous O, Avliyakulov N K, Haykinson M J, et al. Amplification Target ADRM1: Role as an Oncogene and Therapeutic Target for Ovarian Cancer. Int J Mol Sci. 2013;14(2): 3094-109.
22. Lee A H, Iwakoshi N N, Anderson K C, Glimcher L H. Proteasome inhibitors disrupt the unfolded protein response in myeloma cells. Proc Natl Acad Sci USA. 2003;100(17):9946-51.
23. Smith M H, Ploegh H L, Weissman J S. Road to ruin: targeting proteins for degradation in the endoplasmic reticulum. Science. 2011; 334(6059):1086-90.
24. Nawrocki S T, Carew J S, Pino M S, Highshaw R A, Dunner K, Jr., Huang P, et al. Bortezomib sensitizes pancreatic cancer cells to endoplasmic reticulum stress-mediated apoptosis. Cancer Res. 2005; 65(24):11658-66.
25. Walter P, Ron D. The unfolded protein response: from stress pathway to homeostatic regulation. Science. 2011; 334(6059): 1081-6.
26. Maharjan S, Oku M, Tsuda M, Hoseki J, Sakai Y. Mitochondrial impairment triggers cytosolic oxidative stress and cell death following proteasome inhibition. Sci Rep. 2014;4:5896.
27. Starheim K K, Holien T, Misund K, Johansson I, Baranowska K A, Sponaas A M, et al. Intracellular glutathione determines bortezomib cytotoxicity in multiple myeloma cells. Blood Cancer J. 2016;6(7):e446.
28. Tsuboi K, Bachovchin D A, Speers A E, Spicer T P, Fernandez-Vega V, Hodder P, et al. Potent and selective inhibitors of glutathione S-transferase omega 1 that impair cancer drug resistance. J Am Chem Soc. 2011;133 (41):16605-16.
29. Ramkumar K, Samanta S, Kyani A, Yang S, Tamura S, Ziemke E, et al. Mechanistic evaluation and transcriptional signature of a glutathione S-transferase omega 1 inhibitor. Nat Commun. 2016;7:13084.
30. Ianevski A, He L, Aittokallio T, Tang J. SynergyFinder: a web application for analyzing drug combination dose-response matrix data. Bioinformatics. 2017;33(15):2413-5.
31. D'Arcy P, Brnjic S, Olofsson M H, Fryknas M, Lindsten K, De Cesare M, et al. Inhibition of proteasome deubiquitinating activity as a new cancer therapy. Nat Med. 2011;17(12):1636-40.
32. Wang X, Mazurkiewicz M, Hillert E K, Olofsson M H, Pierrou S, Hillertz P, et al. The proteasome deubiquitinase inhibitor VLX1570 shows selectivity for ubiquitin-specific protease-14 and induces apoptosis of multiple myeloma cells. Sci Rep. 2016; 6:26979.
33. Ri M, Iida S, Nakashima T, Miyazaki H, Mori F, Ito A, et al. Bortezomib-resistant myeloma cell lines: a role for mutated PSMB5 in preventing the accumulation of unfolded proteins and fatal ER stress. Leukemia. 2010; 24(8):1506-12.
34. Robak P, Drozdz I, Szemraj J, Robak T. Drug resistance in multiple myeloma. Cancer Treat Rev. 2018; 70:199-208.
35. Walerych D, Lisek K, Sommaggio R, Piazza S, Ciani Y, Dalla E, et al. Proteasome machinery is instrumental in a common gain-of-function program of the p53 missense mutants in cancer. Nat Cell Biol. 2016; 18(8): 897-909.
36. Ogiwara H, Takahashi K, Sasaki M, Kuroda T, Yoshida H, Watanabe R, et al. Targeting the Vulnerability of Glutathione Metabolism in ARID1A-Deficient Cancers. Cancer Cell. 2019; 35(2):177-90 e8.
37. Anglesio M S, Wiegand K C, Melnyk N, Chow C, Salamanca C, Prentice L M, et al. Type-specific cell line models for type-specific ovarian cancer research. PLoS One. 2013; 8(9):e72162.
38. Strauss S J, Higginbottom K, Juliger S, Maharaj L, Allen P, Schenkein D, et al. The proteasome inhibitor bortezomib acts independently of p53 and induces cell death via apoptosis and mitotic catastrophe in B-cell lymphoma cell lines. Cancer Res. 2007;67(6):2783-90.
39. Qin J Z, Ziffra J, Stennett L, Bodner B, Bonish B K, Chaturvedi V, et al. Proteasome inhibitors trigger NOXA-mediated apoptosis in melanoma and myeloma cells. Cancer Res. 2005; 65(14):6282-93.
40. Liu Y, Ye Y. Proteostasis regulation at the endoplasmic reticulum: a new perturbation site for targeted cancer therapy. Cell Res. 2011;21(6):867-83.
41. Luker G D, Pica C M, Song J, Luker K E, Piwnica-Worms D. Imaging 26S proteasome activity and inhibition in living mice. Nat Med. 2003;9(7):969-73.
42. Lau D H, Lewis A D, Ehsan M N, Sikic B I. Multifactorial mechanisms associated with broad cross-resistance of ovarian carcinoma cells selected by cyanomorpholino doxorubicin. Cancer Res. 1991;51(19):5181-7.
43. Bazzaro M, Anchoori R K, Mudiam M K, Issaenko O, Kumar S, Karanam B, et al. alpha,beta-Unsaturated carbonyl system of chalcone-based derivatives is responsible for broad inhibition of proteasomal activity and preferential killing of human papilloma virus (HPV) positive cervical cancer cells. J Med Chem. 2011;54(2):449-56.
44. Anchoori R K, Khan S R, Sueblinvong T, Felthauser A, Iizuka Y, Gavioli R, et al. Stressing the ubiquitin-proteasome system without 20S proteolytic inhibition selectively kills cervical cancer cells. PLoS One. 2011; 6(8): e23888.
45. Coughlin K, Anchoori R, Iizuka Y, Meints J, MacNeill L, Vogel R I, et al. Small-molecule RA-9 inhibits proteasome-associated DUBs and ovarian cancer in vitro and in vivo via exacerbating unfolded protein responses. Clin Cancer Res. 2014;20(12):3174-86.
46. DeBerardinis R J, Chandel N S. Fundamentals of cancer metabolism. Sci Adv. 2016;2(5):e1600200.
47. Chen L, Brewer M D, Guo L, Wang R, Jiang P, Yang X Enhanced Degradation of Misfolded Proteins Promotes Tumorigenesis. Cell Rep. 2017;18(13):3143-54.
48. Bazzaro M, Lee M K, Zoso A, Stirling W L, Santillan A, Shih Ie M, et al. Ubiquitin-proteasome system stress sensitizes ovarian cancer to proteasome inhibitor-induced apoptosis. Cancer Res. 2006; 66(7):3754-63.

49. Aghajanian C, Dizon D S, Sabbatini P, Raizer J J, Dupont J, Spriggs D R. Phase I trial of bortezomib and carboplatin in recurrent ovarian or primary peritoneal cancer. J Clin Oncol. 2005;23(25):5943-9.

50. Ramirez P T, Landen C N, Jr., Coleman R L, Milam M R, Levenback C, Johnston T A, et al. Phase I trial of the proteasome inhibitor bortezomib in combination with carboplatin in patients with platinum- and taxane-resistant ovarian cancer. Gynecol Oncol. 2008;108(1):68-71.

51. Cresta S, Sessa C, Catapano C V, Gallerani E, Passalacqua D, Rinaldi A, et al. Phase I study of bortezomib with weekly paclitaxel in patients with advanced solid tumours. Eur J Cancer. 2008; 44(13):1829-34.

52. Aghajanian C, Blessing J A, Darcy K M, Reid G, DeGeest K, Rubin S C, et al. A phase II evaluation of bortezomib in the treatment of recurrent platinum-sensitive ovarian or primary peritoneal cancer: a Gynecologic Oncology Group study. Gynecol Oncol. 2009; 115(2): 215-20.

53. Parma G, Mancari R, Del Conte G, Scambia G, Gadducci A, Hess D, et al. An open-label phase 2 study of twice-weekly bortezomib and intermittent pegylated liposomal doxorubicin in patients with ovarian cancer failing platinum-containing regimens. Int J Gynecol Cancer. 2012;22(5):792-800.

54. Kobrinsky B, Joseph S O, Muggia F, Liebes L, Beric A, Malankar A, et al. A phase I and pharmacokinetic study of oxaliplatin and bortezomib: activity, but dose-limiting neurotoxicity. Cancer Chemother Pharmacol. 2013;72(5): 1073-8.

55. Jandial D A, Brady W E, Howell S B, Lankes H A, Schilder R J, Beumer J H, et al. A phase I pharmacokinetic study of intraperitoneal bortezomib and carboplatin in patients with persistent or recurrent ovarian cancer: An NRG Oncology/Gynecologic Oncology Group study. Gynecol Oncol. 2017;145(2):236-42.

56. Grice G L, Nathan J A. The recognition of ubiquitinated proteins by the proteasome. Cell Mol Life Sci. 2016;73 (18):3497-506.

57. Hamazaki J, Hirayama S, Murata S. Redundant Roles of Rpn10 and Rpn13 in Recognition of Ubiquitinated Proteins and Cellular Homeostasis. PLoS Genet. 2015;11(7): e1005401.

58. Berko D, Herkon O, Braunstein I, Isakov E, David Y, Ziv T, et al. Inherent asymmetry in the 26S proteasome is defined by the ubiquitin receptor RPN13. J Biol Chem. 2014;289(9):5609-18.

59. Hemmis C W, Heard S C, Hill C P. Phosphorylation of Tyr-950 in the proteasome scaffolding protein RPN2 modulates its interaction with the ubiquitin receptor RPN13. J Biol Chem. 2019;294(25):9659-65.

60. Aguileta, M. A., Korac, J., Durcan, T. M., Trempe, J. F., Haber, M., Gehring, K., Elsasser, S., Waidmann, O., Fon, E.A., and Husnjak, K. (2015). The E3 ubiquitin ligase parkin is recruited to the 26 S proteasome via the proteasomal ubiquitin receptor Rpn13. J Biol Chem 290, 7492-7505.

61. Al-Shami, A., Jhaver, K. G., Vogel, P., Wilkins, C., Humphries, J., Davis, J. J., Xu, N., Potter, D. G., Gerhardt, B., Mullinax, R., et al. (2010). Regulators of the proteasome pathway, Uch37 and Rpn13, play distinct roles in mouse development. PLoS One 5, e13654.

62. Conejo-Garcia, J. R., Benencia, F., Courreges, M. C., Kang, E., Mohamed-Hadley, A., Buckanovich, R. J., Holtz, D. O., Jenkins, A., Na, H., Zhang, L., et al. (2004). Tumor-infiltrating dendritic cell precursors recruited by a beta-defensin contribute to vasculogenesis under the influence of Vegf-A. Nat Med 10, 950-958.

63. Jandial, D. D., Farshchi-Heydari, S., Larson, C. A., Elliott, G. I., Wrasidlo, W. J., and Howell, S. B. (2009) Enhanced delivery of cisplatin to intraperitoneal ovarian carcinomas mediated by the effects of bortezomib on the human copper transporter 1. Clin Cancer Res 15, 553-560.

64. Jannuzzi, A. T., Arslan, S., Yilmaz, A. M., Sari, G., Beklen, H., Mendez, L., Fedorova, M., Arga, K. Y., Karademir Yilmaz, B., and Alpertunga, B. (2020). Higher proteotoxic stress rather than mitochondrial damage is involved in higher neurotoxicity of bortezomib compared to carfilzomib. Redox Biol 32, 101502.

65. Ling, Y. H., Liebes, L., Zou, Y., and Perez-Soler, R. (2003). Reactive oxygen species generation and mitochondrial dysfunction in the apoptotic response to Bortezomib, a novel proteasome inhibitor, in human H460 non-small cell lung cancer cells. J Biol Chem 278, 33714-33723.

66. Ludman, T., and Melemedjian, O. K. (2019). Bortezomib-induced aerobic glycolysis contributes to chemotherapy-induced painful peripheral neuropathy. Mol Pain 15, 1744806919837429.

67. Mofers, A., Perego, P., Selvaraju, K., Gatti, L., Gullbo, J., Linder, S., and D'Arcy, P. (2019). Analysis of determinants for in vitro resistance to the small molecule deubiquitinase inhibitor b-AP15. PLoS One 14, e0223807.

68. Perez-Galan, P., Roue, G., Villamor, N., Montserrat, E., Campo, E., and Colomer, D. (2006). The proteasome inhibitor bortezomib induces apoptosis in mantle-cell lymphoma through generation of ROS and Noxa activation independent of p53 status. Blood 107, 257-264.

69. Roby, K. F., Taylor, C. C., Sweetwood, J. P., Cheng, Y., Pace, J. L., Tawfik, O., Persons, D. L., Smith, P. G., and Terranova, P. F. (2000). Development of a syngeneic mouse model for events related to ovarian cancer. Carcinogenesis 21, 585-591.

70. Rowinsky, E. K., Paner, A., Berdeja, J. G., Paba-Prada, C., Venugopal, P., Porkka, K., Gullbo, J., Linder, S., Loskog, A., Richardson, P. G., et al. (2020). Phase 1 study of the protein deubiquitinase inhibitor VLX1570 in patients with relapsed and/or refractory multiple myeloma. Invest New Drugs.

71. Schwertman, P., Bekker-Jensen, S., and Mailand, N. (2016). Regulation of DNA double-strand break repair by ubiquitin and ubiquitin-like modifiers. Nat Rev Mol Cell Biol 17, 379-394.

72. Wang, X., D'Arcy, P., Caulfield, T. R., Paulus, A., Chitta, K., Mohanty, C., Gullbo, J., Chanan-Khan, A., and Linder, S. (2015). Synthesis and evaluation of derivatives of the proteasome deubiquitinase inhibitor b-AP15. Chem Biol Drug Des 86, 1036-1048.

73. Wilson, S. M., Bhattacharyya, B., Rachel, R. A., Coppola, V., Tessarollo, L., Householder, D. B., Fletcher, C. F., Miller, R. J., Copeland, N. G., and Jenkins, N. A. (2002). Synaptic defects in ataxia mice result from a mutation in Usp14, encoding a ubiquitin-specific protease. Nat Genet 32, 420-425.

74. Xing, D., and Orsulic, S. (2006). A mouse model for the molecular characterization of brca1-associated ovarian carcinoma. Cancer Res 66, 8949-8953.

75. Zheng, H., Xiao, W. H., and Bennett, G. J. (2012). Mitotoxicity and bortezomib-induced chronic painful peripheral neuropathy. Exp Neurol 238, 225-234.

What is claimed is:

1. A compound of formula (I):

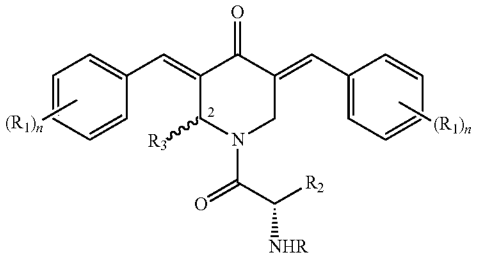

(I)

wherein

R is H, $C(O)CH_2Cl$, $C(O)CH_3$, $C(O)CH{=}CH_2$, or $C(O)N(H)\ CH_3$;

$R_1$ at each occurrence is independently selected from $NO_2$, halogen, and

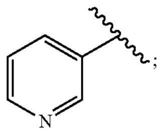 [SMILES: *c1cccnc1]

;

$R_2$ is a side group from an alpha amino acid;

$R_3$ is $C_1$-$C_6$ alkyl, or phenyl, wherein $C_1$-$C_6$ alkyl is a saturated, linear or branched carbon chain having up to 6 carbons;

and n at each occurrence is independently an integer from 0-5, inclusive;

or a pharmaceutically acceptable salt, hydrate, or solvate thereof;

wherein when $R_2$ is the benzyl side group from phenylalanine and $R_3$ is hydrogen, R is C $(O)CH_2Cl$; and wherein the compound of formula (I) is not

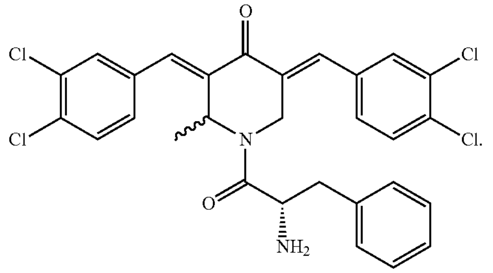 [SMILES: CC1/C(=C\c2ccc(Cl)c(Cl)c2)C(=O)/C(=C/c2ccc(Cl)c(Cl)c2)CN1C(=O)[C@@H](N)Cc1ccccc1]

2. The compound of claim 1 wherein $R_3$ is methyl.

3. The compound of claim 1, wherein $R_2$ is the $(CH_2)_4NH_2$ side group from lysine or the benzyl side group from phenylalanine.

4. The compound of claim 1, wherein $R_2$ is the benzyl side group from phenylalanine; and R is $C(O)CH_2Cl$.

5. The compound of claim 4, wherein each $(R_1)_n$ is 3,4-dichloro, 4-nitro, 2-fluoro or 4-fluoro.

6. The compound of claim 5, selected from the group consisting of

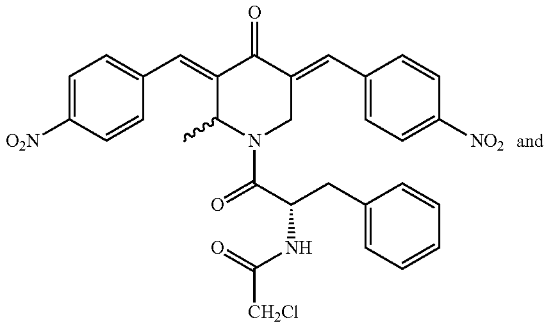

and

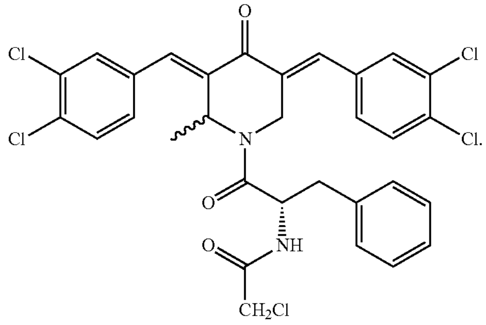

7. The compound of claim 1, wherein $R_2$ is the benzyl side group from phenylalanine; R is H or $C(O)CH_2Cl$;

R is nitro or fluorine; and $R_3$ is methyl.

8. The compound of claim 7, selected from the group consisting of:

RA413

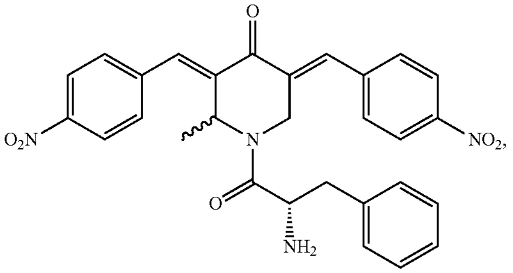

RA414

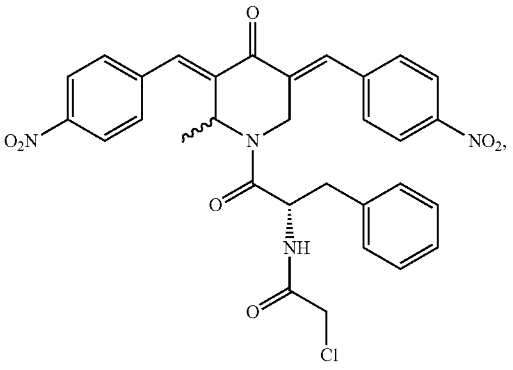

-continued

RA462

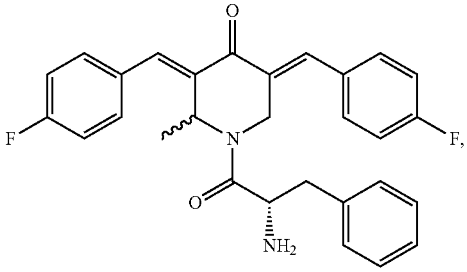

RA467

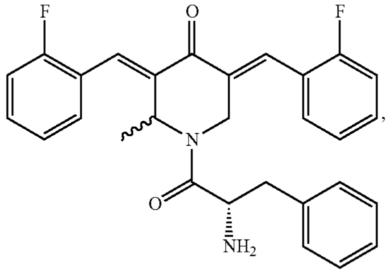

RA413S

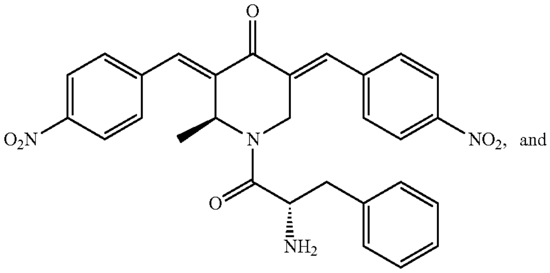

and

RA413R

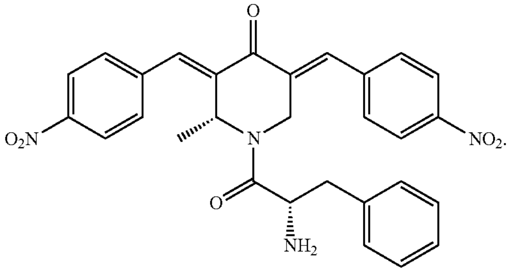

9. The compound of claim 1, wherein, when R3-methyl, the configuration at Carbon 2 of formula (I) is the R configuration, S configuration, or equimolar mixture of R and S.

10. The compound of claim 9, wherein the configuration at Carbon 2 is the S configuration.

11. A method of treating a condition or a disease in a mammal by administering to the mammal a therapeutically effective dose of a compound of claim 1 to the mammal.

12. The method of claim 11, wherein the compound is selected from the group consisting of:

RA413

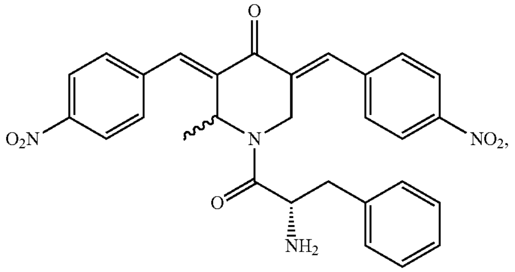

RA414

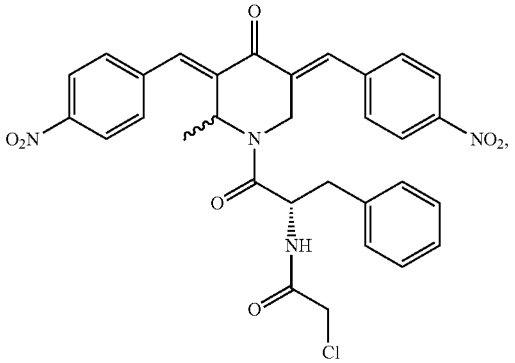

RA462

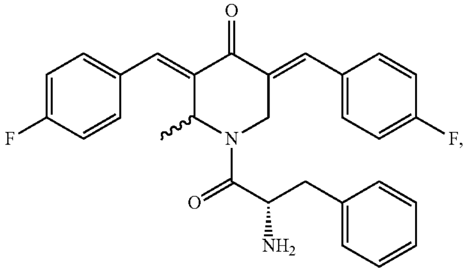

RA467

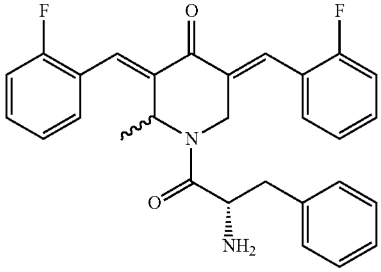

and

RA413S

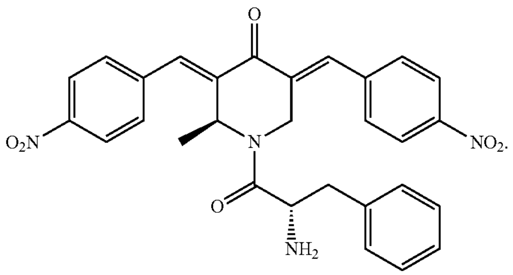

13. The method of claim 11, wherein the condition or disease is a type of cancer.

14. The method of claim 13, wherein the cancer is selected from the group consisting of breast cancer, cervical cancer, ovarian cancer, multiple myeloma, breast cancer, pancreatic cancer, and a cancer associated with Human Papilloma Virus (HPV).

15. The method of claim 13, wherein the cancer is ovarian cancer.

16. The method of claim 11, wherein the compound is administered in combination with at least one other therapeutic agent.

17. The method of claim 16, wherein the at least one other therapeutic agent is a proteasome inhibitor or a DNA damaging agent, bortezomib or cisplatin.

18. The compound of claim 1, wherein

R is H, or $C(O)CH_2Cl$;

$R_1$ is $NO_2$ or halogen;

n is 1 or 2;

$R_2$ is benzyl; and $R_3$ is methyl.

* * * * *